(12) United States Patent
Gifford, III et al.

(10) Patent No.: US 9,770,331 B2
(45) Date of Patent: Sep. 26, 2017

(54) SYSTEM FOR MITRAL VALVE REPAIR AND REPLACEMENT

(71) Applicant: Twelve, Inc., Menlo Park, CA (US)

(72) Inventors: Hanson S. Gifford, III, Woodside, CA (US); James I. Fann, Portola Valley, CA (US); John Morriss, San Francisco, CA (US); Mark Deem, Mountain View, CA (US); Jeffry J. Grainger, Portola Valley, CA (US)

(73) Assignee: Twelve, Inc., Menlo Park, CA (US)

( * ) Notice: Subject to any disclaimer, the term of this patent is extended or adjusted under 35 U.S.C. 154(b) by 0 days.

(21) Appl. No.: 15/211,940

(22) Filed: Jul. 15, 2016

(65) Prior Publication Data

US 2016/0324640 A1 Nov. 10, 2016

Related U.S. Application Data

(62) Division of application No. 13/329,083, filed on Dec. 16, 2011, now Pat. No. 9,421,098.

(Continued)

(51) Int. Cl.
*A61F 2/24* (2006.01)

(52) U.S. Cl.
CPC .......... *A61F 2/2454* (2013.01); *A61F 2/2418* (2013.01); *A61F 2/2445* (2013.01);
(Continued)

(58) Field of Classification Search
CPC .... A61F 2/2454; A61F 2/2418; A61F 2/2445; A61F 2/2466; A61F 2/2433;
(Continued)

(56) References Cited

U.S. PATENT DOCUMENTS

| 3,526,219 A | 9/1970 | Balamuth |
|---|---|---|
| 3,565,062 A | 2/1971 | Kuris |

(Continued)

FOREIGN PATENT DOCUMENTS

| CN | 101076290 | 11/2007 |
|---|---|---|
| CN | 103491900 | 1/2014 |

(Continued)

OTHER PUBLICATIONS

US 9,265,606, 02/2016, Buchbinder et al. (withdrawn)

(Continued)

*Primary Examiner* — Paul Prebilic

(57) ABSTRACT

Systems for mitral valve repair are disclosed where one or more mitral valve interventional devices may be advanced intravascularly into the heart of a patient and deployed upon or along the mitral valve to stabilize the valve leaflets. The interventional device may also facilitate the placement or anchoring of a prosthetic mitral valve implant. The interventional device may generally comprise a distal set of arms pivotably and/or rotating coupled to a proximal set of arms which are also pivotably and/or rotating coupled. The distal set of arms may be advanced past the catheter opening to a subannular position (e.g., below the mitral valve) and reconfigured from a low-profile delivery configuration to a deployed securement configuration. The proximal arm members may then be deployed such that the distal and proximal arm members may grip the leaflets between the two sets of arms to stabilize the leaflets.

10 Claims, 46 Drawing Sheets

Related U.S. Application Data

(60) Provisional application No. 61/460,041, filed on Dec. 23, 2010, provisional application No. 61/499,630, filed on Jun. 21, 2011.

(52) U.S. Cl.
CPC ............ *A61F 2/2466* (2013.01); *A61F 2/243* (2013.01); *A61F 2220/0016* (2013.01); *A61F 2220/0075* (2013.01); *A61F 2230/0008* (2013.01); *A61F 2250/0003* (2013.01); *A61F 2250/0004* (2013.01); *A61F 2250/006* (2013.01); *A61F 2250/0008* (2013.01)

(58) Field of Classification Search
CPC .................. A61F 2/2409; A61F 2/2457; A61F 2220/0075; A61F 2220/0008; A61F 2220/0091; A61F 2230/001; A61F 2250/0006; A61F 2250/0007
See application file for complete search history.

(56) References Cited

U.S. PATENT DOCUMENTS

| | | | |
|---|---|---|---|
| 3,589,363 | A | 6/1971 | Banko et al. |
| 3,667,474 | A | 6/1972 | Lapkin et al. |
| 3,823,717 | A | 7/1974 | Pohlman et al. |
| 3,861,391 | A | 1/1975 | Antonevich et al. |
| 3,896,811 | A | 7/1975 | Storz |
| 4,042,979 | A | 8/1977 | Angell |
| 4,188,952 | A | 2/1980 | Loschilov et al. |
| 4,431,006 | A | 2/1984 | Trimmer et al. |
| 4,445,509 | A | 5/1984 | Auth |
| 4,484,579 | A | 11/1984 | Meno et al. |
| 4,490,859 | A | 1/1985 | Black et al. |
| 4,587,958 | A | 5/1986 | Noguchi et al. |
| 4,589,419 | A | 5/1986 | Laughlin et al. |
| 4,602,911 | A | 7/1986 | Ahmadi et al. |
| 4,646,736 | A | 3/1987 | Auth |
| 4,692,139 | A | 9/1987 | Stiles |
| 4,747,821 | A | 5/1988 | Kensey et al. |
| 4,750,902 | A | 6/1988 | Wuchinich et al. |
| 4,777,951 | A | 10/1988 | Cribier et al. |
| 4,787,388 | A | 11/1988 | Hofmann |
| 4,796,629 | A | 1/1989 | Grayzel |
| 4,808,153 | A | 2/1989 | Parisi |
| 4,819,751 | A | 4/1989 | Shimada et al. |
| 4,841,977 | A | 6/1989 | Griffith et al. |
| 4,870,953 | A | 10/1989 | DonMicheal et al. |
| 4,878,495 | A | 11/1989 | Grayzel |
| 4,898,575 | A | 2/1990 | Fischell et al. |
| 4,909,252 | A | 3/1990 | Goldberger |
| 4,919,133 | A | 4/1990 | Chiang |
| 4,920,954 | A | 5/1990 | Alliger et al. |
| 4,936,281 | A | 6/1990 | Stasz |
| 4,960,411 | A | 10/1990 | Buchbinder |
| 4,986,830 | A | 1/1991 | Owens et al. |
| 4,990,134 | A | 2/1991 | Auth |
| 5,058,570 | A | 10/1991 | Idemoto et al. |
| 5,069,664 | A | 12/1991 | Guess et al. |
| 5,076,276 | A | 12/1991 | Sakurai et al. |
| 5,106,302 | A | 4/1992 | Farzin-Nia et al. |
| 5,248,296 | A | 9/1993 | Alliger |
| 5,267,954 | A | 12/1993 | Nita |
| 5,269,291 | A | 12/1993 | Carter |
| 5,295,958 | A | 3/1994 | Shturman |
| 5,304,115 | A | 4/1994 | Pflueger et al. |
| 5,314,407 | A | 5/1994 | Auth et al. |
| 5,318,014 | A | 6/1994 | Carter |
| 5,332,402 | A | 7/1994 | Teitelbaum |
| 5,344,426 | A | 9/1994 | Lau et al. |
| 5,352,199 | A | 10/1994 | Tower |
| 5,356,418 | A | 10/1994 | Shturman |
| 5,397,293 | A | 3/1995 | Alliger et al. |
| 5,411,552 | A | 5/1995 | Andersen et al. |
| 5,443,446 | A | 8/1995 | Shturman |
| 5,449,373 | A | 9/1995 | Pinchasik et al. |
| 5,489,297 | A | 2/1996 | Duran |
| 5,584,879 | A | 12/1996 | Reimold et al. |
| 5,609,151 | A | 3/1997 | Mulier et al. |
| 5,626,603 | A | 5/1997 | Venturelli et al. |
| 5,656,036 | A | 8/1997 | Palmaz |
| 5,662,671 | A | 9/1997 | Barbut et al. |
| 5,681,336 | A | 10/1997 | Clement et al. |
| 5,695,507 | A | 12/1997 | Auth et al. |
| 5,725,494 | A | 3/1998 | Brisken |
| 5,782,931 | A | 7/1998 | Yang et al. |
| 5,817,101 | A | 10/1998 | Fiedler |
| 5,827,229 | A | 10/1998 | Auth et al. |
| 5,827,321 | A | 10/1998 | Roubin et al. |
| 5,840,081 | A | 11/1998 | Andersen et al. |
| 5,855,601 | A | 1/1999 | Bessler et al. |
| 5,868,781 | A | 2/1999 | Killion |
| 5,873,811 | A | 2/1999 | Wang et al. |
| 5,904,679 | A | 5/1999 | Clayman |
| 5,957,882 | A | 9/1999 | Nita et al. |
| 5,989,208 | A | 11/1999 | Nita |
| 6,047,700 | A | 4/2000 | Eggers et al. |
| 6,056,759 | A | 5/2000 | Fiedler |
| 6,113,608 | A | 9/2000 | Monroe et al. |
| RE36,939 | E | 10/2000 | Tachibana et al. |
| 6,129,734 | A | 10/2000 | Shturman et al. |
| 6,132,444 | A | 10/2000 | Shturman et al. |
| 6,168,579 | B1 | 1/2001 | Tsugita |
| 6,217,595 | B1 | 4/2001 | Shturman et al. |
| 6,254,635 | B1 | 7/2001 | Schroeder et al. |
| 6,295,712 | B1 | 10/2001 | Shturman et al. |
| 6,306,414 | B1 | 10/2001 | Koike |
| 6,321,109 | B2 | 11/2001 | Ben-Haim et al. |
| 6,423,032 | B2 | 7/2002 | Parodi |
| 6,440,164 | B1 | 8/2002 | DiMatteo et al. |
| 6,454,737 | B1 | 9/2002 | Nita et al. |
| 6,454,757 | B1 | 9/2002 | Nita et al. |
| 6,454,799 | B1 | 9/2002 | Schreck |
| 6,458,153 | B1 | 10/2002 | Bailey et al. |
| 6,461,382 | B1 | 10/2002 | Cao |
| 6,494,890 | B1 | 12/2002 | Shturman et al. |
| 6,494,891 | B1 | 12/2002 | Cornish et al. |
| 6,505,080 | B1 | 1/2003 | Sutton |
| 6,530,952 | B2 * | 3/2003 | Vesely .................. A61F 2/2409 623/1.24 |
| 6,540,782 | B1 | 4/2003 | Snyders |
| 6,562,067 | B2 | 5/2003 | Mathis |
| 6,565,588 | B1 | 5/2003 | Clement et al. |
| 6,579,308 | B1 | 6/2003 | Jansen et al. |
| 6,582,462 | B1 | 6/2003 | Andersen et al. |
| 6,605,109 | B2 | 8/2003 | Fiedler |
| 6,616,689 | B1 | 9/2003 | Ainsworth et al. |
| 6,623,452 | B2 | 9/2003 | Chien et al. |
| 6,638,288 | B1 | 10/2003 | Shturman et al. |
| 6,648,854 | B1 | 11/2003 | Patterson et al. |
| 6,689,086 | B1 | 2/2004 | Nita et al. |
| 6,702,748 | B1 | 3/2004 | Nita et al. |
| 6,730,121 | B2 | 5/2004 | Ortiz et al. |
| 6,746,463 | B1 | 6/2004 | Schwartz |
| 6,811,801 | B2 | 11/2004 | Nguyen et al. |
| 6,818,001 | B2 | 11/2004 | Wulfman et al. |
| 6,843,797 | B2 | 1/2005 | Nash et al. |
| 6,852,118 | B2 | 2/2005 | Shturman et al. |
| 6,855,123 | B2 | 2/2005 | Nita |
| 6,869,439 | B2 | 3/2005 | White et al. |
| 6,951,571 | B1 | 10/2005 | Srivastava |
| 6,986,775 | B2 | 1/2006 | Morales et al. |
| 7,018,404 | B2 | 3/2006 | Holmberg et al. |
| 7,052,487 | B2 | 5/2006 | Cohn et al. |
| 7,077,861 | B2 | 7/2006 | Spence |
| 7,125,420 | B2 | 10/2006 | Rourke et al. |
| 7,186,264 | B2 | 3/2007 | Liddicoat et al. |
| 7,261,732 | B2 | 8/2007 | Justino |
| 7,296,577 | B2 | 11/2007 | Lashinski et al. |
| 7,381,218 | B2 | 6/2008 | Schreck |
| 7,404,824 | B1 | 7/2008 | Webler et al. |
| 7,442,204 | B2 | 10/2008 | Schwammenthal et al. |
| 7,473,275 | B2 | 1/2009 | Marquez |

(56) References Cited

U.S. PATENT DOCUMENTS

| | | |
|---|---|---|
| 7,510,575 B2 | 3/2009 | Spenser et al. |
| 7,585,321 B2 | 9/2009 | Cribier |
| 7,588,582 B2 | 9/2009 | Starksen et al. |
| 7,621,948 B2 | 11/2009 | Herrmann et al. |
| 7,708,775 B2 | 5/2010 | Rowe et al. |
| 7,748,389 B2 | 7/2010 | Salahieh et al. |
| 7,753,922 B2 | 7/2010 | Starksen |
| 7,753,949 B2 | 7/2010 | Lamphere et al. |
| 7,803,168 B2 | 9/2010 | Gifford et al. |
| 7,857,845 B2 | 12/2010 | Stacchino et al. |
| 7,896,915 B2 | 3/2011 | Guyenot et al. |
| 7,942,928 B2 | 5/2011 | Webler et al. |
| 8,002,826 B2 | 8/2011 | Seguin |
| 8,052,750 B2 | 11/2011 | Tuval et al. |
| 8,062,355 B2 | 11/2011 | Figulla et al. |
| 8,109,996 B2 | 2/2012 | Stacchino et al. |
| 8,114,154 B2 | 2/2012 | Righini et al. |
| 8,252,051 B2 | 8/2012 | Chau et al. |
| 8,398,704 B2 | 3/2013 | Straubinger et al. |
| 8,414,643 B2 | 4/2013 | Tuval et al. |
| 8,496,671 B1 | 7/2013 | Hausen |
| 8,512,252 B2 | 8/2013 | Ludomirsky et al. |
| 8,518,107 B2 | 8/2013 | Tsukashima et al. |
| 8,523,883 B2 | 9/2013 | Saadat |
| 8,532,352 B2 | 9/2013 | Ionasec et al. |
| 8,540,767 B2 | 9/2013 | Zhang |
| 8,545,551 B2 | 10/2013 | Loulmet |
| 8,551,161 B2 | 10/2013 | Dolan |
| 8,579,788 B2 | 11/2013 | Orejola |
| 8,579,964 B2 | 11/2013 | Lane et al. |
| 8,585,755 B2 | 11/2013 | Chau et al. |
| 8,597,347 B2 | 12/2013 | Maurer et al. |
| 8,597,348 B2 | 12/2013 | Rowe et al. |
| 8,608,796 B2 | 12/2013 | Matheny |
| 8,608,797 B2 | 12/2013 | Gross et al. |
| 8,623,077 B2 | 1/2014 | Cohn |
| 8,628,566 B2 | 1/2014 | Eberhardt et al. |
| 8,632,585 B2 | 1/2014 | Seguin et al. |
| 8,632,586 B2 | 1/2014 | Spenser et al. |
| 8,634,935 B2 | 1/2014 | Gaudiani |
| 8,647,254 B2 | 2/2014 | Callas et al. |
| 8,652,204 B2 | 2/2014 | Quill et al. |
| 8,657,872 B2 | 2/2014 | Seguin |
| 8,672,998 B2 | 3/2014 | Lichtenstein et al. |
| 8,673,001 B2 | 3/2014 | Cartledge et al. |
| 8,679,176 B2 | 3/2014 | Matheny |
| 8,688,234 B2 | 4/2014 | Zhu et al. |
| 8,690,858 B2 | 4/2014 | Machold et al. |
| 8,709,074 B2 | 4/2014 | Solem et al. |
| 8,712,133 B2 | 4/2014 | Guhring et al. |
| 8,715,160 B2 | 5/2014 | Raman et al. |
| 8,721,665 B2 | 5/2014 | Oz et al. |
| 8,721,718 B2 | 5/2014 | Kassab |
| 8,808,356 B2 | 8/2014 | Braido et al. |
| 8,808,366 B2 | 8/2014 | Braido et al. |
| 8,828,043 B2 | 9/2014 | Chambers |
| 8,845,717 B2 | 9/2014 | Khairkhahan et al. |
| 8,845,723 B2 | 9/2014 | Spence et al. |
| 8,852,213 B2 | 10/2014 | Gammie et al. |
| 8,852,272 B2 | 10/2014 | Gross et al. |
| 9,271,833 B2 | 3/2016 | Kim et al. |
| 9,289,291 B2 | 3/2016 | Gorman, III et al. |
| 9,289,927 B2 | 3/2016 | Weber et al. |
| 9,295,547 B2 | 3/2016 | Costello et al. |
| 9,301,836 B2 | 4/2016 | Buchbinder et al. |
| 9,308,087 B2 | 4/2016 | Lane et al. |
| 9,326,850 B2 | 5/2016 | Venkatasubramanian |
| 9,339,378 B2 | 5/2016 | Quadri et al. |
| 9,339,379 B2 | 5/2016 | Quadri et al. |
| 9,339,382 B2 | 5/2016 | Tabor et al. |
| 9,387,075 B2 | 7/2016 | Bortlein et al. |
| 9,387,078 B2 | 7/2016 | Gross et al. |
| 9,421,098 B2* | 8/2016 | Gifford, III ............ A61F 2/2418 |
| 2001/0021872 A1* | 9/2001 | Bailey ................ A61F 2/2418 623/1.24 |
| 2001/0049492 A1 | 12/2001 | Frazier et al. |
| 2002/0007219 A1 | 1/2002 | Merrill et al. |
| 2002/0072792 A1 | 6/2002 | Burgermeister et al. |
| 2002/0082637 A1 | 6/2002 | Lumauig |
| 2002/0099439 A1 | 7/2002 | Schwartz et al. |
| 2002/0151970 A1 | 10/2002 | Garrison et al. |
| 2002/0173841 A1 | 11/2002 | Ortiz et al. |
| 2003/0120340 A1 | 6/2003 | Liska et al. |
| 2003/0139689 A1 | 7/2003 | Shturman et al. |
| 2004/0006358 A1 | 1/2004 | Wulfman et al. |
| 2004/0039412 A1 | 2/2004 | Isshiki et al. |
| 2004/0044350 A1 | 3/2004 | Martin et al. |
| 2004/0057955 A1 | 3/2004 | O'Brien et al. |
| 2004/0082910 A1 | 4/2004 | Constantz et al. |
| 2004/0092858 A1 | 5/2004 | Wilson et al. |
| 2004/0092962 A1 | 5/2004 | Thornton et al. |
| 2004/0092989 A1 | 5/2004 | Wilson et al. |
| 2004/0106989 A1 | 6/2004 | Wilson et al. |
| 2004/0117009 A1 | 6/2004 | Cali et al. |
| 2004/0122510 A1* | 6/2004 | Sarac ................ A61F 2/07 623/1.36 |
| 2004/0127979 A1 | 7/2004 | Wilson et al. |
| 2004/0127982 A1* | 7/2004 | Machold ............. A61F 2/2418 623/2.36 |
| 2004/0186558 A1 | 9/2004 | Pavcnik et al. |
| 2004/0199191 A1 | 10/2004 | Schwartz |
| 2004/0230117 A1 | 11/2004 | Tosaya et al. |
| 2004/0230212 A1 | 11/2004 | Wulfman |
| 2004/0230213 A1 | 11/2004 | Wulfman et al. |
| 2004/0243162 A1 | 12/2004 | Wulfman et al. |
| 2005/0007219 A1 | 1/2005 | Ma et al. |
| 2005/0075662 A1 | 4/2005 | Pedersen et al. |
| 2005/0075720 A1 | 4/2005 | Nguyen et al. |
| 2005/0137682 A1 | 6/2005 | Justino |
| 2005/0137690 A1* | 6/2005 | Salahieh ............. A61F 2/2418 623/2.11 |
| 2005/0137691 A1 | 6/2005 | Salahieh et al. |
| 2005/0137695 A1 | 6/2005 | Salahieh et al. |
| 2005/0137697 A1 | 6/2005 | Salahieh et al. |
| 2005/0137698 A1 | 6/2005 | Salahieh et al. |
| 2005/0137701 A1 | 6/2005 | Salahieh et al. |
| 2005/0137702 A1 | 6/2005 | Haug et al. |
| 2005/0267523 A1 | 12/2005 | Devellian et al. |
| 2006/0058872 A1 | 3/2006 | Salahieh et al. |
| 2006/0106456 A9 | 5/2006 | Machold et al. |
| 2006/0149360 A1 | 7/2006 | Schwammenthal et al. |
| 2006/0167543 A1 | 7/2006 | Bailey et al. |
| 2006/0195183 A1 | 8/2006 | Navia et al. |
| 2006/0253191 A1 | 11/2006 | Salahieh et al. |
| 2006/0287719 A1 | 12/2006 | Rowe et al. |
| 2007/0061010 A1 | 3/2007 | Hauser et al. |
| 2007/0073391 A1 | 3/2007 | Bourang et al. |
| 2007/0088431 A1 | 4/2007 | Bourang et al. |
| 2007/0142906 A1 | 6/2007 | Figulla et al. |
| 2007/0173932 A1 | 7/2007 | Cali et al. |
| 2008/0071369 A1 | 3/2008 | Tuval et al. |
| 2008/0082166 A1 | 4/2008 | Styrc et al. |
| 2008/0103586 A1 | 5/2008 | Styrc et al. |
| 2008/0140189 A1 | 6/2008 | Nguyen et al. |
| 2008/0208332 A1 | 8/2008 | Lamphere et al. |
| 2008/0221672 A1 | 9/2008 | Lamphere et al. |
| 2008/0234728 A1 | 9/2008 | Starksen et al. |
| 2008/0243245 A1 | 10/2008 | Thambar et al. |
| 2008/0243246 A1 | 10/2008 | Ryan et al. |
| 2009/0054969 A1 | 2/2009 | Salahieh et al. |
| 2009/0076586 A1 | 3/2009 | Hauser et al. |
| 2009/0076598 A1 | 3/2009 | Salahieh et al. |
| 2009/0093670 A1 | 4/2009 | Annest et al. |
| 2009/0157174 A1 | 6/2009 | Yoganathan et al. |
| 2009/0164006 A1 | 6/2009 | Seguin et al. |
| 2009/0198315 A1 | 8/2009 | Boudjemline |
| 2009/0216312 A1 | 8/2009 | Straubinger et al. |
| 2009/0240320 A1 | 9/2009 | Tuval et al. |
| 2009/0259292 A1 | 10/2009 | Bonhoeffer |
| 2009/0259306 A1 | 10/2009 | Rowe |
| 2009/0264997 A1 | 10/2009 | Salahieh et al. |
| 2009/0276040 A1 | 11/2009 | Rowe et al. |
| 2009/0281609 A1 | 11/2009 | Benichou et al. |
| 2009/0292350 A1 | 11/2009 | Eberhardt et al. |

(56) References Cited

U.S. PATENT DOCUMENTS

| | | |
|---|---|---|
| 2009/0306768 A1 | 12/2009 | Quadri |
| 2009/0319037 A1 | 12/2009 | Rowe et al. |
| 2009/0319038 A1 | 12/2009 | Gurskis et al. |
| 2010/0016958 A1 | 1/2010 | St. Goar et al. |
| 2010/0023117 A1 | 1/2010 | Yoganathan et al. |
| 2010/0030330 A1 | 2/2010 | Bobo et al. |
| 2010/0076548 A1 | 3/2010 | Konno |
| 2010/0082094 A1 | 4/2010 | Quadri et al. |
| 2010/0094411 A1 | 4/2010 | Tuval et al. |
| 2010/0121436 A1 | 5/2010 | Tuval et al. |
| 2010/0185275 A1 | 7/2010 | Richer et al. |
| 2010/0217382 A1 | 8/2010 | Chau et al. |
| 2010/0249915 A1 | 9/2010 | Zhang |
| 2010/0298929 A1 | 11/2010 | Thornton et al. |
| 2010/0298931 A1 | 11/2010 | Quadri et al. |
| 2010/0312333 A1 | 12/2010 | Navia et al. |
| 2010/0324554 A1 | 12/2010 | Gifford et al. |
| 2011/0004296 A1 | 1/2011 | Lutter et al. |
| 2011/0015722 A1 | 1/2011 | Hauser et al. |
| 2011/0022166 A1 | 1/2011 | Dahlgren et al. |
| 2011/0029072 A1 | 2/2011 | Gabbay |
| 2011/0040374 A1 | 2/2011 | Goetz et al. |
| 2011/0040375 A1 | 2/2011 | Letac et al. |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1* | 6/2011 | Chau .............. A61F 2/2418 623/1.11 |
| 2011/0137409 A1 | 6/2011 | Yang et al. |
| 2011/0137410 A1* | 6/2011 | Hacohen .......... A61F 2/2412 623/2.37 |
| 2011/0153008 A1 | 6/2011 | Marchand et al. |
| 2011/0172784 A1 | 7/2011 | Richter et al. |
| 2011/0184512 A1 | 7/2011 | Webler et al. |
| 2011/0208293 A1 | 8/2011 | Tabor |
| 2011/0224785 A1 | 9/2011 | Hacohen |
| 2012/0022639 A1 | 1/2012 | Hacohen et al. |
| 2012/0053680 A1 | 3/2012 | Bolling et al. |
| 2012/0053682 A1 | 3/2012 | Kovalsky et al. |
| 2012/0059458 A1* | 3/2012 | Buchbinder ...... A61F 2/2409 623/2.36 |
| 2012/0078347 A1 | 3/2012 | Braido et al. |
| 2012/0078360 A1 | 3/2012 | Rafiee |
| 2012/0101571 A1 | 4/2012 | Thambar et al. |
| 2012/0165930 A1 | 6/2012 | Gifford, III et al. |
| 2012/0179239 A1 | 7/2012 | Quadri |
| 2012/0179244 A1 | 7/2012 | Schankereli et al. |
| 2012/0203336 A1 | 8/2012 | Annest |
| 2013/0197354 A1 | 8/2013 | Maschke et al. |
| 2013/0197630 A1 | 8/2013 | Azarnoush |
| 2013/0204356 A1 | 8/2013 | Dwork et al. |
| 2013/0204358 A1 | 8/2013 | Matheny |
| 2013/0226289 A1 | 8/2013 | Shaolian et al. |
| 2013/0226290 A1 | 8/2013 | Yellin et al. |
| 2013/0231735 A1 | 9/2013 | Deem et al. |
| 2013/0238089 A1 | 9/2013 | Lichtenstein et al. |
| 2013/0244927 A1 | 9/2013 | Lal et al. |
| 2013/0253641 A1 | 9/2013 | Lattouf |
| 2013/0253642 A1 | 9/2013 | Brecker |
| 2013/0253643 A1 | 9/2013 | Rolando et al. |
| 2013/0259337 A1 | 10/2013 | Guhring et al. |
| 2013/0261737 A1 | 10/2013 | Costello |
| 2013/0261738 A1 | 10/2013 | Clague et al. |
| 2013/0261739 A1 | 10/2013 | Kuehn |
| 2013/0261741 A1 | 10/2013 | Accola |
| 2013/0268066 A1 | 10/2013 | Rowe |
| 2013/0282059 A1 | 10/2013 | Ketai et al. |
| 2013/0282060 A1 | 10/2013 | Tuval |
| 2013/0282110 A1 | 10/2013 | Schweich, Jr. et al. |
| 2013/0289642 A1 | 10/2013 | Hedberg et al. |
| 2013/0289717 A1 | 10/2013 | Solem |
| 2013/0289718 A1 | 10/2013 | Tsukashima et al. |
| 2013/0296851 A1 | 11/2013 | Boronyak et al. |
| 2013/0304197 A1 | 11/2013 | Buchbinder et al. |
| 2013/0304198 A1 | 11/2013 | Solem |
| 2013/0304200 A1 | 11/2013 | McLean et al. |
| 2013/0309292 A1 | 11/2013 | Andersen |
| 2013/0310436 A1 | 11/2013 | Lowes et al. |
| 2013/0310925 A1 | 11/2013 | Eliasen et al. |
| 2013/0310928 A1* | 11/2013 | Morriss .............. A61F 2/2418 623/2.12 |
| 2013/0317603 A1 | 11/2013 | McLean et al. |
| 2013/0325110 A1 | 12/2013 | Khalil et al. |
| 2013/0325114 A1 | 12/2013 | McLean et al. |
| 2013/0331864 A1 | 12/2013 | Jelich et al. |
| 2013/0338684 A1 | 12/2013 | Hausen |
| 2013/0338763 A1 | 12/2013 | Rowe et al. |
| 2013/0345797 A1 | 12/2013 | Dahlgren et al. |
| 2013/0345803 A1 | 12/2013 | Bergheim, III |
| 2014/0005778 A1 | 1/2014 | Buchbinder et al. |
| 2014/0018906 A1 | 1/2014 | Rafiee |
| 2014/0018913 A1 | 1/2014 | Cartledge et al. |
| 2014/0023261 A1 | 1/2014 | Watanabe et al. |
| 2014/0025164 A1 | 1/2014 | Montorfano et al. |
| 2014/0031928 A1 | 1/2014 | Murphy et al. |
| 2014/0046219 A1 | 2/2014 | Sauter et al. |
| 2014/0046436 A1 | 2/2014 | Kheradvar |
| 2014/0052237 A1 | 2/2014 | Lane et al. |
| 2014/0052240 A1 | 2/2014 | Zhang |
| 2014/0056906 A1 | 2/2014 | Yue et al. |
| 2014/0066895 A1 | 3/2014 | Kipperman |
| 2014/0067048 A1 | 3/2014 | Chau et al. |
| 2014/0067052 A1 | 3/2014 | Chau et al. |
| 2014/0067054 A1 | 3/2014 | Chau et al. |
| 2014/0088071 A1 | 3/2014 | Nakai et al. |
| 2014/0088680 A1 | 3/2014 | Costello et al. |
| 2014/0088693 A1 | 3/2014 | Seguin et al. |
| 2014/0088695 A1 | 3/2014 | Figulla et al. |
| 2014/0094906 A1 | 4/2014 | Spence et al. |
| 2014/0107775 A1 | 4/2014 | Hjelle et al. |
| 2014/0114404 A1 | 4/2014 | Gammie et al. |
| 2014/0114407 A1 | 4/2014 | Rajamannan |
| 2014/0128965 A1 | 5/2014 | Rafiee |
| 2014/0135913 A1 | 5/2014 | Lichtenstein et al. |
| 2014/0163652 A1 | 6/2014 | Witzel et al. |
| 2014/0163668 A1 | 6/2014 | Rafiee |
| 2014/0172076 A1 | 6/2014 | Jonsson et al. |
| 2014/0172084 A1 | 6/2014 | Callas et al. |
| 2014/0172085 A1 | 6/2014 | Quadri et al. |
| 2014/0172086 A1 | 6/2014 | Quadri et al. |
| 2014/0179993 A1 | 6/2014 | Alexander et al. |
| 2014/0180401 A1 | 6/2014 | Quill et al. |
| 2014/0188108 A1 | 7/2014 | Goodine et al. |
| 2014/0188215 A1 | 7/2014 | Hlavka et al. |
| 2014/0194920 A1 | 7/2014 | Krahbichler |
| 2014/0194976 A1 | 7/2014 | Starksen et al. |
| 2014/0200397 A1 | 7/2014 | Raman et al. |
| 2014/0200657 A1 | 7/2014 | Maurer et al. |
| 2014/0200662 A1 | 7/2014 | Eftel et al. |
| 2014/0214159 A1 | 7/2014 | Vidlund et al. |
| 2014/0219524 A1 | 8/2014 | Takeguchi et al. |
| 2014/0222040 A1 | 8/2014 | Park et al. |
| 2014/0222138 A1 | 8/2014 | Machold et al. |
| 2014/0228942 A1 | 8/2014 | Krahbichler |
| 2014/0228946 A1 | 8/2014 | Chau et al. |
| 2014/0242086 A1 | 8/2014 | Lal et al. |
| 2014/0243860 A1 | 8/2014 | Morris et al. |
| 2014/0243954 A1 | 8/2014 | Shannon |
| 2014/0243964 A1 | 8/2014 | Venkatasubramanian |
| 2014/0249621 A1 | 9/2014 | Eidenschink |
| 2014/0257101 A1 | 9/2014 | Gaudiani |
| 2014/0257466 A1 | 9/2014 | Board et al. |
| 2014/0257467 A1 | 9/2014 | Lane et al. |
| 2014/0257473 A1 | 9/2014 | Rajamannan |
| 2014/0257475 A1 | 9/2014 | Gross et al. |
| 2014/0275757 A1 | 9/2014 | Goodwin et al. |
| 2014/0276395 A1 | 9/2014 | Wilson et al. |
| 2014/0276609 A1 | 9/2014 | Magee et al. |
| 2014/0276782 A1 | 9/2014 | Paskar |
| 2014/0276971 A1 | 9/2014 | Kovach |
| 2014/0277119 A1 | 9/2014 | Akpinar |
| 2014/0277390 A1 | 9/2014 | Ratz et al. |
| 2014/0277404 A1 | 9/2014 | Wilson et al. |
| 2014/0277405 A1 | 9/2014 | Wilson et al. |

(56) References Cited

U.S. PATENT DOCUMENTS

| | | |
|---|---|---|
| 2014/0277406 A1 | 9/2014 | Arcidi |
| 2014/0277407 A1 | 9/2014 | Dale et al. |
| 2014/0277408 A1 | 9/2014 | Folan |
| 2014/0277409 A1 | 9/2014 | Bortlein et al. |
| 2014/0277410 A1 | 9/2014 | Bortlein et al. |
| 2014/0277411 A1 | 9/2014 | Bortlein et al. |
| 2014/0277412 A1 | 9/2014 | Bortlein et al. |
| 2014/0277420 A1 | 9/2014 | Migliazza et al. |
| 2014/0277422 A1 | 9/2014 | Ratz et al. |
| 2014/0288480 A1 | 9/2014 | Zimmerman et al. |
| 2014/0296878 A1 | 10/2014 | Oz et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296975 A1 | 10/2014 | Tegels et al. |
| 2014/0303719 A1 | 10/2014 | Cox et al. |
| 2014/0303721 A1 | 10/2014 | Fung et al. |
| 2014/0364944 A1 | 12/2014 | Lutter et al. |
| 2014/0379076 A1 | 12/2014 | Vidlund et al. |
| 2015/0342733 A1 | 12/2015 | Alkhatib et al. |

FOREIGN PATENT DOCUMENTS

| | | |
|---|---|---|
| DE | 19605042 | 1/1998 |
| EP | 1512383 | 3/2005 |
| EP | 1629794 | 3/2006 |
| EP | 2026280 | 2/2009 |
| EP | 2037829 | 3/2009 |
| EP | 2081519 | 7/2009 |
| EP | 2111190 | 10/2009 |
| EP | 2167742 | 3/2010 |
| EP | 2278944 | 2/2011 |
| EP | 2306821 | 4/2011 |
| EP | 2327429 | 6/2011 |
| EP | 2400926 | 1/2012 |
| EP | 2444031 | 4/2012 |
| EP | 2488126 | 8/2012 |
| EP | 2566416 | 3/2013 |
| EP | 2586492 | 5/2013 |
| EP | 2618784 | 7/2013 |
| EP | 2623068 | 8/2013 |
| EP | 2626012 | 8/2013 |
| EP | 2626013 | 8/2013 |
| EP | 2629699 | 8/2013 |
| EP | 2633457 | 9/2013 |
| EP | 2637659 | 9/2013 |
| EP | 2641569 | 9/2013 |
| EP | 2654624 | 10/2013 |
| EP | 2656794 | 10/2013 |
| EP | 2656795 | 10/2013 |
| EP | 2656796 | 10/2013 |
| EP | 2667823 | 12/2013 |
| EP | 2670358 | 12/2013 |
| EP | 2676640 | 12/2013 |
| EP | 2688041 | 1/2014 |
| EP | 2693984 | 2/2014 |
| EP | 2697721 | 2/2014 |
| EP | 2713953 | 4/2014 |
| EP | 2714068 | 4/2014 |
| EP | 2723272 | 4/2014 |
| EP | 2723273 | 4/2014 |
| EP | 2723277 | 4/2014 |
| EP | 2739214 | 6/2014 |
| EP | 2741711 | 6/2014 |
| EP | 2750630 | 7/2014 |
| EP | 2750631 | 7/2014 |
| EP | 2755562 | 7/2014 |
| EP | 2755602 | 7/2014 |
| EP | 2757962 | 7/2014 |
| EP | 2777616 | 9/2014 |
| EP | 2777617 | 9/2014 |
| EP | 2782523 | 10/2014 |
| EP | 2785282 | 10/2014 |
| EP | 2416739 | 2/2015 |
| EP | 2981208 | 2/2016 |
| EP | 2982336 | 2/2016 |
| EP | 2999433 | 3/2016 |
| EP | 3003187 | 4/2016 |
| EP | 3003219 | 4/2016 |
| EP | 3003220 | 4/2016 |
| EP | 3010447 | 4/2016 |
| EP | 3013281 | 5/2016 |
| EP | 3017792 | 5/2016 |
| EP | 3023117 | 5/2016 |
| EP | 3027143 | 6/2016 |
| EP | 3033048 | 6/2016 |
| EP | 3037064 | 6/2016 |
| JP | 6504516 | 5/1994 |
| JP | 2002509756 | 4/2002 |
| JP | 2005280917 | 10/2005 |
| JP | 5219518 | 6/2013 |
| WO | WO-9217118 | 10/1992 |
| WO | WO-9516407 | 6/1995 |
| WO | WO-9904730 | 2/1999 |
| WO | WO-9939648 | 8/1999 |
| WO | WO-9949799 | 10/1999 |
| WO | WO-0203892 | 1/2002 |
| WO | WO-0228421 | 4/2002 |
| WO | WO-0239908 | 5/2002 |
| WO | WO-03043685 | 5/2003 |
| WO | WO-2014110169 | 5/2003 |
| WO | WO-2004084746 | 10/2004 |
| WO | WO-2004093728 | 11/2004 |
| WO | WO-2004096097 | 11/2004 |
| WO | WO-2004112657 | 12/2004 |
| WO | WO-2005002466 | 1/2005 |
| WO | WO-2005007219 | 1/2005 |
| WO | WO-2005009285 | 2/2005 |
| WO | WO-2005009506 | 2/2005 |
| WO | WO-2005087140 | 9/2005 |
| WO | WO-2006063199 | 6/2006 |
| WO | WO-2007008371 | 1/2007 |
| WO | WO-2007067820 | 6/2007 |
| WO | WO-2008103497 | 8/2008 |
| WO | WO-2008129405 | 10/2008 |
| WO | WO2009045338 | 4/2009 |
| WO | WO-2010008549 | 1/2010 |
| WO | WO-2010057262 | 5/2010 |
| WO | WO-2010080594 | 7/2010 |
| WO | WO-2010098857 | 9/2010 |
| WO | WO-2010117680 | 10/2010 |
| WO | WO-2011047168 | 4/2011 |
| WO | WO-2011051043 | 5/2011 |
| WO | WO-2011072084 | 6/2011 |
| WO | WO-2011106137 | 9/2011 |
| WO | WO-2011106544 | 9/2011 |
| WO | WO-2011111047 | 9/2011 |
| WO | WO-2011137531 | 11/2011 |
| WO | WO2011139747 | 11/2011 |
| WO | WO-2012011018 | 1/2012 |
| WO | WO-2012011108 | 1/2012 |
| WO | WO-2012027487 | 3/2012 |
| WO | WO-2012040655 | 3/2012 |
| WO | WO-2012047644 | 4/2012 |
| WO | WO-2012055498 | 5/2012 |
| WO | WO-2012087842 | 6/2012 |
| WO | WO-2012095455 | 7/2012 |
| WO | WO-2012102928 | 8/2012 |
| WO | WO-2012106602 | 8/2012 |
| WO | WO-2012118508 | 9/2012 |
| WO | WO-2012118816 | 9/2012 |
| WO | WO-2012118894 | 9/2012 |
| WO | WO-2012177942 | 12/2012 |
| WO | WO-2013021375 | 2/2013 |
| WO | WO-2013028387 | 2/2013 |
| WO | WO-2013059743 | 4/2013 |
| WO | WO-2013059747 | 4/2013 |
| WO | WO-2013114214 | 8/2013 |
| WO | WO-2013120181 | 8/2013 |
| WO | WO-2013123059 | 8/2013 |
| WO | WO-2013128432 | 9/2013 |
| WO | WO-2013130641 | 9/2013 |
| WO | WO-2013131925 | 9/2013 |
| WO | WO-2013140318 | 9/2013 |

(56) References Cited

FOREIGN PATENT DOCUMENTS

| | | |
|---|---|---|
| WO | WO-2013148017 | 10/2013 |
| WO | WO-2013148018 | 10/2013 |
| WO | WO-2013148019 | 10/2013 |
| WO | WO-2013150512 | 10/2013 |
| WO | WO-2013152161 | 10/2013 |
| WO | WO-2013158613 | 10/2013 |
| WO | WO-2013169448 | 11/2013 |
| WO | WO-2013175468 | 11/2013 |
| WO | WO-2013176583 | 11/2013 |
| WO | WO-2013188077 | 12/2013 |
| WO | WO-2013192107 | 12/2013 |
| WO | WO-2014036113 | 3/2014 |
| WO | WO-2014043527 | 3/2014 |
| WO | WO-2014047111 | 3/2014 |
| WO | WO-2014047325 | 3/2014 |
| WO | WO-2014055981 | 4/2014 |
| WO | WO-2014059432 | 4/2014 |
| WO | WO-2014064694 | 5/2014 |
| WO | WO-2014066365 | 5/2014 |
| WO | WO-2014089424 | 6/2014 |
| WO | WO-2014093861 | 6/2014 |
| WO | WO-2014111918 | 7/2014 |
| WO | WO-2014114794 | 7/2014 |
| WO | WO-2014114795 | 7/2014 |
| WO | WO-2014114796 | 7/2014 |
| WO | WO-2014114798 | 7/2014 |
| WO | WO-2014116502 | 7/2014 |
| WO | WO-2014121280 | 8/2014 |
| WO | WO-2014128705 | 8/2014 |
| WO | WO-2014134277 | 9/2014 |
| WO | WO-2014138194 | 9/2014 |
| WO | WO-2014138284 | 9/2014 |
| WO | WO-2014138482 | 9/2014 |
| WO | WO-2014138868 | 9/2014 |
| WO | WO-2014144100 | 9/2014 |
| WO | WO-2014144937 | 9/2014 |
| WO | WO-2014145338 | 9/2014 |
| WO | WO-2014147336 | 9/2014 |
| WO | WO-2014152306 | 9/2014 |
| WO | WO-2014152375 | 9/2014 |
| WO | WO-2014152503 | 9/2014 |
| WO | WO-2014153544 | 9/2014 |
| WO | WO-2014158617 | 10/2014 |
| WO | WO-2014162181 | 10/2014 |
| WO | WO-2014162306 | 10/2014 |
| WO | WO-2014163705 | 10/2014 |
| WO | WO2014181336 | 11/2014 |
| WO | WO2014189974 | 11/2014 |
| WO | WO2015191604 | 8/2015 |
| WO | WO2015191839 | 8/2015 |
| WO | WO2015195823 | 8/2015 |
| WO | WO2016011185 | 8/2015 |
| WO | WO2015142648 | 9/2015 |
| WO | WO2015142834 | 9/2015 |
| WO | WO2016020918 | 9/2015 |
| WO | WO2016027272 | 9/2015 |
| WO | WO2016059533 | 9/2015 |
| WO | WO2016065158 | 9/2015 |
| WO | WO2016073741 | 9/2015 |
| WO | WO2016083551 | 9/2015 |
| WO | WO2015148241 | 10/2015 |
| WO | WO2015171190 | 11/2015 |
| WO | WO2015171743 | 11/2015 |
| WO | WO2016097337 | 6/2016 |
| WO | WO2016108181 | 7/2016 |

OTHER PUBLICATIONS

Office Action dated Feb. 23, 2011 from Japanese Patent Application No. 2007-; 545650 together with an English language translation, 10 pages.

Cowell et al., "A randomized Trial of Intensive Lipid-Lowering Therapy in Calcific Aortic Stenosis," NEJM vol. 352 No. 23, pp. 2389-2397 (Jun. 9, 2005).

Feldman, "Restenosis Following Successful Balloon Valvuloplasty: Bone Formation in Aortic Valve Leaflets," Cathet Cardiovasc Diagn, vol. 29 No. 1, pp. 1-7 (May 1993).

Final Office Action for U.S. Appl. No. 12/870,270, Mailed Jul. 3, 2012, 7 pages.

Final Office Action for U.S. Appl. No. 11/299,246, Mailed Feb. 17, 2010, 6 pages.

Final Office Action for U.S. Appl. No. 11/299,246, Mailed Jun. 6, 2008, 5 pages.

Final Office Action for U.S. Appl. No. 13/329,083, Mailed Jan. 6, 2014, 9 pages.

Final Office Action for U.S. Appl. No. 13/842,785, mailed Aug. 29, 2014, 5 pages.

Final Office Action for U.S. Appl. No. 13/946,552, Mailed Aug. 29, 2014, 5 pages.

Final Office Action for U.S. Appl. No. 13/946,628, Mailed Sep. 2, 2014, 6 pages.

Freeman et al., "Ultrasonic Aortic Valve Decalcification: Serial Doppler Echocardiographic Follow Up," J Am Coll Cardiol., vol. 16, No. 3, pp. 623-630 (Sep. 1990).

Gunn et al., "New Developments in Therapeutic Ultrasound-Assisted Coronary Angioplasty," Curr Interv Cardiol Rep., vol. 1 No. 4, pp. 281-290, (Dec. 1990).

International Search Report and Written Opinion dated May 1, 2012; International Application No. PCT/US2011/065627; Applicant: Foundry Newco XII, Inc.; 10 pages.

International Search Report and Written Opinion dated Dec. 10, 2012; International Application No. PCT/US2012/043636; Applicant: Foundry Newco XII, Inc.; 21 pages.

International Search Report and Written Opinion dated Jan. 30, 2013; International Application No. PCT/US2012/061215; Applicant: Foundry Newco XII, Inc.; 11 pages.

International Search Report and Written Opinion dated Jan. 30, 2013; International Application No. PCT/US2012/061219; Applicant: Foundry Newco XII, Inc.; 9 pages.

International Search report and Written Opinion for International App. No. PCT/US2005/044543, dated May 22, 2007, 8 pages.

International Search Report and Written Opinion for International App. No. PCT/US2014/014704, mailed Sep. 4, 2014, 18 pages.

Isner et al., "Contrasting Histoarchitecture of calcified leaflets from stenotic bicuspid versus stenotic tricuspid aortic valves," J Am Coll Cardiol., vol. 15, No. 5, p. 1104, (Apr. 1990).

Mohler, "Mechanisms of Aortic Valve Calcificaion," Am J Cardiol, vol. 94 No. 11, pp. 1396-1402, A6 (Dec. 1, 2004).

Non Final Office Action for U.S. Appl. No. 11/299,246, Mailed Apr. 7, 2009, 6 pages.

Non Final Office Action for U.S. Appl. No. 11/299,246, Mailed Oct. 16, 2008, 7 pages.

Non Final Office Action for U.S. Appl. No. 11/299,246, Mailed Aug. 22, 2007, 4 pages.

Non Final Office Action for U.S. Appl. No. 12/870,270, Mailed Nov. 18, 2011, 9 pages.

Non Final Office Action for U.S. Appl. No. 13/329,083, Mailed Jul. 25, 2013, 16 pages.

Non Final Office Action for U.S. Appl. No. 13/842,785, Mailed Feb. 3, 2014, 24 pages.

Non Final Office Action for U.S. Appl. No. 13/946,552, Mailed Feb. 3, 2014, 23 pages.

Non Final Office Action for U.S. Appl. No. 13/946,628, Mailed Feb. 4, 2014, 24 pages.

Non Final Office Action for U.S. Appl. No. 13/949,098, Mailed Feb. 24, 2014, 28 pages.

Notice of Allowance for U.S. Appl. No. 11/299,246, Mailed May 27, 2010, 6 pages.

Sakata et al., "Percutaneous Balloon Aortic Valvuloplasty: Antegrade Transseptal vs. Conventional Retrograde Transarterial Approach," Catheter Cardiovasc Interv., vol. 64, No. 3, p. 314, (Mar. 2005).

Sasaki et al., "Scanning electron microscopy and Fourier transformed infrared spectroscopy analysis of bone removal using Er:YAG and CO2 lasers" J Periodontol.; vol. 73, No. 6, pp. 643-652. (Jun. 2002).

(56) References Cited

OTHER PUBLICATIONS

Verdaadadonk et al., "The Mechanism of Action of the Ultrasonic Tissue Resectors Disclosed Using High-Speed and Thermal Imaging Techniques," SPIE, vol. 3594, pp. 221-231 (Jan. 1999).

Voelker et al., "Inoperative Valvuloplasty in Calcific Aortic Stenosis: a Study Comparing the Mechanism of a Novel Expandable Device with conventional Balloon Dilation," Am Heart J. vol. 122 No. 5, pp. 1327-1333 (Nov. 1991).

Waller et al., "Catheter Balloon Valvuloplasty of Stenotic Aortic Valves, Part II: Balloon Vavluloplasty During Life Subsequent Tissue Examination," Clin Cardiol., vol. 14 No. 11, pp. 924-930, (Nov. 1991).

Wang, "Balloon Aortic Valvuloplasty," Prog Cardiovasc Dis., vol. 40, No. 1, pp. 27-36. (Jul.-Aug. 1997).

Yock et al, "Catheter-Based Ultrasound Thrombolysis," Circulation, vol. 95 No. 6, pp. 1411-1416 (Mar. 18, 1997).

\* cited by examiner

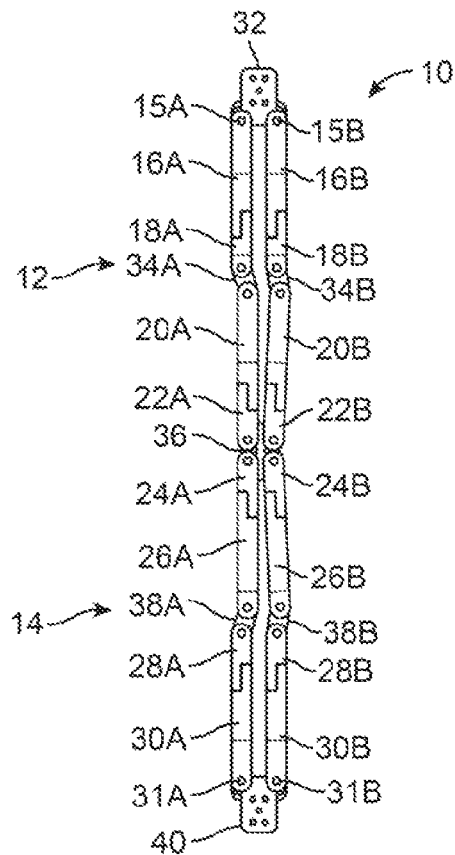
FIG. 2A
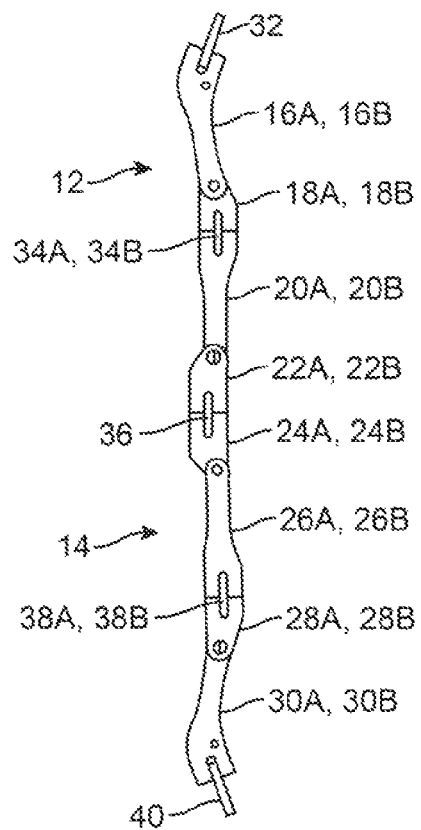
FIG. 2B
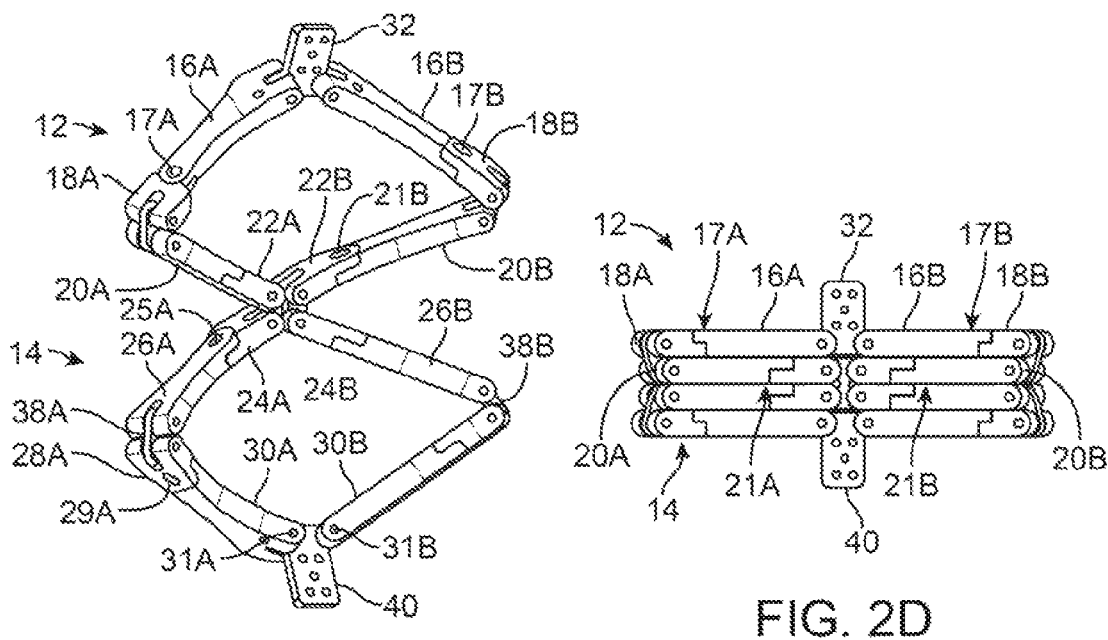
FIG. 2C
FIG. 2D

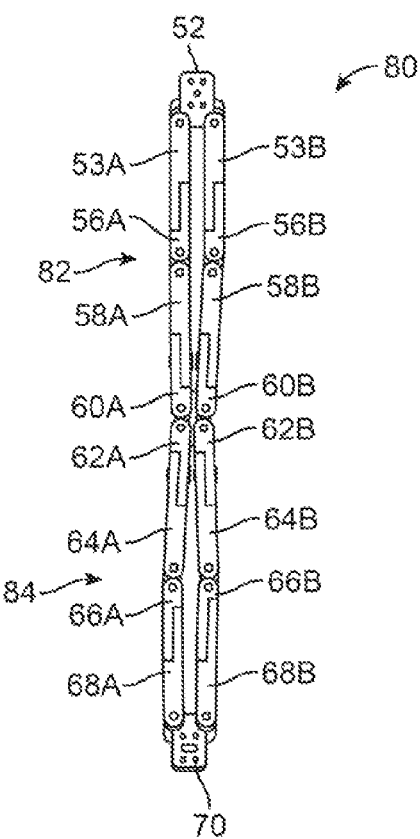
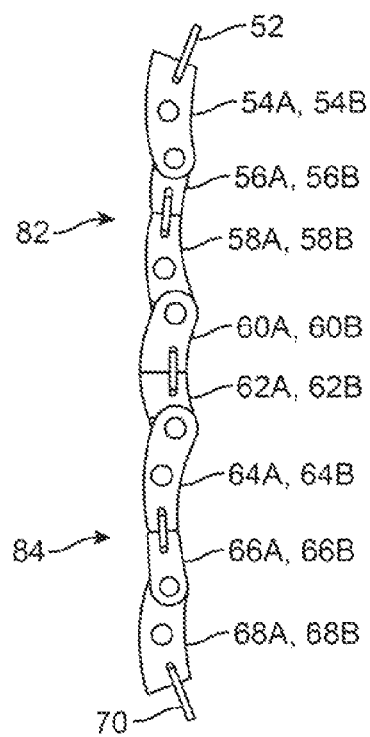
FIG. 3A
FIG. 3B
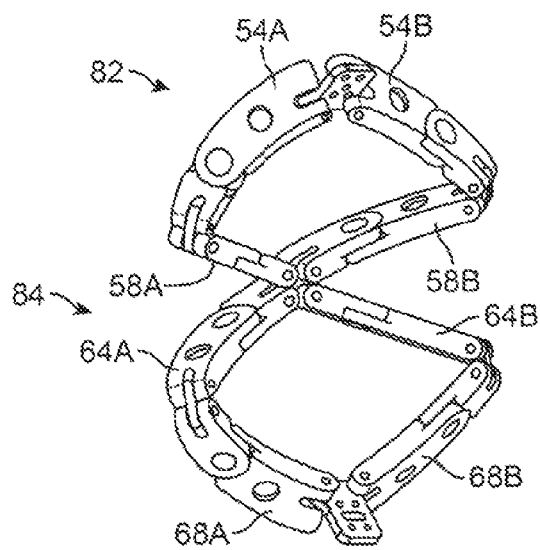
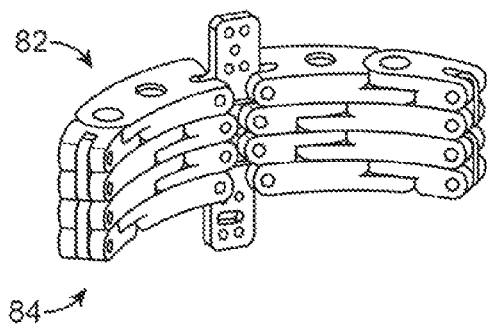
FIG. 3C
FIG. 3D

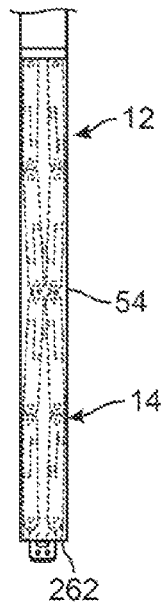
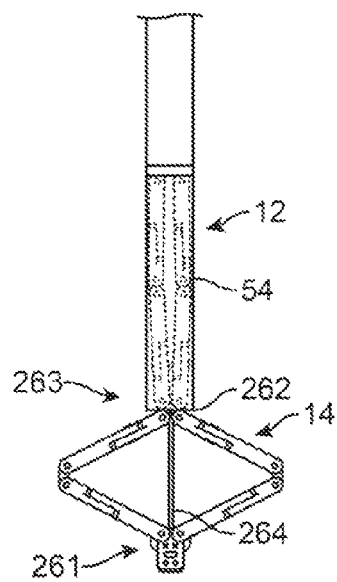
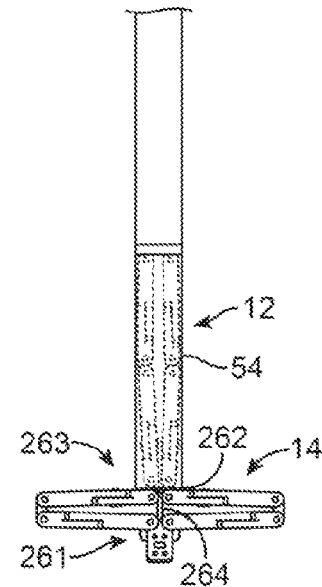
FIG. 17A　　　　FIG. 17B　　　　FIG. 17C
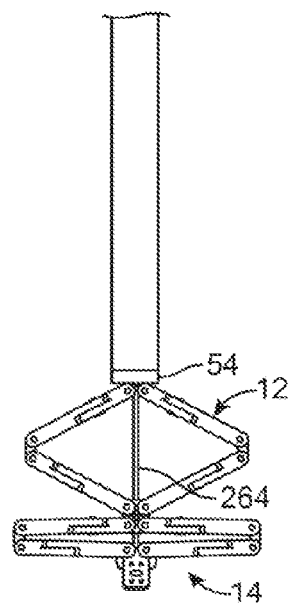
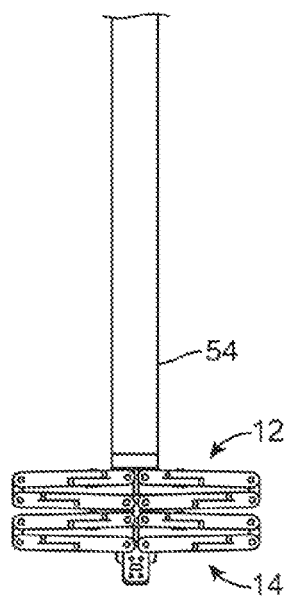
FIG. 17D　　　　FIG. 17E

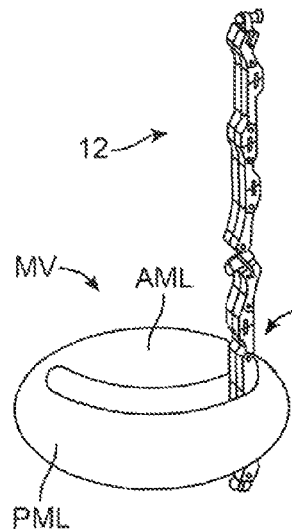 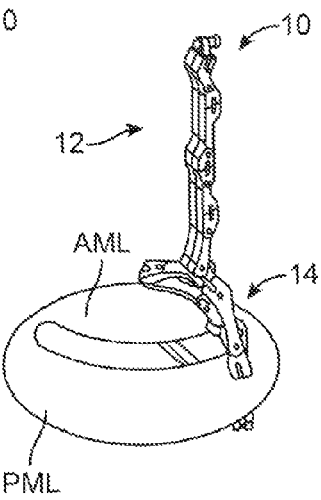 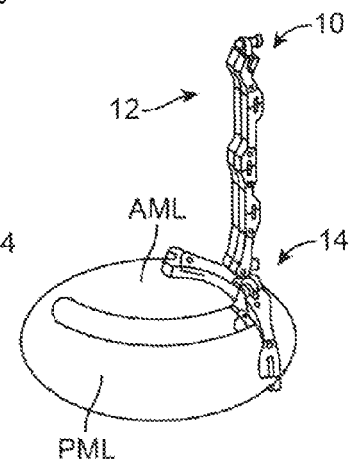
FIG. 18A  FIG. 18B  FIG. 18C
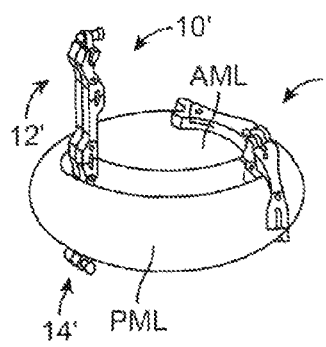 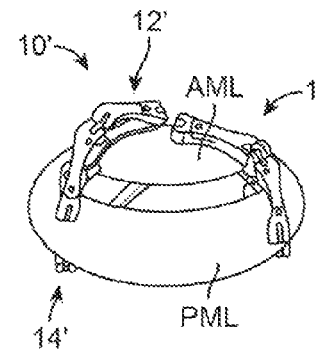 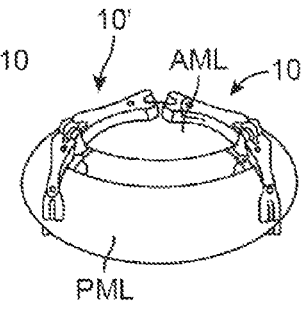
FIG. 18D  FIG. 18E  FIG. 18F
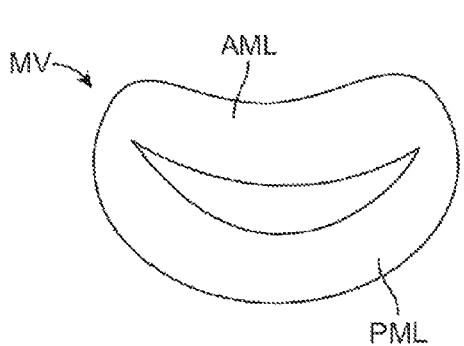 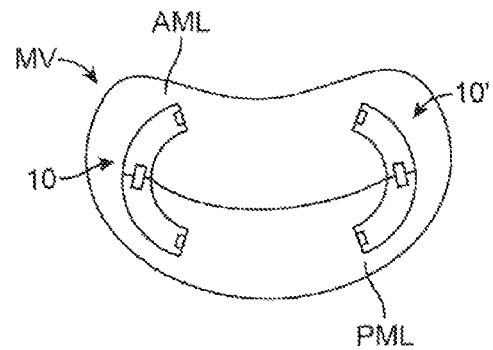
FIG. 19A  FIG. 19B

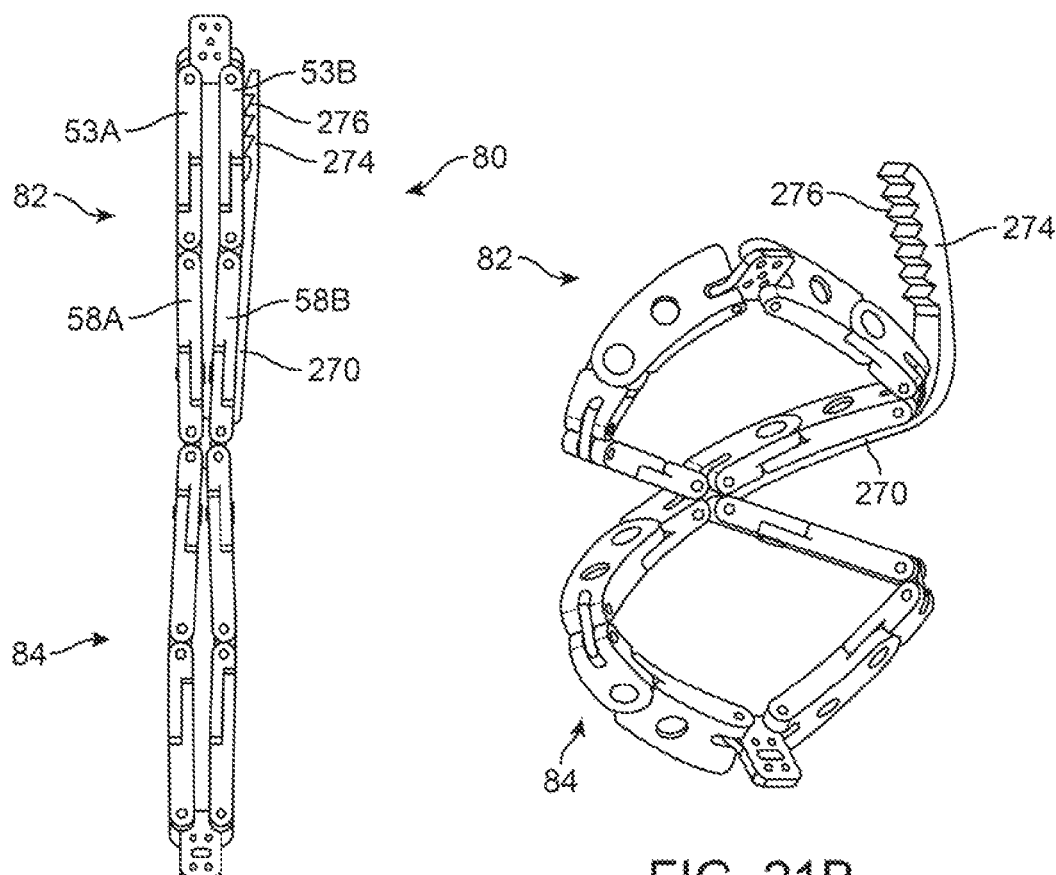
FIG. 21A
FIG. 21B
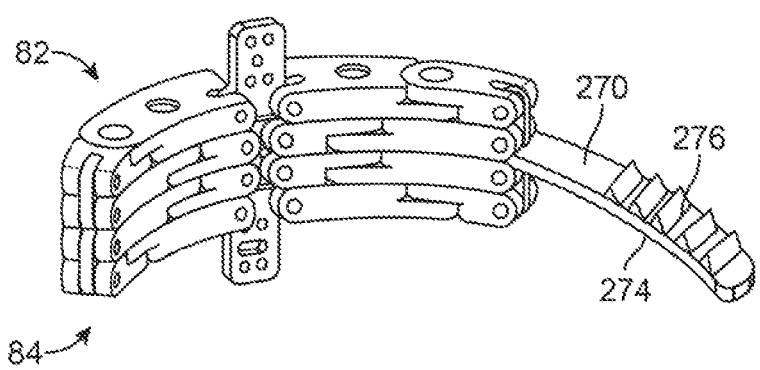
FIG. 21C

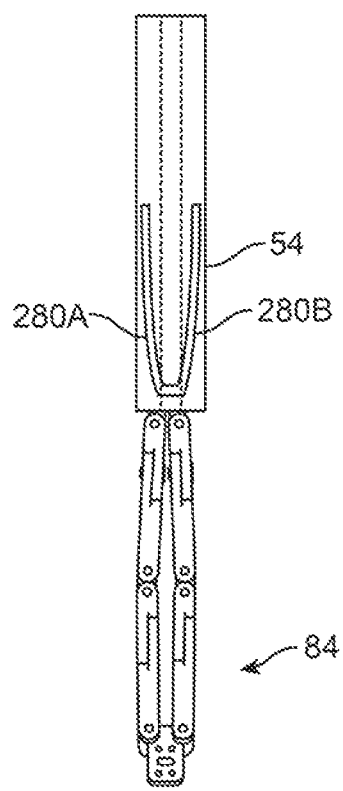
FIG. 23A
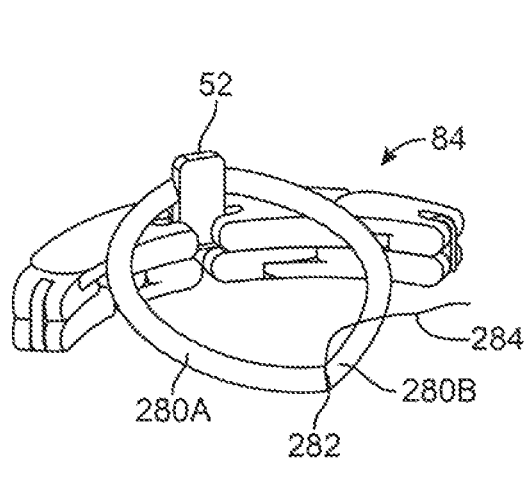 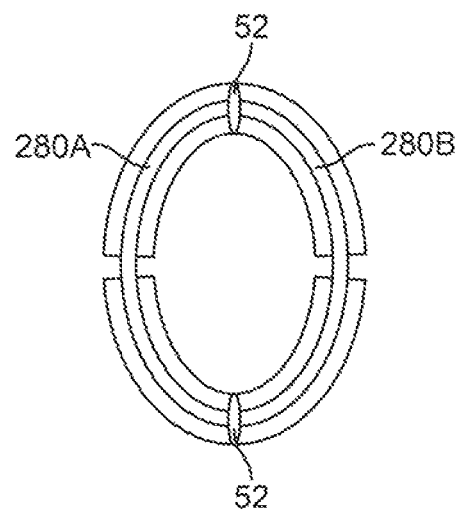
FIG. 23B          FIG. 23C

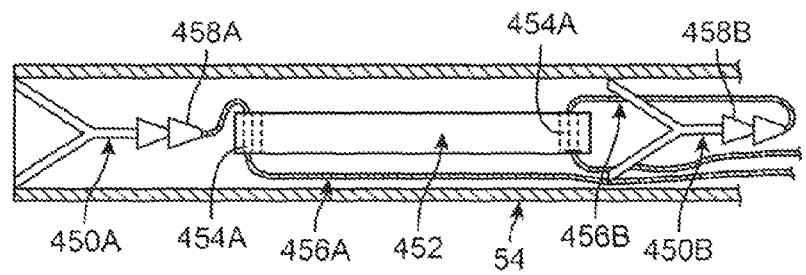
FIG. 43A
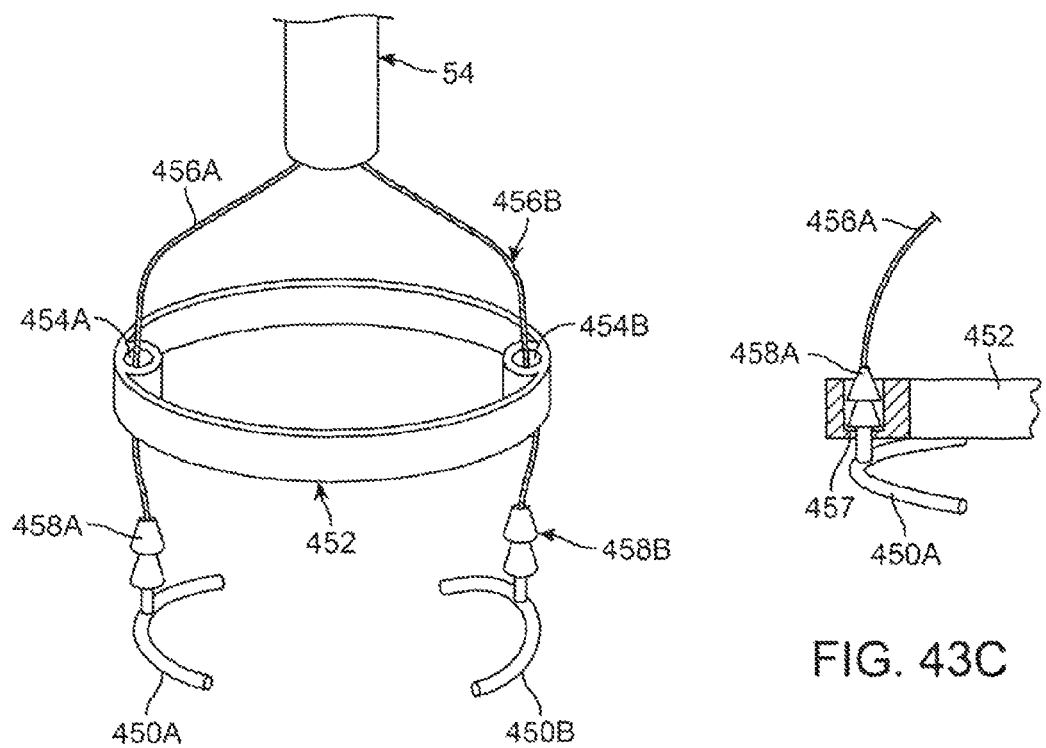
FIG. 43B
FIG. 43C

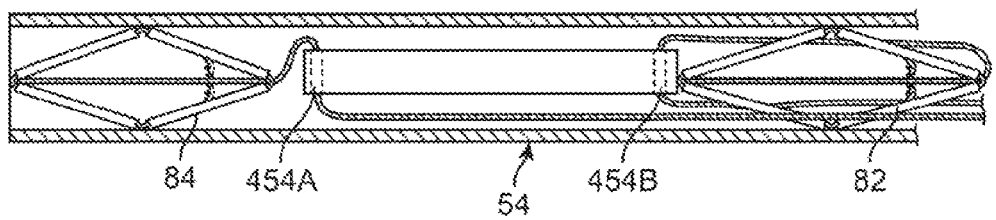
FIG. 45A
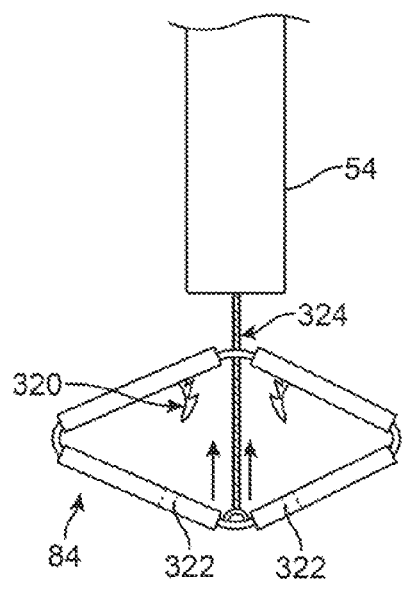 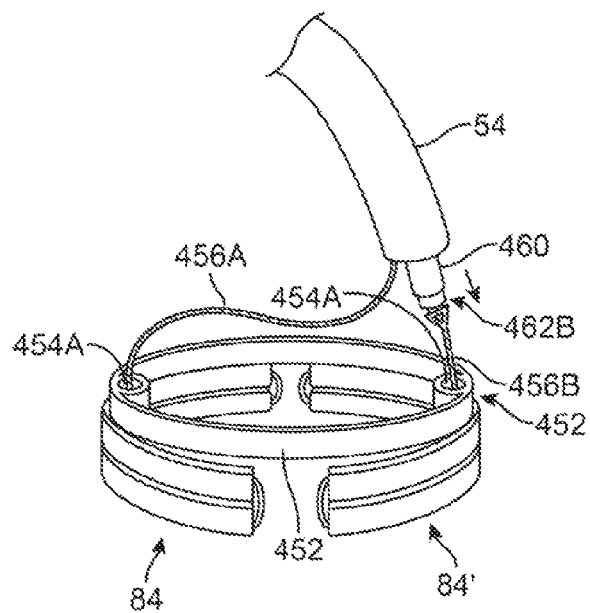
FIG. 45B                FIG. 45C

SYSTEM FOR MITRAL VALVE REPAIR AND REPLACEMENT

CROSS-REFERENCE TO RELATED APPLICATIONS

This application is a Division of and claims the benefit of priority from U.S. patent application Ser. No. 13/329,083, filed Dec. 16, 2011, now U.S. Pat. No. 9,421,098, issued on Aug. 23, 2016, which claims the benefit of priority of U.S. Prov. Pat App. Nos. 61/460,041 filed Dec. 23, 2010 and 61/499,630 filed Jun. 21, 2011, each of which are incorporated herein by reference in their entirety.

FIELD OF THE INVENTION

The present invention relates generally to medical devices used for the repair of dysfunctional heart valves. More particularly, the present invention relates to devices and methods used for the repair and/or replacement of the mitral valve.

BACKGROUND OF THE INVENTION

Conditions affecting the proper functioning of the mitral valve include, for example, mitral valve regurgitation, mitral valve prolapse and mitral valve stenosis. Mitral valve regurgitation is a disorder of the heart in which the leaflets of the mitral valve fail to coapt into apposition at peak contraction pressures, resulting in abnormal leaking of blood from the left ventricle into the left atrium. There are a number of structural factors that may affect the proper closure of the mitral valve leaflets. For example, many patients suffering from heart disease experience dilation of the heart muscle, resulting in an enlarged mitral annulus. Enlargement of the mitral annulus makes it difficult for the leaflets to coapt during systole. A stretch or tear in the chordae tendineae, the tendons connecting the papillary muscles to the inferior side of the mitral valve leaflets, may also affect proper closure of the mitral annulus. A ruptured chordae tendineae, for example, may cause a valve leaflet to prolapse into the left atrium due to inadequate tension on the leaflet. Abnormal backflow can also occur when the functioning of the papillary muscles is compromised, for example, due to ischemia. As the left ventricle contracts during systole, the affected papillary muscles do not contract sufficiently to effect proper closure.

Mitral valve prolapse, or when the mitral leaflets bulge abnormally up in to the left atrium, causes irregular behavior of the mitral valve and may also lead to mitral valve regurgitation. Normal functioning of the mitral valve may also be affected by mitral valve stenosis, or a narrowing of the mitral valve orifice, which causes impedance of filling of the left ventricle in diastole.

Typically, treatment for mitral valve regurgitation has involved the application of diuretics and/or vasodilators to reduce the amount of blood flowing back into the left atrium. Other procedures have involved surgical approaches (open and intravascular) for either the repair or replacement of the valve. For example, typical repair approaches have involved where the leaflets of the valve are either made to cinch or portions of the dilated annulus are resected.

Cinching of the annulus has been accomplished by the implantation of annular or peri-annular rings which are generally secured to the annulus or surrounding tissue. Other repair procedures have also involved cinching or clipping of the valve leaflets into partial apposition with one another as well. Alternatively, more invasive procedures have involved the replacement of the entire valve itself where mechanical valves or biological tissue are implanted into the heart in place of the mitral valve. These are conventionally done through large open thoracotomies and are thus very painful and require long recovery periods.

However, with many repair and replacement procedures the durability of the devices or improper sizing of annuloplasty rings or replacement valves may result in additional problems for the patient. Moreover, many of the repair procedures are highly dependent upon the skill of the cardiac surgeon where poorly or inaccurately placed sutures may affect the success of procedures.

Mitral valve replacement, compared with aortic valve replacement, poses unique anatomical obstacles, rendering percutaneous mitral valve replacement significantly more involved and challenging than aortic. First, unlike the relatively symmetric and uniform aortic valve, the mitral valve annulus has a non-circular oval or kidney-like shape, and may be of unpredictable geometry, often times lacking symmetry. Such unpredictability makes it difficult to design a mitral valve prosthesis having the ability to conform to the mitral annulus. Lack of a snug fit between the leaflets and/or annulus and the prosthesis leaves gaps therein, creating backflow of blood through these gaps. Placement of a cylindrical valve prostheses, for example, may leave gaps in commissural regions of the native valve, potentially resulting in perivalvular leaks in those regions, In addition to its irregular, unpredictable shape, the mitral valve annulus lacks a significant amount of radial support from surrounding tissue. The aortic valve, for example, is completely surrounded by muscular tissue, helping to anchor a prosthetic valve by providing native structural support. The mitral valve, on the other hand, is bounded by muscular tissue on the outer wall only. The inner wall of the mitral valve is bounded by only a thin wall of tissue separating the mitral valve annulus from the inferior portion of the aortic tract. As a result, significant radial forces on the mitral annulus, such as that imparted by expanding stent prostheses, could lead to collapse of the inferior portion of the aortic tract with potentially fatal consequences.

The chordae tendineae of the left ventricle may also present an obstacle in deploying a mitral valve prosthesis. This is unique to the mitral valve since aortic valve anatomy does not include chordae. The maze of chordae in the left ventricle makes navigating and positioning a deployment catheter that much more difficult in mitral valve replacement and repair. Deployment and positioning of a prosthetic valve or anchoring device on the ventricular side of the native valve is also complicated by the presence of the chordae.

Given the difficulties associated with current procedures, there remains the need for simple, effective, and less invasive devices and methods for treating dysfunctional heart valves.

SUMMARY OF THE INVENTION

An interventional device may be advanced intravascularly into the heart of a patient and deployed upon or along the mitral valve to stabilize the valve leaflets. The interventional device may also facilitate the placement or anchoring of a prosthetic mitral valve implant in an efficient manner. The interventional device may generally comprise a subannular set of arms pivotably and/or rotatably coupled to a supra-annular set of arms. The distal set of arms may be advanced past the catheter opening to a subannular position (e.g., below the annulus of the mitral valve and behind the native leaflets) and reconfigured from a low-profile delivery configuration to a deployed securement configuration. The proximal arm members may then also be deployed such that the distal and proximal arm members, once fully deployed, may grip the leaflets and/or the annulus between the two sets of arms to stabilize the leaflets. In either case, the arm members may be deployed either sequentially or simultaneously depending upon the desired order of deployment.

When the proximal and distal stabilizing assemblies are actuated to reconfigure from their axially-elongated low-profile configuration, the assemblies may reconfigure into a deployed expanded configuration where the pivoting arrangements of each arm and joining member allows the assemblies to extend radially in a jack-like configuration to a deployed configuration. In the deployed configuration, each of the arm members may pivot to collapse the arm members in a radial direction relative to a longitudinal axis of the assembly against the side surfaces of an adjacent arm member assembly such that the resulting deployed shape of the arm members may form a curved or partially curved configuration which may follow along a periphery of the mitral valve.

In one example for delivering and deploying one or more interventional devices, the devices may be deployed from a supra-annular approach from within left atrium of the heart H or from a subannular approach from within the left ventricle. Moreover, one or more interventional devices may be deployed in or near one or both valve commissures with the deployed arm members compressing the leaflets therebetween, stabilizing a portion of the valve leaflets while allowing the remainder of the leaflet(s) to move in an uninhibited fashion. While the one or more interventional devices may be utilized alone, a stent, scaffold, or replacement valve assembly may optionally used as well in combination with the one or more assemblies. The valve assembly may be expanded and optionally anchored to the stabilizing assemblies such that the valve assembly extends above, below, or entirely through the mitral valve.

Once the interventional device has been delivered and/or expanded into its deployed configuration, the device may be locked into its deployed shape and left implanted upon or along the mitral valve. To ensure that the device remains secured upon the valve leaflets, various locking mechanisms may be incorporated into the device. For example various locking mechanisms such as, e.g., screw threads, gripping element with a release wire, or other suitable attachment mechanisms may be used.

In yet another variation, one or more of the arm members themselves may be formed of multiple links or segments which increase the flexibility of the device. The arm members formed of the links or segments may provide for increased flexibility of the assemblies when placed against the leaflets. Having the increased flexibility may allow for the interventional device to more closely conform to a particular anatomy of a valve and may further provide for enhanced support of the valve.

Additionally and/or alternatively, one or all of the arm members may have rounded or curved edges to facilitate delivery of the device through the catheter as well as to reduce any potential wear against the internal catheter surface. For example, if a delivery catheter having a 6 mm internal diameter, each respective arm member may have a cross sectional width, e.g., of about 5 mm and a height, e.g., of about 2 mm. Having the curved edges may allow for the translation of the device through the catheter lumen without wearing along the lumen surfaces. Moreover, the curved surfaces and edges of each arm member may also reduce any potential wear on the contacted mitral leaflets as well.

In any of the variations of the interventional devices described herein, various features or projections such as pins, castellations, raised tabs, or any other projections, protrusions, bumps, or features which may facilitate engagement with a replacement mitral valve implant may be formed along one or more arm members. These features may be located along the surface of the arm members which face the central region of the mitral valve when deployed.

Additionally and/or alternatively, these various features or projections may also be defined along the surfaces of the arm members which come into direct contact against the mitral valve leaflets. For example, the arm members of both proximal and distal stabilizing assemblies which extend into contact against the surfaces of the mitral leaflets may also incorporate various features. Examples shown may include projections, tabs, or pins which may simply compress upon the opposed surfaces of the mitral leaflets or they may be correspondingly designed to interdigitate or lock in an alternating pattern with respect to opposed features or projections when brought down upon the mitral leaflets into a locking configuration. Moreover, such features or projections may be covered by a fabric or covering, such as a kitted sleeve, to present a relatively atraumatic surface.

In yet another variation, the arm members may be further varied by incorporating narrowed or tapered arms that may reduce any risk of perivalvular leakage in the space between the arms, if any. Alternatively, the stabilizing assemblies may incorporate narrowed or tapered arms which die directly into the posterior wall of the mitral valve such that any replacement valve may directly contact against the posterior wall without any gaps.

Another variation of the arm members may incorporate extensions which may extend linearly out or may fold out from the posterior set of arms to fill in any gaps along the posterior leaflet. The extensions may optionally extend partially or may lock with respect to an apposed extension. Yet another variation may incorporate a coupling mechanism such as a sliding suture lock which may be advanced over wires or sutures extending from the anus of multiple assemblies to create a rigid or secure connection between each of the implanted assemblies in their deployed configurations upon the valve leaflets.

Yet another variation may include arm members which may be configured in an alternative arrangement where the distal stabilizing structure may be configured to have deployed arm members which are relatively shorter than the deployed arm members of the proximal stabilizing structure to facilitate deployment of the distal stabilizing structure without interfering with the chordae tendineae or papillary muscles found within the left ventricle. The lengths of the shortened distal stabilizing arm members may vary along any range and may also be configured to be relatively longer than the arms of the proximal stabilizing structure in yet other variations.

With respect to locking mechanisms, various types of mechanisms may be utilized to lock the interventional device into its deployed configuration. The interventional device may incorporate one or more respective locking mechanisms (e.g., pins, ratchets, crimps, collars, threaded fasteners, rivets, knotted tensioning loops, etc.) positioned along a side surface of the arm members such that the locking mechanisms are received into respective receiving channels defined along apposed arm members when reconfigured into the deployed configuration. As previously described, a tensioning wire, suture, or catheter may be coupled to a distal end of the interventional device such that when tensioned, the device may reconfigure into a laterally-elongated, deployed configuration. Also, as the arm members fold into their deployed shape, the locking mechanisms may be received into their respective receiving channels and locked automatically to secure the arm members into their deployed configurations.

In yet additional variations, rather than the proximal interventional device being modified, the distal interventional device may be modified as well. One variation may include a telescoping assembly which may be deployable in the sub-annular space below the plane upon the ventricular side of the mitral valve. The telescoping assembly may be comprised of telescoping arms which are attached to a pivoting assembly which may be used to position the arms from a low-profile extended configuration to an angled deployed configuration. Once positioned for extension, one or more telescoping members may extend linearly at an angle relative to one another (acute, right, or obtuse depending upon the desired configuration) from each arm. Alternatively, the telescoping members may extend in a curved or arcuate manner to form curved arm member when deployed. In yet another configuration, one telescoping arm may extend linearly while the opposite arm extends to form a curved deployed arm. Having the arms telescope outward may avoid entanglement with various ventricular obstructions such as the chordae tendineae and/or papillary muscles. With the arms fully extended, the proximal stabilizing structure may then be deployed for securement upon the upper leaflet surfaces.

Another variation may also utilize two or more arms which may project linearly from a catheter and extend perpendicularly or at an angle relative to the catheter to form a curved arm along a supravalvular position upon the upper leaflet surface or surfaces as well as along a subvalvular position along a lower leaflet surface or surfaces. Alternatively and/or additionally, the arms may be advanced for positioning upon or adjacent to the anterior and posterior annulus.

The two or more arms may project through corresponding openings which are adjacently positioned along the catheter and in one variation, two proximal arms may extend from the catheter along a supravalvular position while two additional distal arms may extend from the catheter along a subvalvular position to at least partially compress or stabilize the valve leaflets between the proximal and distal pair of arms.

After locating or situating the assembly at the level of one or both mitral commissures or in other gaps between the segments of the mitral leaflets, the assembly provides the passage of supravalvular arms and subvalvular arms which may be placed at least partially or completely circumferentially above and below the anterior and posterior annulus or upon the valve leaflets. The apparatus may then be used to provide a platform for the placement and fixation of existing transcatheter and sutureless valve prostheses.

The arms may be constructed from various biocompatible materials sufficient to provide flexibility yet are rigid or semi-rigid enough to provide support to the valve leaflets, e.g., shape memory alloys, stainless steels, etc. Alternatively, the arm members may be constructed so as to form inflatable tubular structures that may have rigidity induced by an inflation gas, fluid, or other medium (e.g., saline, water, etc.) introduced into the arm structures at a sufficiently high pressure. Alternatively, the rigidity along the arm members may be induced by inflating the arms with a hardening fluid which is liquid when introduced but which hardens or solidifies after filling the arm members. Additionally and/or alternatively, the arm members may have any number of frictional components or projections (barbs, spikes, etc., or any of the projections or elements described herein) formed upon the contact surfaces of the arm members to increase the fixation between the arms and the underlying tissue.

Moreover, the length of the arm members may be varied to extend about the periphery of the valve annulus partially or entirely around the periphery to overlap upon themselves. Alternatively, a second assembly may be used in combination with a first assembly such that each assembly is positioned and deployed at opposed ends of the valve. Each of the assemblies may have their arm members extended towards one another to increase annular rigidity.

In yet another variation of the interventional device, a supporting ring may be utilized in combination with one or more retaining members rather than with a interventional device. A prosthetic supra-annular ring may be shaped or sized similarly to a periphery of the mitral valve and may also support an implanted prosthetic valve. One or more openings may also be defined at either end of the ring along the circumference to provide guidance for wire or sutures which may pass through each respective opening. The couplings may be attached to respective wire or suture such that the couplings may be received within the respective openings defined through the ring in a locking manner when each wire or suture is tensioned to secure a position of each respective retainer member relative to the ring. The couplings may define one or more tapered members which allow for their insertion into and/or through the openings which inhibit their retraction or withdrawal to allow for adjustable securement of the ring and retainer members upon the mitral valve annulus. Alternatively, various other mechanisms such as ratcheting teeth, pawls, spherical locking elements, hitch/ring assembly, etc. may be used.

Another variation of the interventional devices(s) include at least two independently deployable structures positionable in a sub-annular space and configured to engage a subannular surface of the mitral valve when deployed. The independently deployable structures may be positioned at any point along the annulus, e.g. on opposing sides of the valve, in the valve commissures, etc. Likewise, the at least two independently deployable structures may be interconnected, as described herein. Furthermore, the device may include a prosthetic valve coupleable to the at least two independently deployable structures.

The interventional device(s) may also comprise a stabilizing structure movable between a first configuration and a second configuration. In the first configuration the stabilizing structure(s) are positionable between the leaflets. The first configuration may assume a variety of forms, including, for example, a flexible, linear configuration and/or an axially-elongated configuration. In the first configuration the stabilizing structure(s) may be positionable between the leaflets of the mitral valve into a subannular space. In the second configuration, the stabilizing structure is configured to engage a ventricular surface of the valve and/or leaflets. Like the first configuration, the second configuration may assume a variety of forms, including a curved configuration which may approximate the shape of the native valve annulus. Furthermore, the device may include a prosthetic valve coupleable to the at least two independently deployable structures.

The device may also include a first and second stabilizing structure positionable in a subannular space of the heart valve. A prosthetic valve may be coupleable to the stabilizing structures.

In yet another variation, the interventional devices(s) may include a first portion of the device which is positionable in a subannular space as well as a second portion of the device positionable in a supra-annular space. The first portion may also include two laterally extending wings positionable in the subannular space, where the laterally extending wings are capable of collapsing to a linear, flexible configuration and also a laterally-elongated, rigid configuration. Furthermore, the first portion and second portion may compress a mitral leaflet(s) and/or annulus therebetween. The second portion may be detachable from the first portion. In addition, a flexible tether may be coupled to the first or subannular portion of the device. Likewise, the device may include a coupling mechanism for coupling the first portion to the second portion at the native valve site when the second portion is positioned in the subannular space.

BRIEF DESCRIPTION OF DRAWINGS

FIGS. 2A and 2B show front and side views, respectively, of one variation of an interventional device in its low-profile axially-elongated delivery configuration.

FIG. 2C shows a perspective view of the interventional device in a partially expanded configuration where a proximal stabilizing structure and a distal stabilizing structure are partially reconfigured.

FIG. 2D shows a side view of the interventional device in its deployed configuration for placement along and upon the valve.

FIGS. 3A to 3D illustrate front and perspective views of another variation of the interventional device incorporating extension members optionally having an engagement feature defined along the extension member for adjustable securement with a corresponding extension member.

FIGS. 17A to 17E illustrate side views of another variation where the proximal and distal stabilizing structures may be deployed and reconfigured in sequence.

FIGS. 18A to 18F illustrate perspective views of one example where a first interventional device may be deployed and secured at a first end of the mitral valve and where a second interventional device may be deployed and secured at a second end of the mitral valve such that each interventional device may curve around a periphery of the valve.

FIGS. 19A and 19B illustrate top views of a defective mitral valve where the posterior and anterior mitral leaflets fail to coapt and how the interventional devices may be positioned along the leaflets at opposed ends of the valve to facilitate coaptation of the leaflets.

FIGS. 21A to 21C illustrate side and perspective views of an interventional device having a respective extension member.

FIGS. 23A and 23B illustrate front and perspective views of another variation where the interventional device may incorporate curved stabilizing arms which may extend over the leaflet into securement with one another.

FIG. 23C illustrates a top view of an interventional device with curved stabilizing arms.

FIGS. 30A to 31B illustrate partial cross-sectional side views of other examples of crimped locking mechanisms which may be utilized to lock the interventional device.

FIGS. 43A to 43C illustrate side and perspective views of another variation of an interventional device utilizing one or more subannular stabilizing members with a supra-annular ring.

FIGS. 45A to 45E illustrate another variation of an interventional device utilizing a distal stabilizing structure with a supra-annular ring

DETAILED DESCRIPTION OF THE INVENTION

Figure 1:
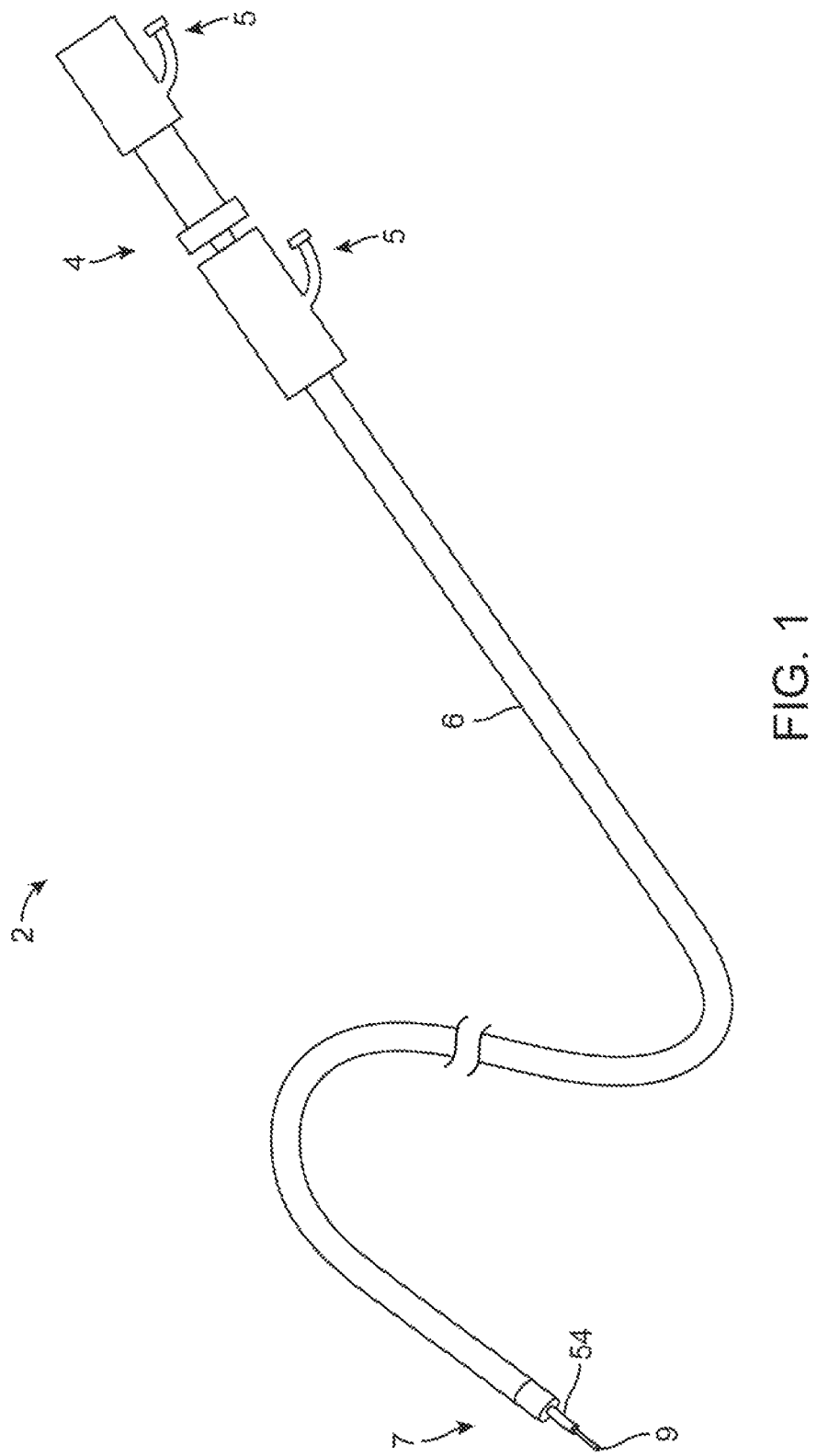
FIG. 1 shows a perspective view of one variation of a catheter assembly for intravascularly delivering and deploying an interventional device.

In repairing and/or replacing a defective heart valve, such as a mitral valve, an interventional device may be advanced intravascularly into the heart of a patient and deployed upon or along the mitral valve to affect the abnormal functioning of the valve leaflets. The interventional device may also facilitate the placement or anchoring of a prosthetic mitral valve implant in an efficient manner. In one variation, the interventional device may generally comprise a distal stabilizing structure 14 pivotably and/or rotatably coupled to a proximal stabilizing structure 12. The distal stabilizing structure 14 may be advanced past the catheter opening, through the mitral annulus, and reconfigured from a low-profile, axially-elongated delivery configuration, as shown in FIG. 2A, to a laterally-elongated deployed configuration, as shown in FIG. 2C. Deployment of the distal stabilizing structure may result from the urging of a biasing element, such as a torsion spring, and/or the tensioning of a control member such as a suture or wire. The proximal stabilizing structure 12 may also be deployed, either sequentially (as shown in FIGS. 18A-18F) or simultaneously with the distal stabilizing structure 14 (as shown in FIG. 1C), such that the distal and proximal stabilizing structures 12, 14 may grip the leaflets and/or annulus between the two valve assemblies 12, 14 in order to stabilize the leaflets and/or to provide a stable platform to which a prosthetic valve may be anchored.

As used herein, the terms "distal" and "proximal" are relative to the catheter assembly 2 along the axis of the catheter assembly 2. For example, the distal end of the guidewire 9 is farther from the handle 4 of the catheter assembly 2 and the proximal end of the guidewire 9 is the portion of the guidewire 9 closer to the handle 4 of the catheter assembly 2.

As used herein, "stabilizing structure" may refer to a structure placed above, below, along, or within the annulus, and may take a conformation encompassing the entire circumference of the annulus or a partial circumference of the annulus.

As used herein, depending on the intravascular approach utilized (e.g., retrograde, antegrade, etc.) the distal and proximal stabilizing structures may have varying orientations with respect to the mitral valve annulus. For example, the distal stabilizing structure may be positioned supra-annularly if the retrograde approach is utilized or may be positioned subannularly if the antegrade approach is utilized. Likewise, the proximal stabilizing structure may be positioned subannularly if the retrograde approach is utilized or may be positioned supra-annularly if the antegrade approach is utilized.

I. Device Embodiments

FIG. 1 illustrates a perspective view of one variation of a deployment catheter assembly 2 which may be used to intravascularly deliver and deploy the interventional device. Generally, the catheter assembly 2 may comprise a handle 4 which is coupled to a proximal end of a catheter shaft 6, e.g., 18 F-20 F diameter. Catheter shaft may include at least one catheter port(s) 5. A distal end 7 of the catheter may define an opening through which a guidewire 9 may be passed as well as a delivery shaft 6 which may be coupled to the interventional device for delivery and/or deployment from the catheter.

FIGS. 2A and 2B show the top and side views of one variation of the interventional device 10. The interventional device 10 may generally comprise a distal stabilizing structure 14 pivotably and/or rotatably coupled to a proximal stabilizing structure 12. In this variation, the proximal and distal stabilizing structures 12, 14 are illustrated as having similar or equal lengths although the respective lengths may be varied to be non-uniform depending upon the desired deployed configuration, as further described below.

FIGS. 2A and 2B show the interventional device 10 in a low-profile delivery configuration for storage and delivery from a catheter lumen. When the interventional device 10 is in its delivery configuration, both first and second stabilizing assemblies 12, 14 are in their axially-elongated configurations.

In the deployed configuration, each of the arm members may pivot to collapse the arm members in a lateral direction relative to a longitudinal axis of the assembly 10. Arm members may collapse against the side surfaces of adjacent arm members such that the resulting laterally-elongated shape of the arm members may form a curved or partially curved configuration which may follow along a periphery of the mitral valve annulus. For example, the deployed arm members may be formed to extend, over a 60° span. In this variation, deployment of the interventional device 10 transforms the arm members from a flexible linear arrangement into a rigid arc of fixed radius.

FIG. 2C shows one variation of the device in one variation of an intermediate configuration, or between the axially-elongated and laterally-elongated configurations. When the first and second stabilizing assemblies 12, 14 reconfigure from their axially-elongated configurations to their deployed laterally-elongated configurations, the pivoting arrangements of each arm member and joining member allows the arms and joining members to extend laterally in a jack-like fashion, as shown in the perspective view of FIG. 2C. The distal 14 and proximal 12 stabilizing structures may transform from the laterally-elongated configuration to the axially-elongated configuration independently, dependently, sequentially, simultaneously or any combination thereof. FIG. 2D shows the interventional device 10 in its deployed configuration, wherein both the proximal and distal stabilizing structures 12, 14 are in a laterally-elongated configuration.

The proximal stabilizing structure 12 may be comprised of a first pair of arm members 16A, 16B which are pivotably joined to a proximal engagement link 32 at a first end through joints 15A, 15B, and also pivotably joined to respective joining members 18A, 18B at a second end through joints 17A, 17B. While the first pair of arm members 16A, 16B may pivot around joints 15A. 15B within a first plane parallel to the broad face of link 32, the coupling at the second end may pivot around joints 17A, 17B within a second plane parallel to the broad face of the superior portion of arms 16A, 16B, which can be transverse (FIG. 2D) or angled (e.g., FIG. 2C) relative to the first plane. The joining members 18A, 18B may be further pivotably coupled to a first end of a second pair of arms 20A, 20B via respective links 34A, 34B which allow for pivotable movement in a third plane parallel to the broad face of links 34A, 34B. The second pair of arms 20A, 20B may be further coupled pivotably to joining members 22A, 22B such that the pivotable movement of the second ends of the second pair of arms 20A, 20B may occur around respective joints 21A, 21B within a fourth plane parallel to the superior portion of arms 20A, 20B. Joining members 22A, 22B may then be pivotably coupled to a middle engagement link 36 such that the pivotable movement of the second ends of the joining members 22A, 22B may occur around link 36 within a fifth plane parallel to the broad face of link 36.

The distal stabilizing structure 14 may be coupled similarly to the proximal stabilizing structure 12 where joining members 24A, 24B may be pivotably coupled to the middle engagement link 36 such that the pivotable movement of the joining members 24A, 24B may occur around link 36 within the fifth plane. Joining members 24A, 24B may be further pivotably coupled to a first end of a third pair of arms 26A, 26B such that the pivotable movement of the arms 26A, 26B may occur around joints 25A, 25B within a sixth plane parallel to the broad face of the superior portions of arms 26A, 26B. The second ends of arms 26A, 26B may be pivotably coupled to joining members 28A, 28B via links 38A, 38B where pivoting movement may occur within a seventh plane parallel to the broad face of links 38A, 38B. A first end of a fourth pair of arms 30A, 30B may be pivotably coupled to the joining members 28A, 28B around respective joints 29A, 29B, such that the pivotable movement of the first end of arms 30A, 30B is within an eighth plane parallel to the inferior faces of joining members 28A, 28B. The second end of each arm 30A, 30B may be pivotably coupled to distal engagement link 40 in a pivoting engagement which allows for pivoting motion around respective joints 31A, 31B within a ninth plane parallel to the broad face of link 40.

There are several advantages to utilization of multi-arm, multi-link assemblies. First, multi-arm, multi-link assembly provides for multiple planes of pivotal movement around multiple axes of rotation, allowing greater manipulation of the profile and shape of the interventional device 10, both in its delivery and deployed configuration. The flexibility of the interventional device 10 presents an advantage in that it may assume a linear, low-profile delivery configuration, shown, for example, in FIG. 2A, while remaining flexible enough to bend along the catheter lumen during delivery and/or deployment. Despite the flexibility of the interventional device 10, however, the presence of multiple links and arms also provides substantial rigidity once the interventional device 10 is in the fully deployed configuration, where each assembly is in its laterally-elongated configuration. Such rigidity may be provided by the offsetting of the arms and joining members within each layer of each annular structure. For example, in FIG. 2D distribution of arms and joining members is such that, once the distal stabilizing structure 14 is in the laterally-elongated configuration, first pair of arms 16A, 16B are no longer able to rotate around, for example, respective joints 17A, 17B since first pair of arms 16A, 16B straddles respective joints 21A, 21B. This is but one example of the interlocking mechanisms employed by the multi-arm, multi-link structure of each annular structure.

Each of the arm members and joining members may be made from any number of suitable biocompatible materials, e.g., stainless steel, various polymers, ELGILOY® (Elgin, Ill.), pyrolytic carbon, silicone, polytetrafluoroethylene (PTFE), or any number of other materials or combination of materials depending upon the desired results. The arm members may also be coated or covered with a material that promotes tissue in-growth, e.g., Dacron, PTFE, etc.

FIGS. 3A-3D illustrate another variation of the interventional device, where the arm and joining arm members have a more consistently arcuate shape along its periphery than the arms and joining members of interventional device 10. Interventional device 80 where each of the proximal and distal stabilizing structures 82, 84 may be formed of a first pair of arms 54A, 54B and joining members 56A, 56B and a second pair of arms 58A, 58B and joining members 60A, 60B each pivotably joined, as previously described, but where the arm members form a more uniform and curvilinear shape. Similarly, the distal stabilizing structure 84 may be coupled via a middle link and is formed of joining members 62A, 62B and a third pair of arms 64A, 64B and further by joining members 66A, 66B and a fourth pair of arms 68A, 68B each pivotably joined to one another. FIGS. 3C and 3D illustrate how the first and second assemblies 82, 84 may pivot along their respective links and pivoted connections to expand into a laterally-elongated configuration, shown in FIG. 3D.

Figure 4A:
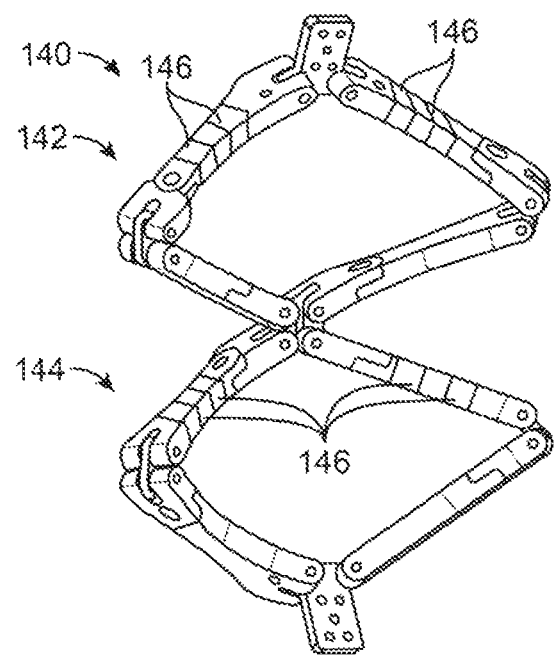
FIGS. 4A and 4B illustrate perspective and side views of another variation of a interventional device having arm members which are formed of segments or links which provide increased flexibility for conforming against the anatomy of the valve.
Figure 4B:
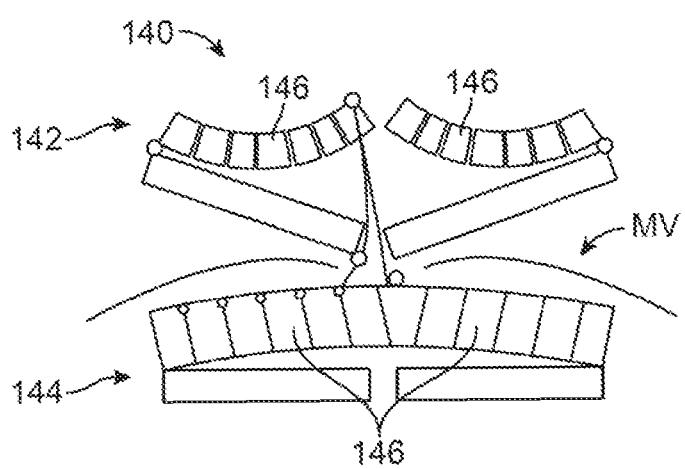

In yet another variation, one or more the arm members themselves may be formed of multiple links or segments coupled together in such a way so as to increase a flexibility of the assembly. An example is illustrated in the perspective and side views of FIGS. 4A and 4B. As shown, an interventional device 140 may have a proximal stabilizing structure 142 and a distal stabilizing structure 144 where at least some of the respective arm members are comprised of multiple small links or segments 146 linked together by flexible elongate couplings. The arm members formed of the links or segments 146 may provide for increased flexibility of the assemblies when placed against the leaflets. Having the increased flexibility may allow for the interventional device to more closely conform to a particular anatomy of a valve and may further provide for enhanced support of the valve and may require less clearance within the heart chambers for deployment.

Figure 5A:
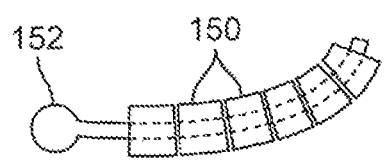
FIGS. 5A to 5C illustrate variations of the segmented or linked arm members which may be tensioned into a predefined curvature or shape.
Figure 5B:
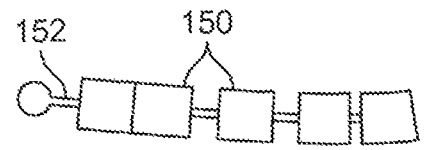
Figure 5C:
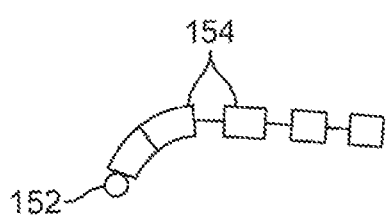

In other variations where the arm members are comprised of segmented arms, one or more of the arm members may have links or segments 150 which may become rigid by the tensioning of a pullwire 152 to maintain a particular shape of the arm member. As illustrated in the example of FIG. 5A, a pullwire 152 may extend through each of the links such that when tensioned the arm member may become rigid as the links 150 compress against one another and when released, allows the arm member to become flexible, as shown in FIG. 5B. Alternatively and/or additionally, the interfacing ends of the links or segments 154 may be preformed to have various angles or shapes such that when tensioned by pullwire 152, the arm member assumes a predetermined shape, as shown in FIG. 5C.

Figure 6:
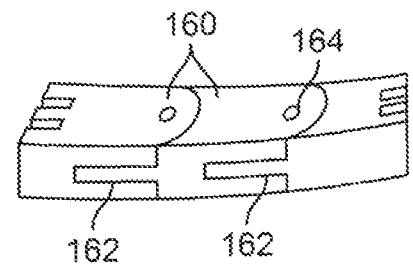
FIG. 6 shows a perspective views of yet another variation of segmented or linked arm members which may be coupled via pivots.
Figure 7A:
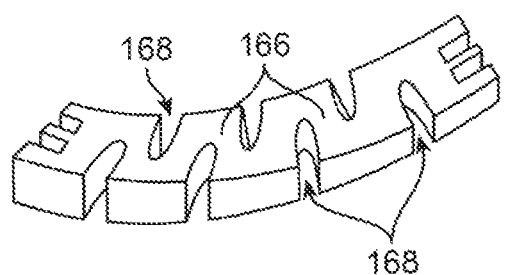
FIGS. 7A and 7B show perspective views of yet another variation of segmented or linked arm members which may be formed into a single undulating pattern.
Figure 7B:
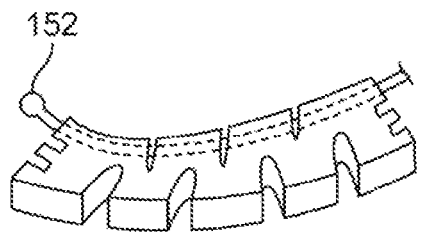

In yet other variations with segmented arm members, one or more of the arm members may be formed as links or segments 160 coupled via slotted connections 162 which are rotatably hinged 164 to allow for bending in a single plane but provides for stiffness in a transverse plane, as shown in FIG. 6. Alternatively, the links or segments 160 may be hinged in an alternating manner to allow for differential bending of the structure. Yet another variation is shown in the perspective view of FIG. 7A which illustrates an arm member which is formed of a patterned member 166 such as an undulating pattern formed by molded or machined portions 168 removed from the arm member. Such a configuration may also allow for differential bending of the structure such that flexibility against a leaflet surface may be provided while maintaining a degree of structural stiffness along another plane. A pullwire 152 may be passed through a lumen extending through the length of the arm member such that by tensioning the wire 152 the arm member will bend into a desired shape, as shown in FIG. 7B.

Figure 8:
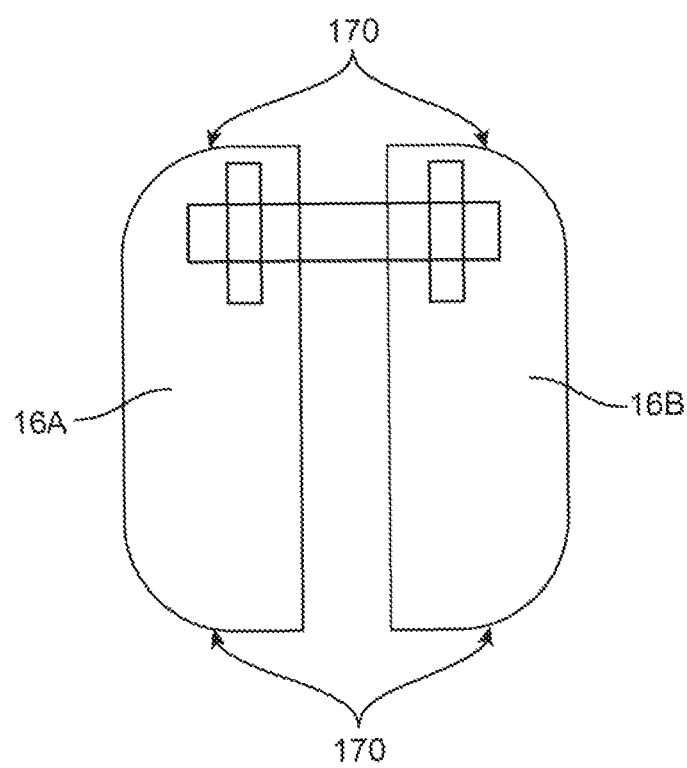
FIG. 8 illustrates an end view of arm members which may be formed to have curved or rounded edges to facilitate deployment from the catheter as well as reduce any potential wear against tissue.

Additionally and/or alternatively, one or all of the arm members may have rounded or curved edges 170, as shown in the end view of FIG. 8, to facilitate delivery of the assembly through catheter 54 as well as to reduce any potential wear against the internal catheter surface or injury to valve tissue. For example, if a delivery catheter having a 6 mm internal diameter, each respective arm member may have a cross sectional width, e.g., of about 5 mm and a height, e.g., of about 2 mm. Having the curved edges 170 may allow for the translation of the assembly through the catheter lumen without wearing along the lumen surfaces. Moreover, the curved surfaces and edges of each arm member may also reduce any potential wear on the contacted mitral leaflets as well.

Figures 9A, 9B:
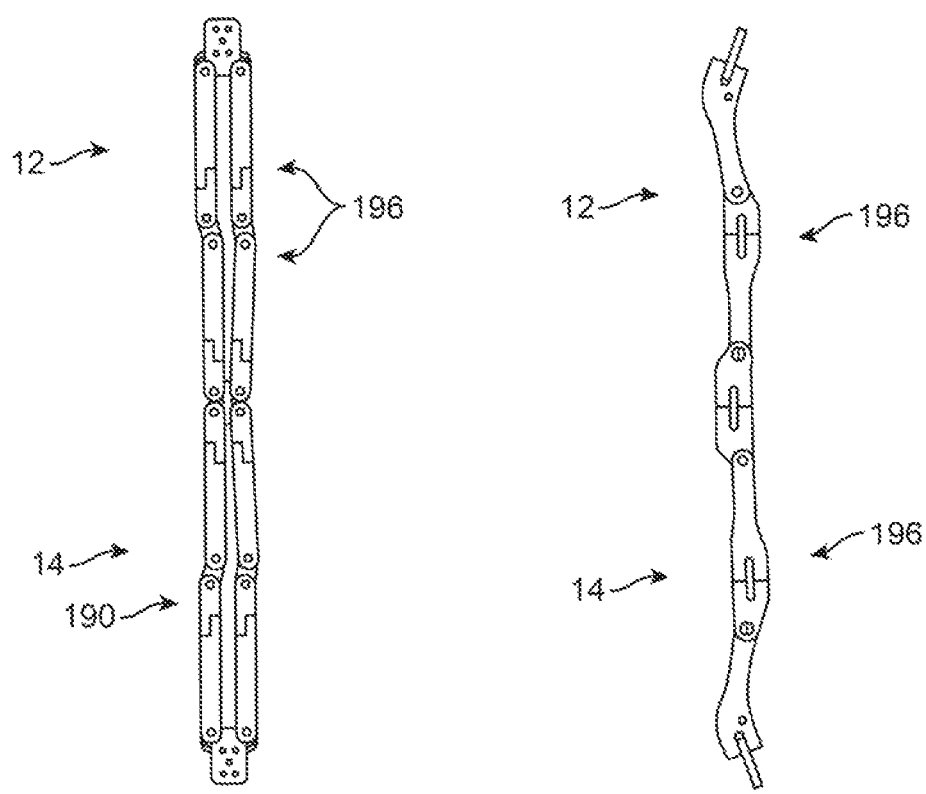
FIGS. 9A to 9C illustrate front, side, and perspective views of another variation of the interventional device having the one or more features formed upon the respective arm members for contacting against the leaflets.
Figure 9C:
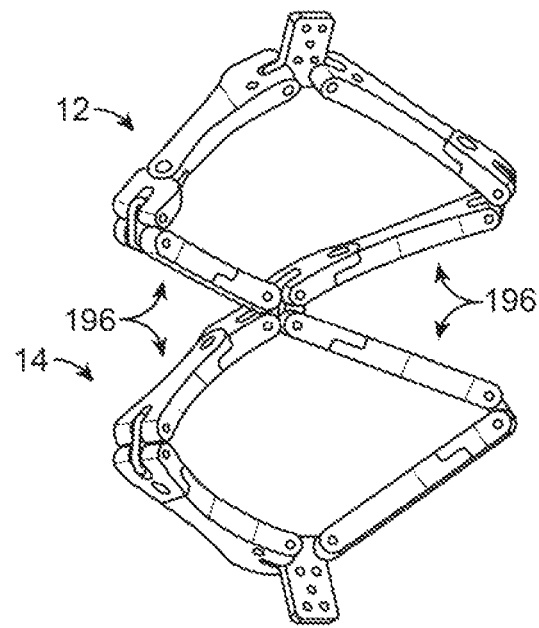
Figure 10A:
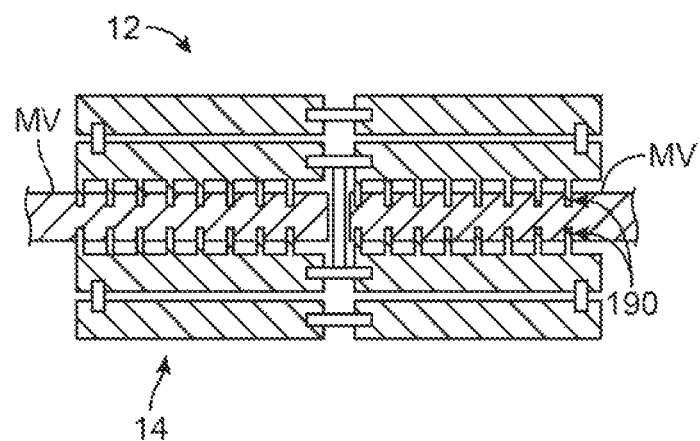
FIGS. 10A to 10C illustrate partial cross-sectional side views of the reconfigured interventional device having one or more various features upon the arm members for adhering against the leaflets.
Figure 10B:
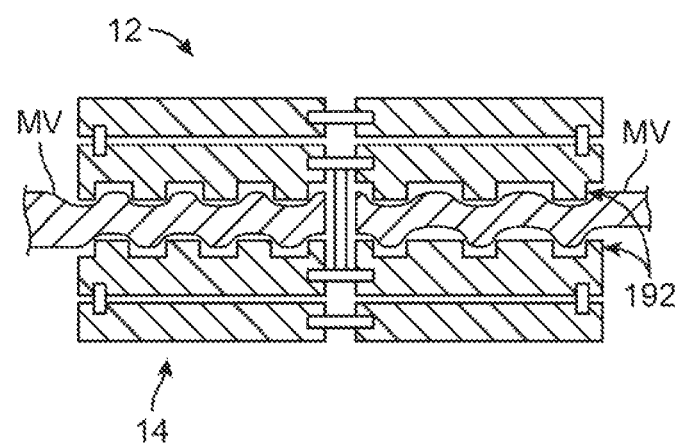
Figure 10C:
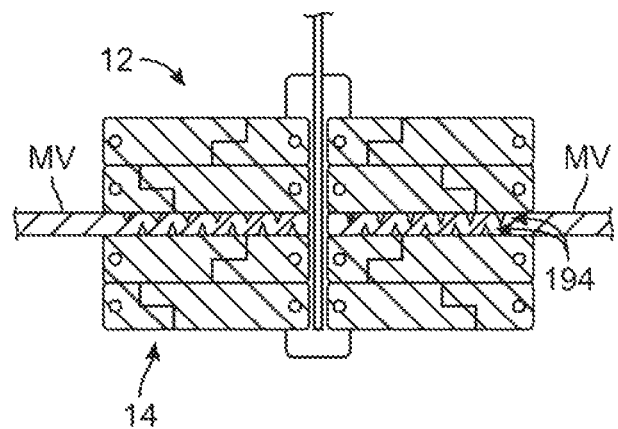

In any of the variations of the interventional devices described herein, various features or projections such as pins 190, castellations 192, raised tabs 194, or any other projections, protrusions, bumps 196, or features which may facilitate engagement with a replacement mitral valve implant may be formed along one or more arm members, for example along the surface of the arm members which face the central region of the mitral valve when deployed as shown in FIGS. 9A to 9C. Additionally and/or alternatively, these various features may additionally or alternatively be defined along the surfaces of the arm members which come into direct contact against the mitral valve leaflets. For example, as shown in the cross-sectional side view of FIGS. 10A to 10C, the arm members of both proximal and distal stabilizing structures 12, 14 which extend into contact against the surfaces of the mitral leaflets may also incorporate various features. Examples shown may include projections 190, tabs 192, or pins 194 which may simply compress upon the opposed surfaces of the mitral leaflets or they may be correspondingly designed to interdigitate or lock in an alternating pattern with respect to opposed features or projections when brought down upon the mitral leaflets into a locking configuration. Moreover, such features or projections may be covered by a fabric or covering, such as a kitted sleeve, to present a relatively atraumatic surface.

Figure 11A:
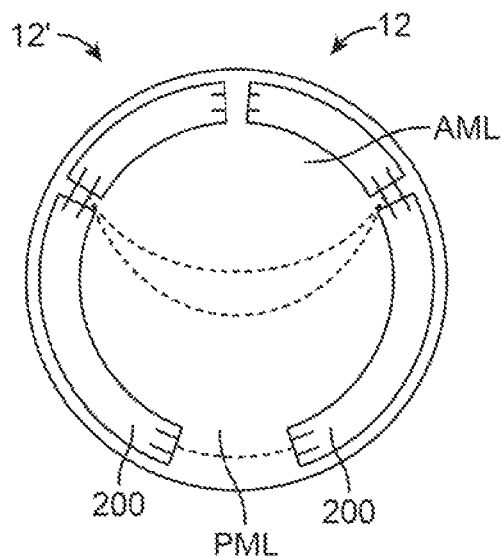
FIGS. 11A and 11B illustrate top views of variations where the arm members may be configured to be tapered or narrowed for minimizing interference with the leaflets.
Figure 11B:
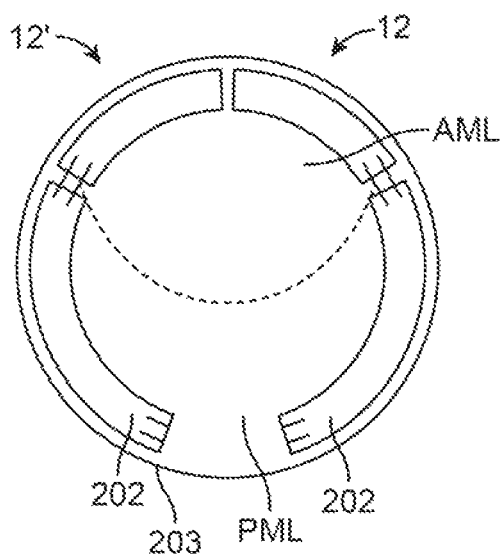

In yet another variation, the arm members may be further varied by incorporating narrowed or tapered arms 200 that may reduce any risk of perivalvular leakage in the space between the arms, if any, as shown in the top view of FIG. 11A. Alternatively, the stabilizing assemblies may incorporate narrowed or tapered arms 202 which taper or narrow to a point as they approach the posterior wall 203 of the mitral valve MV such that any replacement valve may directly contact against the posterior wall 203 without any gaps, as shown in FIG. 11B.

Figure 11C:
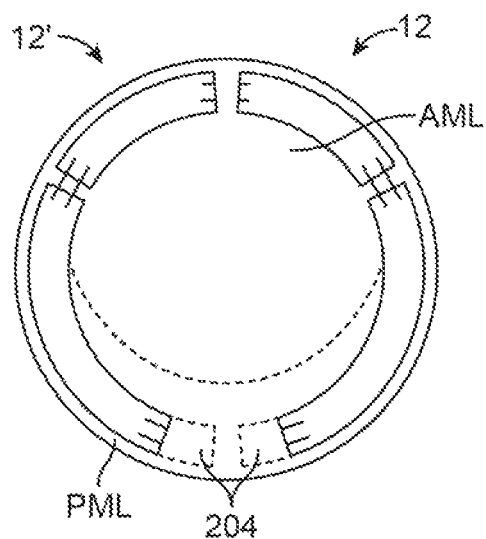
FIG. 11C illustrates a top view of another variation where the arm members may include extensions for providing additional stabilization to the leaflets or where the interventional devices may be secured to one another for further stabilizing the leaflets.

FIG. 11C shows a top view of another variation where the arm members may incorporate extensions 204 which may extend linearly or may fold out from the posterior set of arms to fill in any gaps along the posterior leaflet PML. The extensions 204 may optionally extend partially or may lock with respect to an apposed extension 204, as described in further detail below.

Figure 12A:
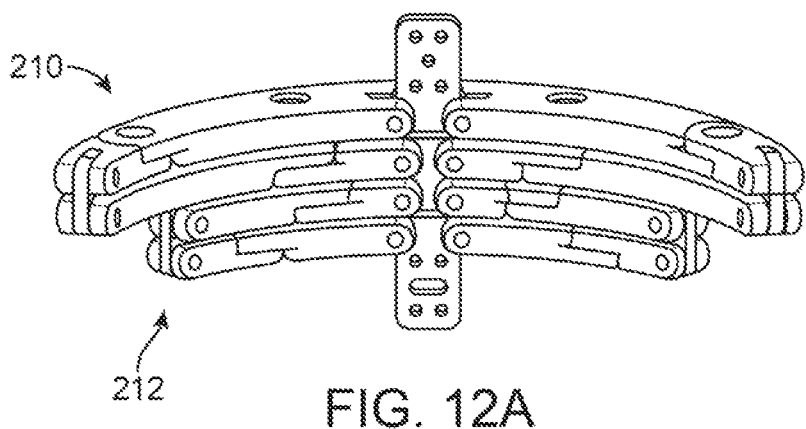
FIGS. 12A and 12B illustrate perspective and side views of another variation where the distal stabilizing structure may be formed to have arm members which are relatively shorter than the arm members of the proximal stabilizing structure when in their deployed configurations.
Figure 12B:
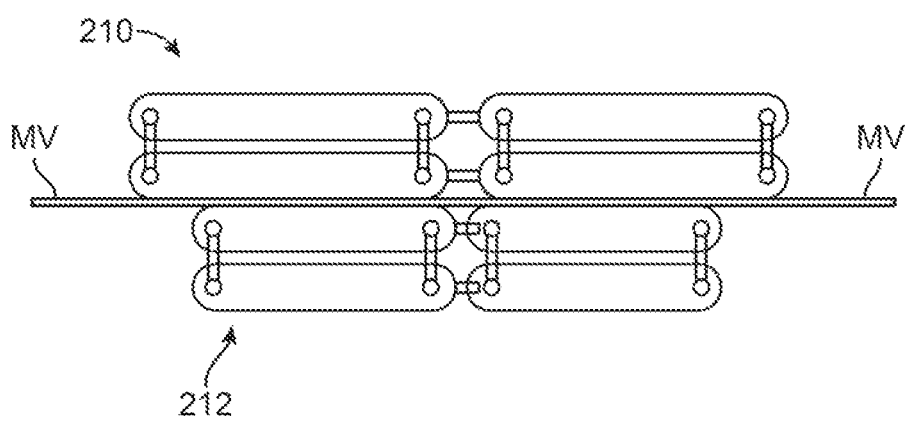

FIGS. 12A and 12B show perspective and front views of yet another variation where the arm members may be configured in an alternative arrangement. In this variation, the supra-annular structure 212 may be configured to have deployed arm members which are relatively shorter than the deployed arm members of the proximal stabilizing structure 210 to facilitate deployment of the subannular assembly 212 without interfering with the chordae tendineae CT, or papillary muscles PM or wall of the left ventricle. The lengths of the shortened subannular arm members may vary along any range and may also be configured to be relatively longer than the arms of the supra-annular assembly 210 in yet other variations the supra-annular arms may be long enough to completely encircle the valve.

Figure 13A:
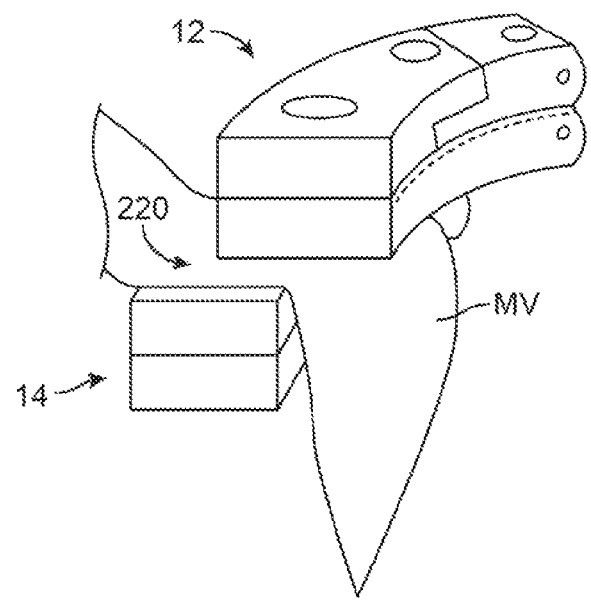
FIGS. 13A to 13C illustrate perspective and side views of another variation where the distal and proximal stabilizing assemblies may be staggered with respect to one another in their deployed configurations to increase the stabilizing surface area against the leaflets or to provide for further securement of the leaflets.
Figure 13B:
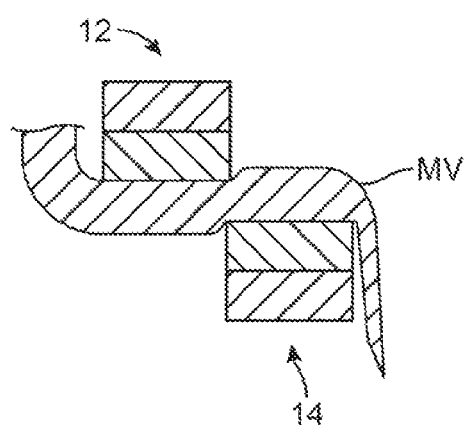
Figure 13C:
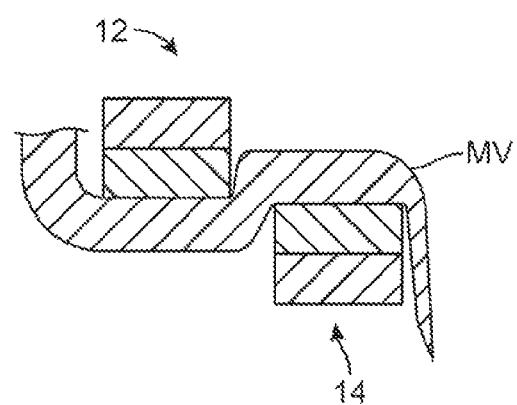

FIGS. 13A to 13C illustrate perspective and cross-sectional side views of additional variations in the arm member configuration. As shown in FIG. 13A, the individual arm members may configured such that the subannular and supra-annular assemblies 12, 14 are radially offset in such a way that the subannular arm members are positioned towards the center of the valve orifice, further than the supra-annular arm members, such that the effective width of the combined arm members covers a larger area of the valve leaflets which moves the leaflet hinge point further toward the center of the valve orifice and limits the upwards billowing of the leaflets, e.g., during systole, to improve the ability of the leaflets to close effectively.

FIGS. 13B and 13C illustrate cross-sectional side views where the arm members of the supra-annular structure 12 are positioned further away from the center of the valve orifice (in an opposite direction from that shown in FIG. 13A). In this variation, the arm members of the supra-annular structure 12 may be substantially adjacent to (as shown in FIG. 13B) or may just extend beyond (as shown in FIG. 13C) or may overlap slightly with the arm members of the subannular-structure 14. Such an arrangement increases the area of contact with the leaflets and may help to ensure the securement of the assembly to the leaflets. In addition, as shown in FIG. 13C, where the subannular structure is further offset from the supra-annular as to have a gap disposed radially between them, the leaflet may be folded or crimped through the gap so as to further enhance the grip on the leaflets.

Figure 14A:
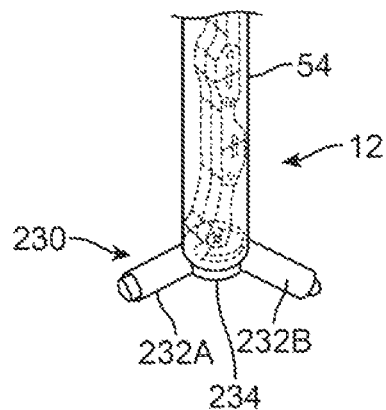
FIGS. 14A to 14C illustrate perspective views of another variation of an interventional device which may incorporate telescoping arm members for deployment along the subannular surface.
Figure 14B:
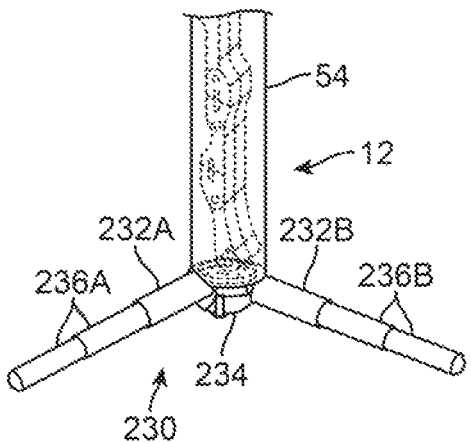
Figure 14C:
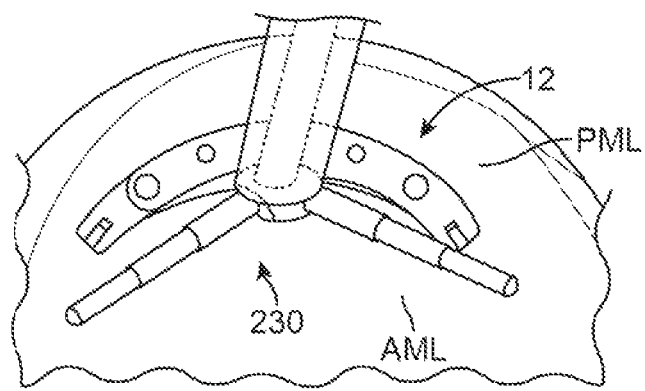

In yet additional variations, rather than the proximal interventional device being modified, the distal interventional device may be modified. One variation is shown in the perspective views of FIGS. 14A to 14C which illustrate a telescoping assembly 230 which may be deployable in the sub-annular space below the plane upon the ventricular side of the mitral valve MV. The telescoping assembly 230 may be comprised of telescoping arms 232A, 232B which are attached to a pivoting assembly 434 which may be used to position the arms 232A, 232B from a low-profile axial configuration to a radially-oriented deployed configuration, as shown in the figures. Once positioned for extension, one or more telescoping members 236A, 236B may extend linearly at an angle relative to one another (acute, right, or obtuse depending upon the desired configuration) from each arm 232A, 232B. Alternatively, the telescoping members 236A, 236B may extend in a curved or arcuate manner to form curved arm member when deployed. In yet another configuration, one telescoping arm may extend linearly while the opposite arm extends to form a curved deployed arm. Having the arms telescope outwardly just below the leaflets may avoid entanglement with various ventricular obstructions such as the chordae tendineae CT and/or papillary muscles PM. With the arms fully extended, the proximal stabilizing structure 12 may then be deployed for securement upon the upper leaflet surfaces, as shown in FIG. 14C.

Figure 15A:
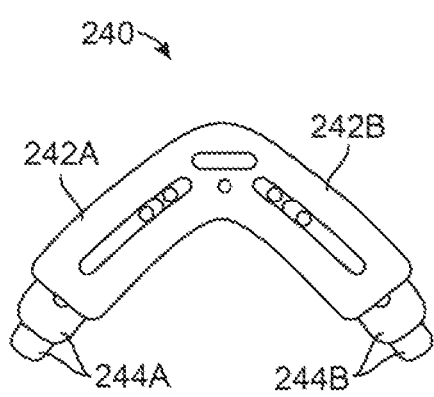
FIGS. 15A to 15C illustrate top and end views of another variation of telescoping arm members which may configure into curved arm members.
Figure 15B:
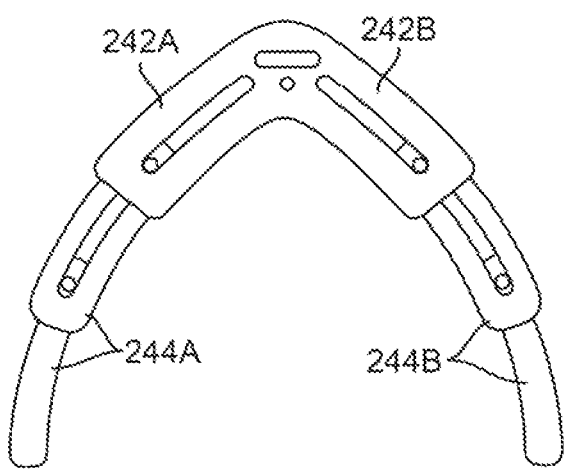
Figure 15C:
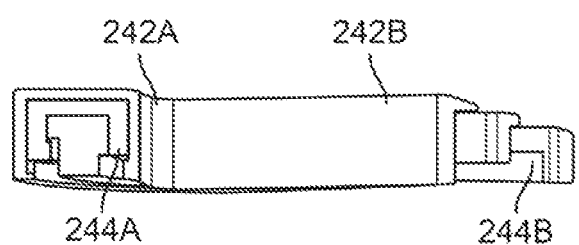

Another variation of telescoping arm members may be seen in the end and side views of FIGS. 15A to 15C. These telescoping arm members may be used for either the first or second assembly, or both. The telescoping assembly 240 may generally comprise telescoping arms 242A, 242B which may be partially curved or straight and coupled to one another via a pivoting assembly (not shown) to allow for an axially-elongated delivery profile. One or more telescoping members 244A, 244B may be slidably nested within each segment, as shown in FIG. 15C, so as to minimize profile and maintain rigidity in their fully deployed position. The members 244A, 244B may each have matching curvatures and have their longitudinal axis coincident with one another such that when the arms are deployed, they may extend to follow a perimeter of the mitral valve, as shown in FIG. 15B.

Figure 15D:
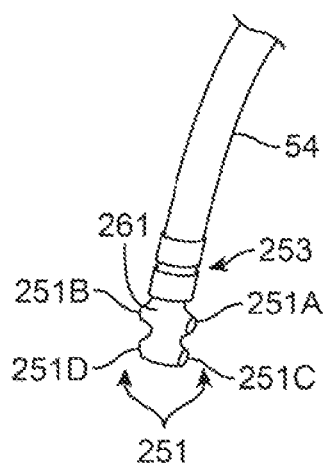
FIGS. 15D and 15E illustrate a perspective view of another variation of a device having two or more arms which may project perpendicularly or at an angle relative to a catheter for capturing a valve annulus or leaflets between the arm members.
Figure 15E:
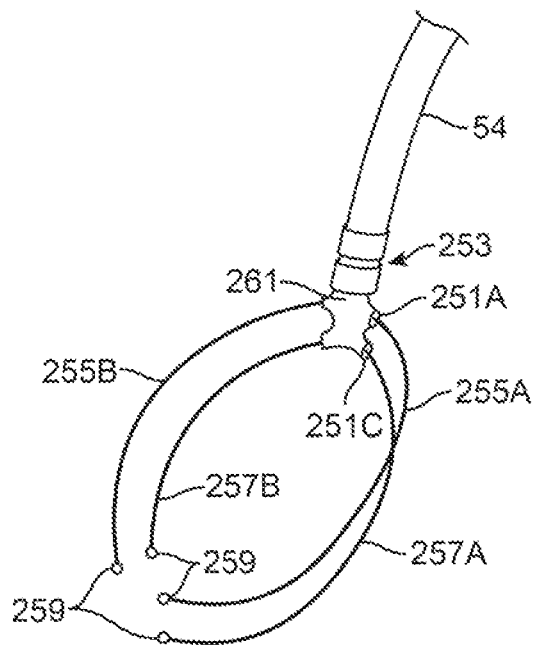

FIGS. 15D and 15E show yet another variation where two or more arm members may be projected from within a catheter 54 to a deployed configuration where the arm members extend to form a curved or arcuate element. The arm members may extend perpendicularly or at an angle relative to the catheter 54 for extending over a valve, such as the mitral valve, both supravalvularly and subvalvularly to compress upon the annulus or upon the a periphery of the valve leaflets. Thus, the catheter 54 may be inserted or directly positioned at the level of the medial or lateral mitral valve commissure with supravalvular and subvalvular exit sites for the arm members to be placed in the, e.g., subannular space, between the valve leaflets and the ventricle and separate arm members to be placed in the, e.g., supraannular space, to achieve annular stabilization.

As illustrated in the perspective view of FIG. 15D, catheter 54 is shown having arm member deployment assembly 261 attached to a distal end of the catheter 54 via detachable coupling 253. The deployment assembly 261 may define two or more openings 251 through which the arm members, which are positioned within the catheter 54 during delivery, may be extended through for deployment. The openings 251, in this variation, may be positioned about the deployment assembly 261 to allow for the arm members to extend in a curved or arcuate manner from the catheter 54. Thus, the openings 251 may be positioned in opposition to one another or at an angle relative to one another. An example is illustrated here showing at least two openings 251A and 251B positioned adjacent to one another about a circumference of assembly 261 for deploying at least two arm members supravalvularly. Two additional openings 251C and 251B are also shown adjacent to one another and distal to the openings 251A and 251B, respectively, at a distance for deploying at least two arm members subvalvularly.

As shown in the perspective view of FIG. 15E, arm members 255A and 255B are illustrated advanced from catheter 54 and extending through respective openings 251A and 251B. Also shown are arm members 257A and 257B extending from respective openings 251C and 2510 and projecting adjacent to respective arm members 255A and 255B. Each of the arm members may extend from a straightened configuration within the catheter 54 during delivery to a curved or arcuate configuration when urged distally from within the catheter 54, e.g., using a pushing mechanism or other actuator, and when released from the constraints of the catheter 54 lumen. The arm members may curve into a shape which approximates a periphery of the valve, such as the mitral valve, such that when urged from the respective openings the opposing arm members extend perpendicularly or at an angle relative to the catheter 54 and curve towards one another, as shown. For instance, as arm members 255A and 255B project from their respective openings 251A and 251B, they may extend at an angle relative to catheter 54 and also initially extend away from one another to then curve and extend towards one another such that the deployed shape approximates the valve periphery. Arm members 257A and 257B may similarly extend adjacent to arm members 255A and 255B.

Each of the arm members may also form an atraumatic blunt end 259 so as to prevent or inhibit tissue damage as the arm members are projected. The arm members may be constructed from various biocompatible materials sufficient to provide flexibility yet are rigid or semi-rigid enough to provide support to the valve leaflets, e.g., shape memory alloys such as nitinol, stainless steels, etc. Alternatively, the arm members may be constructed so as to be form inflatable tubular structures that may have rigidity induced by an inflation gas, fluid, or other medium (e.g., saline, water, etc.) introduced into the arm structures at a sufficiently high pressure. Alternatively, the rigidity along the arm members may be induced by inflating the arms with a hardening fluid. Additionally and/or alternatively, the arm members may have any number of frictional components or projections (barbs, spikes, etc., or any of the projections or elements described herein) formed upon the contact surfaces of the arm members to increase the fixation between the arms and the underlying tissue.

Moreover, the length of each arm member may be uniform with respect to one another or they may be varied depending upon the designed configuration and anatomy of the valve. While the arm members may be projected to extend partially about the periphery of the valve, they may alternatively be projected to extend distally such that the respective distal ends overlap upon one another at least partially to increase annular rigidity.

Figure 15F:
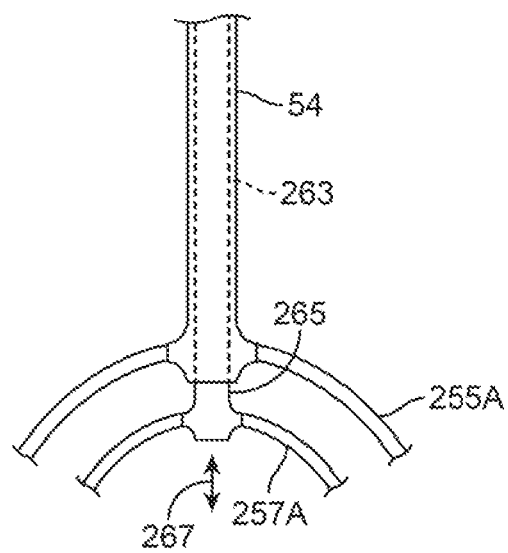
FIG. 15F illustrates another variation where the subvalvularly positioned arms may be configured to extend from an inner catheter which is translatable relative to an outer catheter to facilitate compression of the tissue between the extended arm members.

Once deployed, the supravalvularly positioned arm members 255A, 255B may compress against their respective subvalvularly positioned arm members 257A, 257B such that the annular or leaflet tissue therebetween may be compressed and supported structurally. To further compress and support the tissue, the supravalvularly positioned arm members 255A, 255B and subvalvularly positioned arm members 257A, 257B may be located along separate deployment devices. An example is illustrated in FIG. 15F, which shows catheter 54 having supravalvularly positioned arm members 255A, 255B projecting from its distal end but with subvalvularly positioned arm members 257A, 257B extending from a deployment assembly 265 attached to a separate deployment catheter 263 which may be positioned within catheter 54. The separation of the pair of arm members may allow for catheter 263 to be translated 267 relative to catheter 54 to further compress or adjust the positioning of the assembly relative to the valve.

Figure 16A:
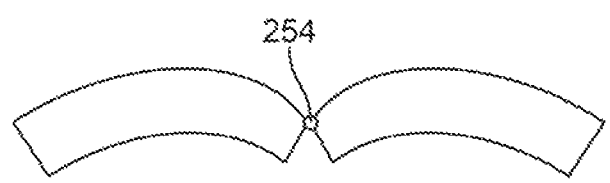
FIGS. 16A to 16B illustrate a perspective view of another variation where the hinge member may be positioned along a side of the arm members away from the valve annulus when deployed.
Figure 16B:
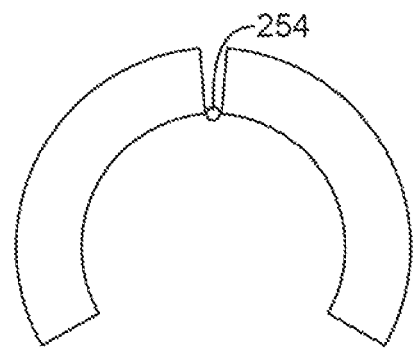

FIGS. 16A and 16B illustrate top views of the interventional device where placement of the middle hinge or pivot 254 may be varied. For example, as shown in FIG. 16A, hinge or pivot 25 may be located on the outer edge allowing the arm members to extend towards the periphery of the valve as much as possible. Alternatively, as shown in FIG. 16B, the hinge or pivot 254 may also be placed as close as possible to the center of the mitral orifice so that the arm members may be positioned as close as possible to the inner perimeter of the mitral valve MV to provide support while distorting the leaflets as little as possible.

II. Deployment

FIGS. 17A to 17E illustrate one variation of the mechanism of deployment for an interventional device. A distal stabilizing structure 14 is advanced beyond the distal opening 262 of the catheter sheath 54. An actuation member 264 (e.g., wire, suture, catheter, etc.) may be attached to a distal stabilizing structure 14 may be tensioned or actuated while a proximal portion of the distal stabilizing structure 14 is maintained against the catheter opening 104. With the proximal stabilizing structure 12 still constrained within the catheter 54, the arms of the distal stabilizing structure 14 may be reconfigured to deploy, as shown in FIGS. 17B-17C. For example, when an actuation force is applied to the actuation member in a proximal direction, the distal end 261 of the distal stabilizing structure 14 is urged in a proximal direction while the proximal end 263 of the distal stabilizing structure 14 is prevented from proximal movement by the catheter sheath 54, thus pulling the distal end 261 towards the proximal end 263. With the distal stabilizing structure 14 fully in a laterally-elongated configuration, as shown in FIG. 17C, the catheter opening 262 may be withdrawn further until the proximal stabilizing structure 12 is exposed, as shown in FIG. 17D. The actuation member 264 may then be tensioned further with the catheter opening 104 used as a backstop against the proximal portion of the proximal stabilizing structure 12 to reconfigure the proximal stabilizing structure 12 into its laterally-elongated configuration, as shown in FIGS. 17D and 17E.

FIGS. 18A to 18F show perspective views illustrating how the one or more interventional devices 10, 10' may be deployed relative to the mitral valve leaflets for providing leaflet stabilization and/or anchoring devices for a prosthetic valve. As shown, in a typical antegrade approach (as discussed herein) a first interventional device 10 may be advanced between the posterior and anterior mitral leaflets PML, AML until the distal stabilizing structure 14 through the valve to a subannular position. The distal stabilizing structure 14 may be deployed first or both the proximal and distal stabilizing structures 12, 14 may be reconfigured simultaneously such that proximal and distal stabilizing structures 12, 14 reconfigure into their laterally-elongated configurations on opposite sides of the annulus, compressing the leaflets, as shown in FIGS. 18A to 18C. The catheter 54 has been omitted for clarity purposes only.

A second interventional device 10' positioned within the catheter 54 proximally of the first interventional device 10 may then be deployed at a second location along or upon the mitral valve by repositioning the catheter accordingly and then advancing the distal stabilizing structure 14' to a subannular position and the proximal stabilizing structure 12' to a supra-annular position. Once suitably positioned, the stabilizing structures 12', 14' may be deployed sequentially or simultaneously to lock upon their respective leaflet surfaces, as shown in FIGS. 18D to 18F.

Figure 20A:
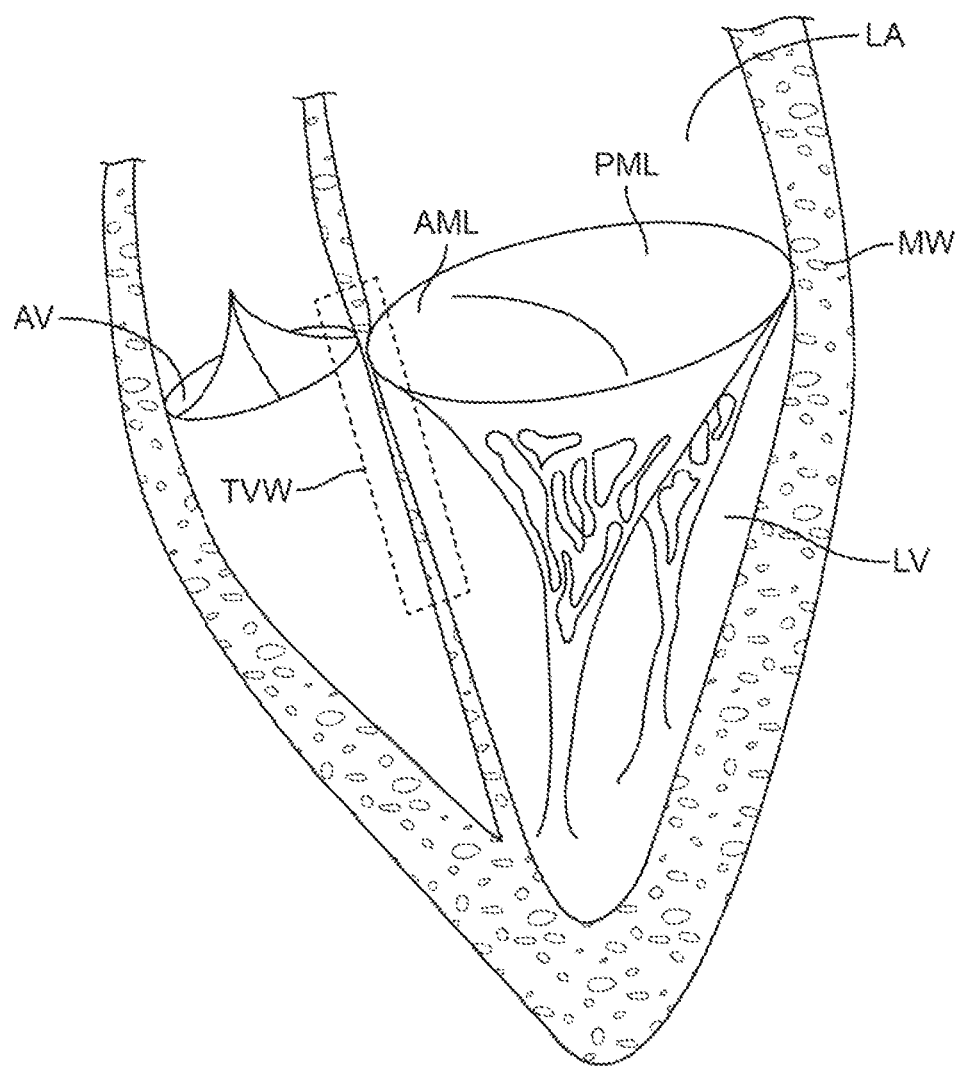
FIG. 20A illustrates an anatomical view of the thin vessel wall surrounding the anterior mitral leaflet.
Figure 20B:
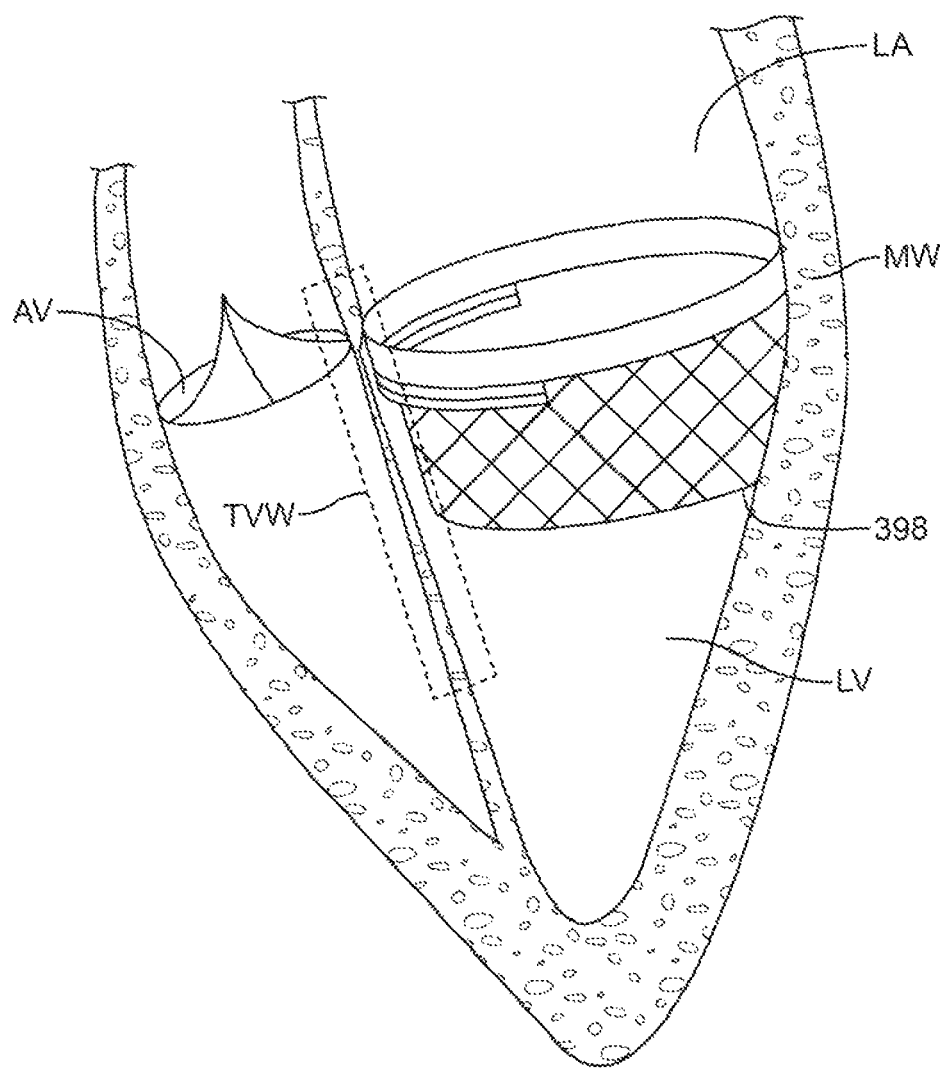
FIG. 20B illustrates an anatomical view of placement of a valve assembly utilizing one interventional device along the anterior leaflet.

Deployment of the interventional device(s) may be biased along the anterior side of the mitral valve, as shown in FIG. 18F. The mitral valve is bound by muscular tissue MW on the posterior side of the valve only. The inner wall of the mitral valve, surrounding the anterior leaflet, is bound by a thin vessel wall TVW separating the mitral valve annulus from the inferior portion of the aortic tract (as shown in FIG. 20A). As a result, little native structural support, if any at all, is provided on the anterior side of the mitral annulus. Therefore, by deploying each interventional device 10, 10' such that the majority of the stabilizing assemblies lie on or along the anterior leaflet, the interventional device(s) 10, 10' provide additional support for stabilizing the annulus and/or anchoring a replacement valve, as shown in FIG. 20B. In order to provide adequate circumferential support for a catheter-delivered prosthetic valve, the interventional devices 10, 10' together preferably cover, e.g., at least about 60% of the circumference of the mitral valve.

The first and second interventional devices 10, 10' may be accordingly positioned in the anterior and posterior commissures such that the curved arm members follow along a periphery of the valve annulus. Moreover, although two interventional devices 10, 10' are shown, a single interventional device may be used alone at either commissure. The arms may also be configured at various angles depending upon the desired configuration. Likewise, more than two interventional devices may also be deployed.

FIG. 19A illustrates a top view of a dysfunctional mitral valve MV where the posterior and anterior mitral leaflets PML, AML fail to coapt while FIG. 19B illustrates a top view of the mitral valve MV having a first and second interventional device 10, 10' deployed and positioned at either commissure. As shown, the interventional devices 10, 10' may follow the periphery of the annulus while maintaining a central region of the mitral valve MV uninhibited such that the leaflets may be supported by the assemblies to facilitate coaptation of the leaflets.

III. Locking Mechanisms

Once the interventional device 10 has been deployed, the device 10 may be locked into its deployed shape and left implanted upon or along the mitral valve. To ensure that the device remains secured upon the valve leaflets, various locking mechanisms may be implemented into the device.

In the variation shown in the front and perspective views of FIGS. 21A to 21C, the extension arm members may generally comprise an attachment member 270 which is attached or connected, for instance, along the arm member 272. The attachment member 270 may further extend linearly or curvilinearly along an extending member 274 which has a first atraumatic surface which may contact against a surface of the leaflet. When the interventional device has been reconfigured into its laterally-elongated configuration, as shown in FIG. 21C, the attachment member 270 may extend along a circumferential arm from the arm member at a distance from the proximal and distal stabilizing structures 82, 84. The opposite surface of extending member 274 may define one or more projections or teeth 276 for coming into a ratcheted locking engagement with an opposed corresponding set of projections on a second extending member of an additional repair assembly. In the example shown, the projections or teeth 276 may be positioned along the extending member 274 such that the atraumatic side of the member 274 may rest upon the surface of the valve leaflet while the projections or teeth 276 may extend away from the leaflet surface.

Figure 22A:
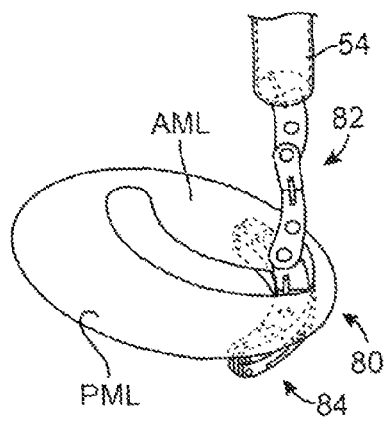
FIGS. 22A to 22F illustrate perspective views of one or more interventional devices having a respective extension member deployed upon a valve into locking engagement with one another.
Figure 22B:
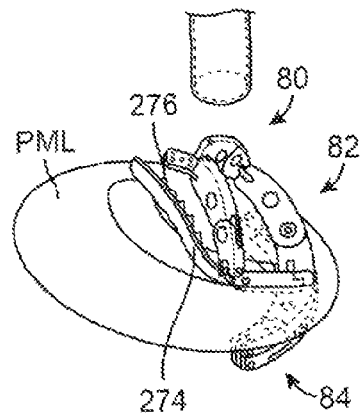
Figure 22C:
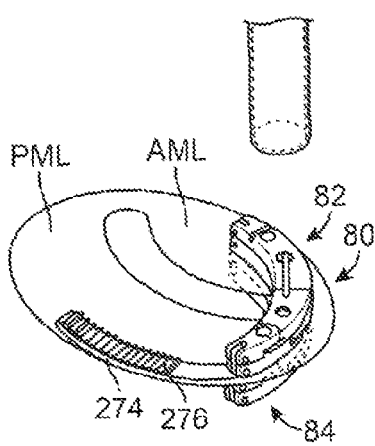
Figure 22D:
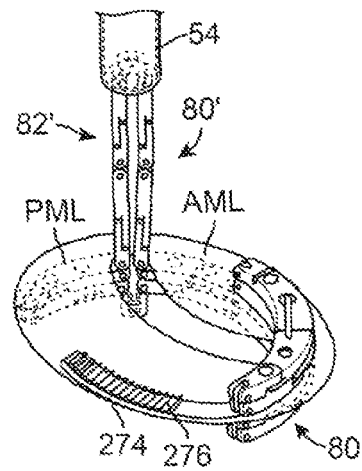
Figure 22E:
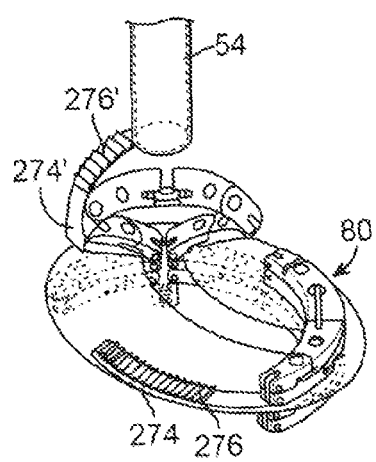
Figure 22F:
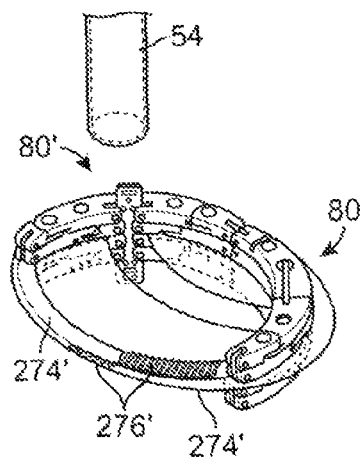

FIGS. 22A to 22F illustrate an example of how one or more interventional devices 80, 80' may be deployed relative to one another such that the extending members 274, 274' may be brought into an engaging contact. As previously described, the first interventional device 80 may be deployed and expanded at a first commissure such that the extending member 274 is deployed along a periphery of the valve annulus with the projections or teeth 354 positioned away from the leaflet surface, as shown in FIGS. 22A to 22C. The second repair assembly 80' may then be deployed and expanded at the second commissure in apposition to the first assembly 80 such that the second extending member 274' is also deployed along the periphery of the valve annulus. The second assembly 80' may have the projections or teeth 276' positioned towards the leaflet surfaces such that they may come into an engaging contact with the first extending member 274, as shown in FIGS. 22D to 22F. The engagement between the extending members 274, 274' may be ratcheted or loosened to adjust the positioning of the assemblies 80, 80' and the amount of support imparted to the underlying leaflets.

FIGS. 23A to 23B illustrate front and perspective views of yet another locking mechanism variation for a interventional device where a pair of curved stabilizing arms 280A, 280B may be combined with a distal stabilizing structure 84. The curved arms 280A, 280B may be folded when delivered through the catheter 54, as shown in FIG. 23A, but may extend radially outward to curve towards one another at their respective distal ends such that the curved arms 280A, 280B extend over or upon the leaflets and coincide between the leaflet commissure. The distal ends of the each curved arm 280A, 280B may define one or more openings 284 through which a locking suture or wire 282 may be passed to secure the arms to one another. In this manner, the positioning of the arms over the span of the valve may further provide stabilization over the entire valve.

FIG. 23C illustrates a top view of another locking mechanism variation for securing two or more interventional devices. A pair of curved stabilizing arms 280A, 280B may be combined with a distal stabilizing structure 84 to secure one interventional device to a second interventional device. The curved arms 280A, 280B may be folded when delivered through the catheter 54, as shown in FIG. 23A, but may extend radially outward so as to conform to the shape of the arms of the stabilizing structures and/or native valve. The length of the stabilizing arms 280A, 280B may be adjusted so as to exceed that of the distal arms, thereby extending past the ends of the distal arms of one interventional device to overlap with and/or connect to the distal arms of a second interventional device. Stabilizing arms 280A, 280B may be held in place through, e.g., pins, hooks, tabs, wires, sutures, etc. anywhere along the arms of the second interventional device.

Figure 24A:
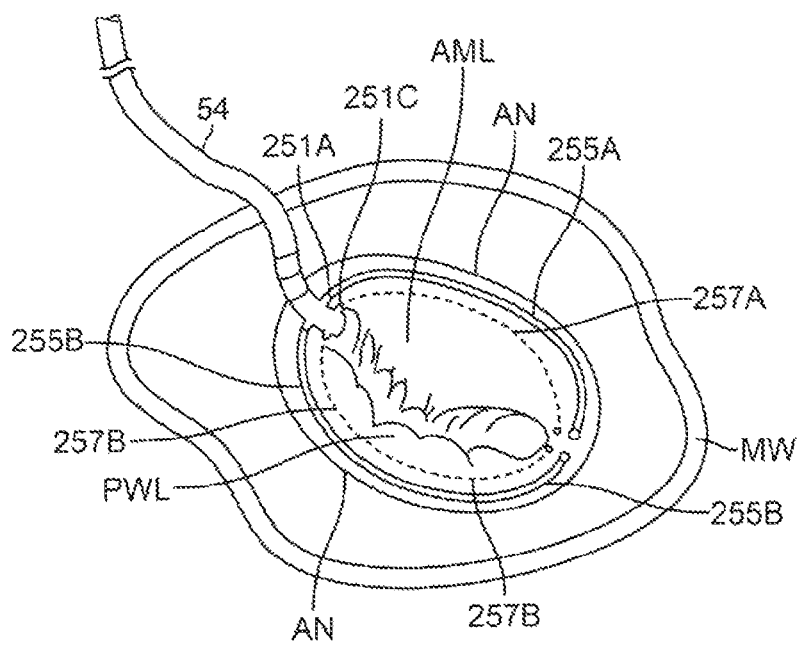
FIG. 24A illustrates the catheter assembly of FIGS. 15D and 15E positioned within a valve, such as a mitral valve, with the arm members extended and compressed upon the annular and/or leaflet tissue.
Figure 24B:
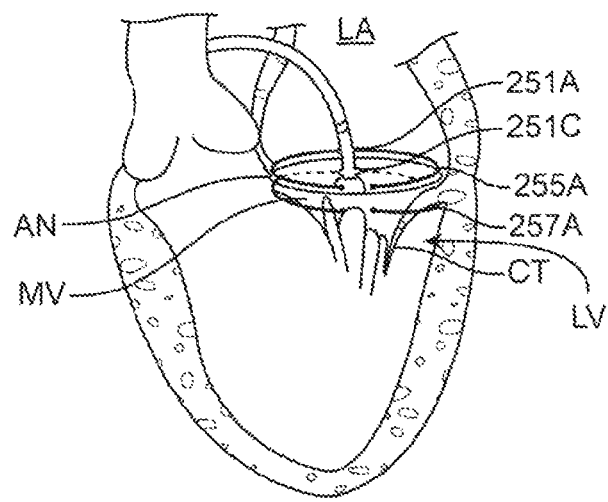
FIGS. 24B and 24C illustrate partial cross-sectional side views of the catheter assembly deploying the arm members and detaching from the assembly and securing a prosthesis to the arm members and through the valve.
Figure 24C:
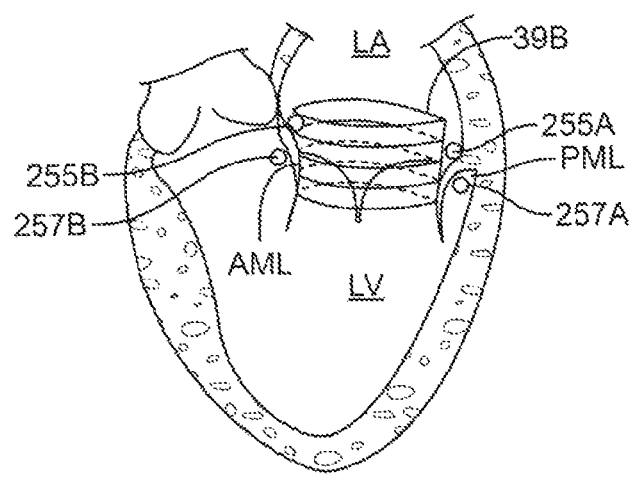

FIGS. 24A to 24C illustrate perspective and partial cross-sectional side views of yet another variation which utilizes the devices illustrated above in FIGS. 15D and 15E. A portion of the surrounding mitral wall MW may be seen in the figure for reference. After advancing the steerable catheter intravascularly to, e.g., the mitral valve located within the left atrial chamber, at the medial or lateral commissure from the atrial side or ventricular side, the catheter 54 may be positioned such that the detachable coupling 253 is positioned at least partially through the valve. With the proximal openings 251A and 251B positioned above the valve within the left atrium and the distal openings 251C and 251D positioned below the valve within the left ventricle, the supravalvular arm members 255A and 255B may be advanced from within the catheter 54 into their deployed configuration situated, e.g., in the supra-annular space upon the annulus AN or upon the superior surfaces of the posterior PML and anterior mitral leaflets AML, and subvalvular arm members 257A and 257B may be similarly advanced from within the catheter 54 into their deployed configuration, e.g., in the sub-annular space upon the annulus AN or upon the inferior surfaces of the posterior PML and anterior mitral leaflets AML, in apposition to their respective supravalvular arm members. As described above, the arm members may be uniform in length relative to one another or non-uniform in length and either partially or completely circumferentially deployed over or upon the valve.

FIG. 24B illustrates the partial cross-sectional side view of the catheter 54 positioned trans-septally in a superior position relative to the mitral valve. The deployed arm members may be seen after deployment and upon the annulus AN or valve leaflets. Because of the low-profile of the arm members, particularly the subvalvularly positioned arm members 257A and 257B, they may be introduced into the subannular space within the left ventricle LV and through the surrounding chordae tendinae CT attached to the leaflets without being inhibited.

After assuring adequate arm member placement, the coupling 253 of the catheter 54 may then be disconnected from the shaft of the catheter 54 leaving the deployed arm members in position. Because the arm members may have a spring like quality while imparting compressive and/or radial forces to the underlying valve, they may function to stabilize the assembly at the annular level.

The assembly may further provide a platform for placement of an implantable valve prosthesis which may be secured to the valve without the need for sutures, as illustrated in the partial cross-sectional side view of FIG. 24C. In patients with mitral regurgitation who are candidates for valve replacement, the assembly may be placed, as described herein, while under fluoroscopic, echocardiographic, and other imaging guidance. The rigidity of the arm member assembly may provide a platform for placement of a transcatheter valve and/or sutureless prosthesis such that a replacement valve prosthesis 398 may be advanced intravascularly and deployed through the valve while anchoring against or along the reinforced valve annulus and/or leaflets or directly against the deployed arm members.

Another approach is placement of assembly under direct vision or surgically. The valve commissure is identified and the tip of the catheter 54 placed at the junction of the subannular and supraannular regions. The assembly may also be percutaneously, trans-atrially, trans-septally, trans-apically or directly introduced and implanted as well. Passage of the arm members is continued into the subannular space followed by passage of the arm members into the supraannular space. The described approaches and the present device also may be used to provide a stable, rigid or semi-rigid annulus for the deployment of transcatheter valve and sutureless prostheses in other locations, such as the tricuspid valve.

Figure 24D:
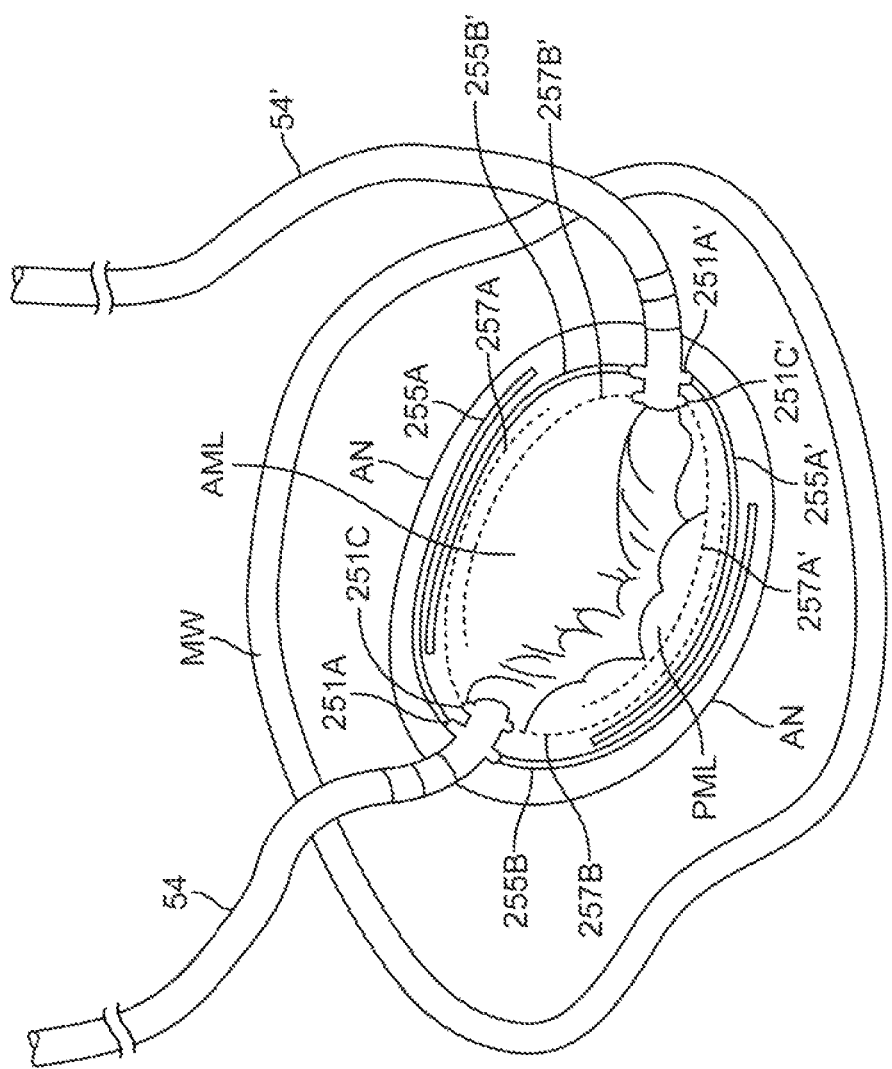
FIG. 24D illustrates a perspective view of an additional catheter assembly deployed in apposition to a first assembly.

In yet another variation, the catheter 54 may be utilized with an additional catheter 54', which may also be advanced into the heart chamber adjacent to the first catheter 54 or through an alternative path, to increase annular rigidity. Regardless of the entry path, with the first catheter 54 positioned at a first location about the valve, such as at a first location of the valve commissure, the second catheter 54' may be positioned simultaneously or sequentially at a second location about the valve, such as at a second location of the opposite valve commissure, as shown in the perspective view of FIG. 24D.

With the arm members 255A and 255B deployed supravalvularly and arm members 257A and 257B deployed subvalvularly, the additional supravalvular arm members 255A' and 255B' may be deployed supravalvularly and additional arm members 257A' and 257B' may be deployed subvalvularly. The additional arm members of the second catheter 54' may be deployed sequentially or simultaneously with the deployment of the arm members of the first catheter 54. Once each of the arm members have been deployed, each respective connector may be detached to leave the arm member assembly implanted upon the valve and the respective catheters 54, 54' may be withdrawn. As previously described, the arm members may then be left implanted to provide structural support to the valve or a valve prosthesis may be introduced and implanted through the valve utilizing the arm members for structural support.

Figure 25:
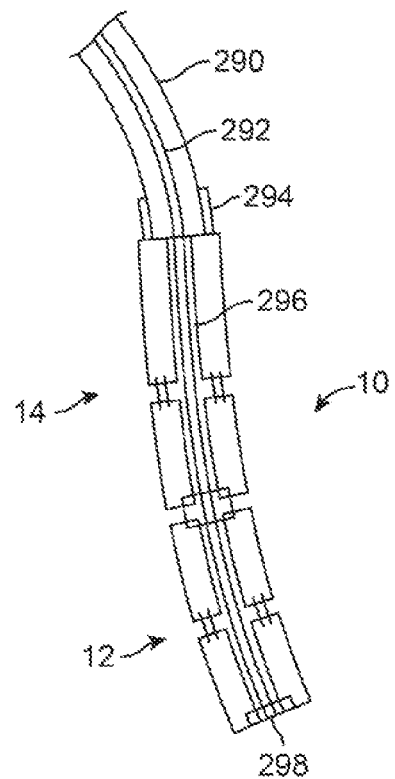
FIGS. 25 to 27 illustrate side, detail, and partial cross-sectional side views of another variation of an interventional device which may be reconfigured and locked into its deployed configuration using various locking mechanisms such as a threaded collar.
Figure 26:
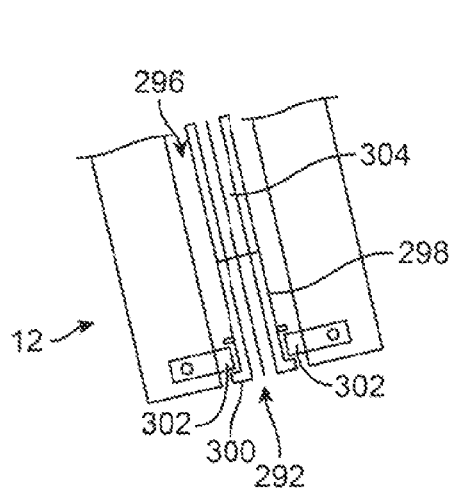
Figure 27:
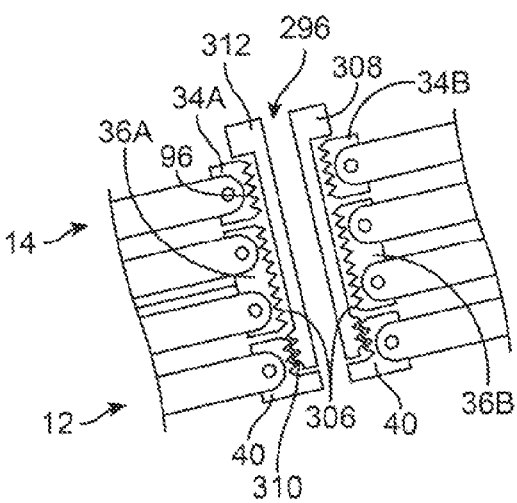

Another variation on a locking mechanism for the interventional device is illustrated in the side views of FIGS. 25 to 27 which show an outer catheter 290 which may be temporarily coupled to the proximal link 298 of the interventional device 10 via an outer catheter attachment 294, e.g., screw thread, gripping element with a release wire, or other suitable attachment mechanism. A separate inner catheter or wire 292 may pass through the outer catheter 290 and within a lumen 296 defined through the device 10 to a distally positioned inner catheter attachment 298, e.g., screw thread, gripping element with a release wire, or other suitable attachment mechanism. The inner catheter or wire 292 may be optionally pre-shaped or configured to hold or maintain a predetermined shape for holding the assembly 10 in the desired shape or configuration for facilitating deployment. Of course, the inner catheter or wire 292 may also be maintained in a straightened and flexible configuration which may allow the assembly 10 to naturally form itself into an appropriate curve.

During delivery and prior to assembly expansion, the inner catheter or wire 292 may be maintained in a stable position relative to the outer catheter 290. The inner catheter or wire 292 may be actuated or tensioned relative to the outer catheter 290 to expand or extend the device into its deployed configuration. To secure the laterally-elongated configuration, one variation for locking the device may comprise an outer catheter attachment screw 308 positioned at a distal end of the outer catheter 290. The attachment screw 308 may define a threaded portion 310 which may be rotated to engage the threading 306 defined along the lumen 306 of the device 10 such that the screw 308 is advanced distally through the lumen 306 until a locking collar 312 secures the proximal end of the device 10 relative to the distal end of the device 10, as shown in FIG. 27.

To release the device 10 from the catheters, one or more pairs of engagement arms having one or more protrusions 300 may comprise the inner catheter attachment 298 at the distal end of the inner catheter 290. The protrusions 300 may be maintained against one or more corresponding locking members 302 defined along the distal end of the lumen 296. A release wire positioned through a lumen 304 defined through the inner catheter 292 may be tensioned to allow the engagement arms to release from the locking members 302 thus allowing the interventional device 10 to detach from the catheter, as shown in FIG. 26.

Figure 28:
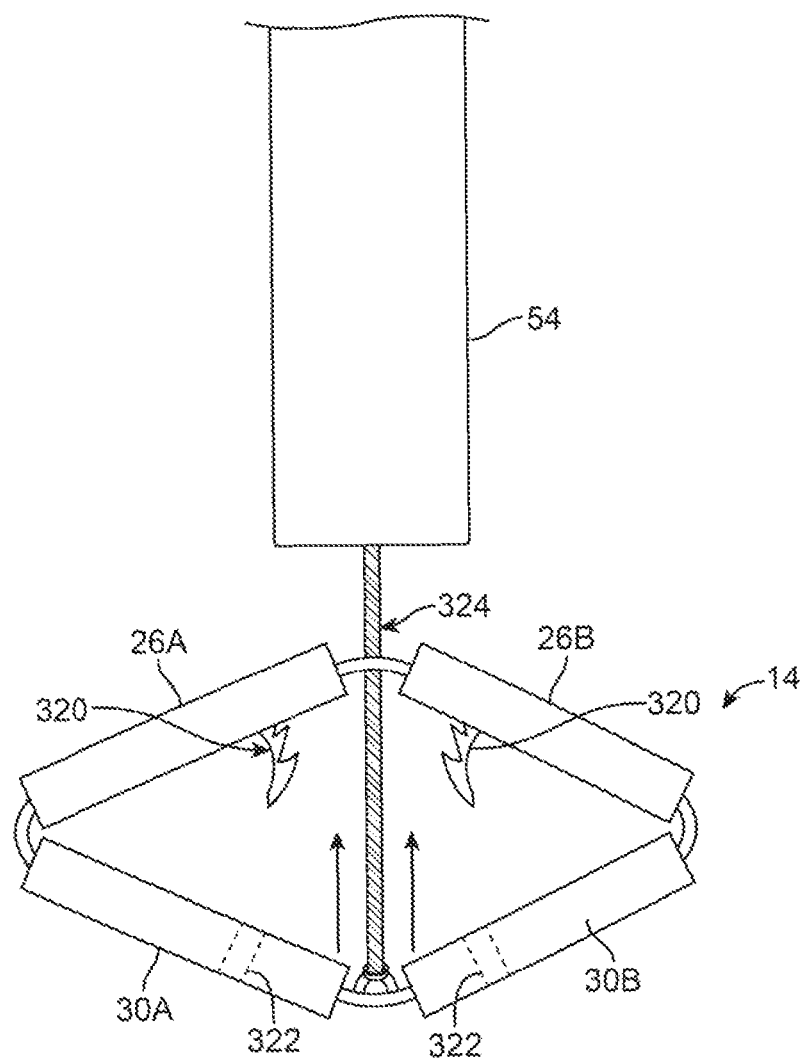
FIG. 28 illustrates a front view of another variation where the arm members may incorporate locking features extending from a first set of arms for engagement with a second set of arms for securing the device in its deployed configuration.

In yet another variation of the interventional device(s), FIG. 28 illustrates a side view of another variation where the device may incorporate one or more respective locking mechanisms 320 (e.g., pins, ratchets, etc.) positioned along a upper or lower surface of the arm members such that the locking mechanisms 320 are received into respective receiving channels 322 or another cooperating structure defined along apposed arm members when reconfigured into the deployed configuration. As previously described, a tensioning wire, suture, or catheter 324 may be coupled to a distal annular structure 14 such that when tensioned, the device may collapse into its laterally-elongated configuration. Also, as the arm members fold into their laterally-elongated configuration, the locking mechanisms 320 may be configured to penetrate through the leaflets and to be received into their respective receiving channels 322 and locked automatically to secure the arm members into their deployed configurations.

Figure 29A:
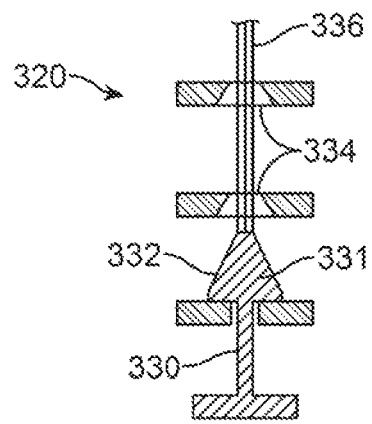
FIGS. 29A to 30 illustrate partial cross-sectional side views of ratcheting locking mechanisms which may be utilized to lock the interventional device.
Figure 29B:
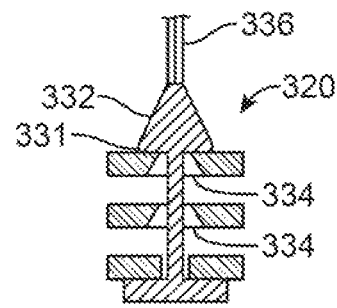
Figure 30:
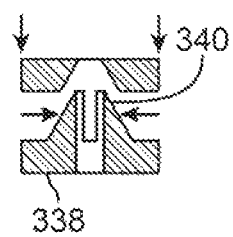

Examples of the different types of locking mechanisms 320 which may be utilized with the stabilizing assemblies may be seen the cross-sectional side views of FIGS. 29A and 29B. In this example, ratchet 330 may have a tapered lock 332 which may be incorporated into a distal arm member of the interventional device. Tapered lock 332 has a proximal shoulder 331 of larger diameter than openings 334. As the attached tensioning wire 336 is pulled, the tapered locking portion 262 may be pulled through the one or more openings 334 defined along the interventional device, e.g., through the pivoting mechanism, until the tapered locking portion 332 is fully drawn through the assembly to lock the device in its deployed configuration, as in FIG. 29B. FIG. 30 illustrates a cross-sectional side view of another variation of a locking ratchet 338 but in place of shoulder 331 the tapered portion may define one or more serrations or projections 340 to engage complementary features within openings 334 to enhance the locking securement.

Figure 30A:
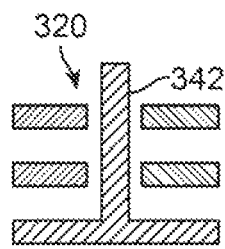
Figure 30B:
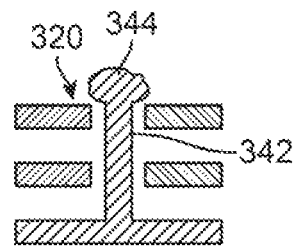

FIGS. 30A and 30B illustrate cross-sectional side views of another locking mechanism which may be drawn through the interventional device to lock the device in its deployed configuration. In this variation, the distal end of the interventional device may have a locking member 342 such as a wire or suture which may be tensioned through the interventional device and crimped or flattened to form a broadened retainer 344 directly upon the member 342 to prevent its withdrawal through the assembly.

Figure 31A:
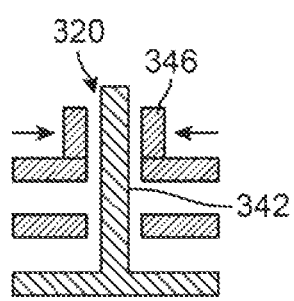
Figure 31B:
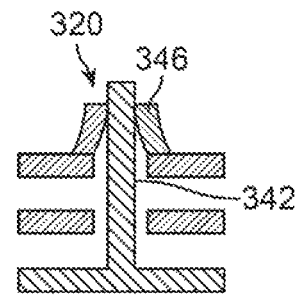

FIGS. 31A and 31B illustrate cross-sectional side views of yet another locking mechanism. In this example, the locking member 342 may be tensioned through the interventional device and a crimping collar 346 may be positionable over the member 342 and crimped upon the member 342 when compressed member 342 is drawn tightly.

Figure 32A:
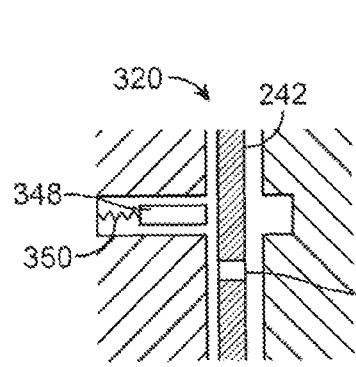
FIGS. 32A to 32C illustrate cross-sectional side views of another locking mechanism where the locking member may be tensioned to hold the interventional device into its laterally-elongated configuration.
Figure 32B:
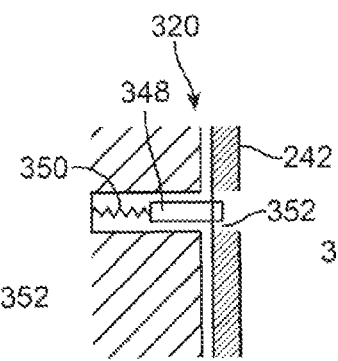
Figure 32C:
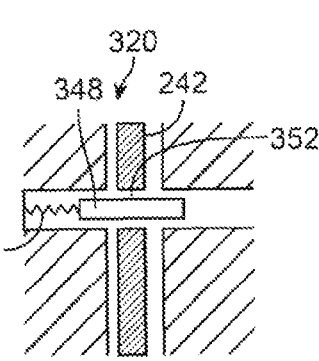

FIGS. 32A to 32C illustrate cross-sectional side views of another locking mechanism where the locking member 342 may be tensioned to hold the interventional device into its laterally-elongated configuration. One of the proximally positioned arm members or the proximal engagement link 32 may incorporate a locking pin 348 which is urged against the locking member 342 via a biasing element 350 such as a spring. As the locking member 342 is drawn proximally through the interventional device, the biased pin 348 may be inserted at least partially, as shown in FIG. 32B, or entirely, as shown in FIG. 32C, through an opening or slot 352 defined through a distal portion of the member 342. With the locking pin 348 inserted through the opening or slot 352, further movement of the member 342 may be inhibited relative to the interventional device thereby locking the configuration of the assembly.

Figure 33A:
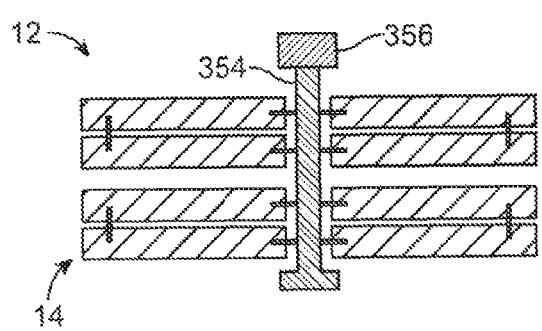
FIGS. 33A to 33C illustrate partial cross-sectional side views of another variation where the locking mechanism may incorporate a pin for locking partially or entirely through a slotted receiving channel.
Figure 33B:
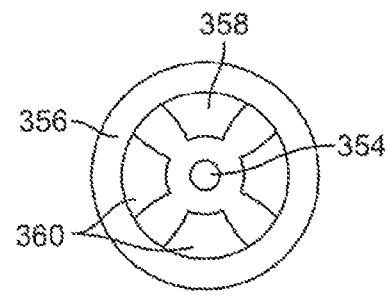
Figure 33C:
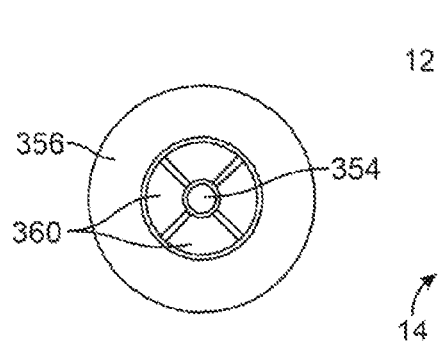

FIG. 33A illustrates a cross-sectional side view of yet another variation of a locking mechanism where a wire or rod 354 may be tensioned to move the proximal and distal stabilizing structures 12, 14 into their expanded configuration. A separate collet 356 may slide along the wire or rod 354 when the collet 356 is in an open configuration such that one or more movable locking members 358 extending radially within the collet 356 provide enough space for the wire or rod 354 to travel freely through, as shown in FIG. 33B. Once the interventional device has been desirably expanded, the collet 356 may be drawn down distally along the wire or rod 354 and locking members 358 moved radially inward to clamp down upon the wire or rod 354, as shown in FIG. 33C, thereby preventing movement of the collet 356 relative to the wire 354 and thus preventing or inhibiting the interventional device from reconfiguring back into its low-profile shape.

Figure 34:
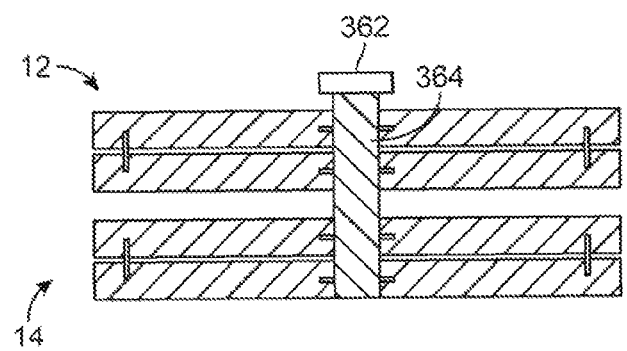
FIG. 34 illustrates a partial cross-sectional side view of another variation of a locking mechanism which utilizes a threaded member for securing the interventional device.

FIG. 34 illustrates a cross-sectional side view of yet another locking mechanism where a fastener 362 having threading 364 along its length may be simply rotated or screwed into the expanded interventional device to lock the configuration of the proximal and distal stabilizing structures 12, 14.

Figure 35A:
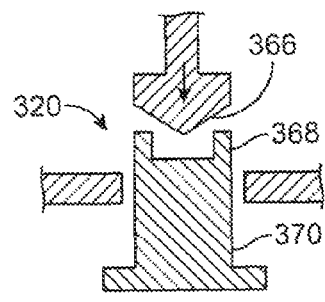
FIGS. 35A and 35B illustrate partial cross-sectional side views of another variation where a deformable rivet may be used as a locking mechanism.
Figure 35B:
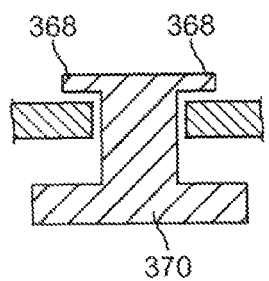

FIGS. 35A and 35B illustrate cross-sectional side views of another locking mechanism where a rivet 370 having a deformable collar 368 may be secured upon the interventional device once the assembly has reconfigured into its deployed configuration. A separate press 366 may be brought to bear upon the deformable collar 368 such that the collar 369 deforms radially to lock a position of the rivet 370 relative to the arm members. In this manner, the expanded configuration of the proximal and distal stabilizing structures 12, 14 may be secured.

Figure 36A:
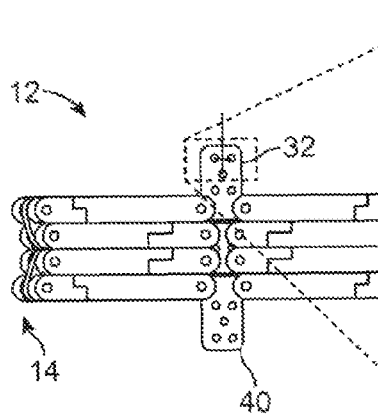
FIGS. 36A and 36B illustrate front and detail front views of another variation of a locking mechanism where a wire or suture may be passed through the interventional device and adjustably secured between the hinges or engagement links.
Figure 36B:
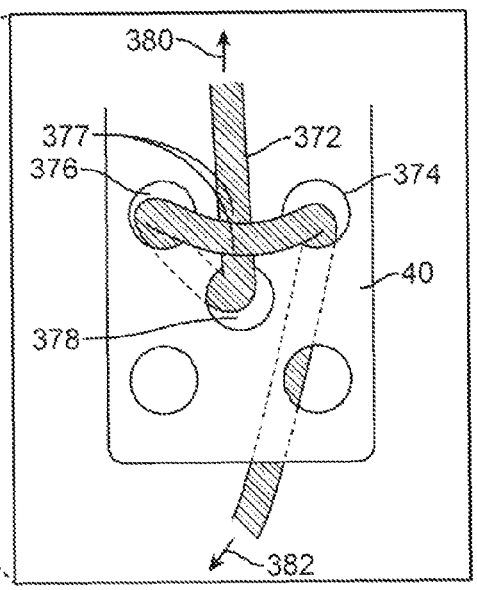

Yet another locking mechanism is illustrated in the front and detail front views of FIGS. 36A and 36B which show the relative positioning of the proximal and distal engagement links 32, 40 along the stabilizing structures 12, 14. In this variation, a tensioning suture or wire 372 may pass through the interventional device and couple the distal and proximal engagement links 32, 40 to one another. With the suture or wire 372 secured to at least one of the links, the remaining end of the suture or wire 372 may be adjustably secured to the opposing link using a one-way sliding knot to allow for adjustable locking of the interventional device. The remaining end of the suture or wire 372 may, for example, pass through a central opening 332 of the proximal engagement link 52 and then pass proximally through a first laterally offset proximal opening 376 and then crossover the wire 372 to second laterally offset proximal opening 374, from which it extends to the distal engagement link 32. Pulling the suture or wire 372 in a first direction 380, e.g., towards the opposing link, may allow for tensioning adjustment of the proximal and distal stabilizing structures 12, 14 while sliding of the suture or wire 372 in the opposing direction 382 is prevented due to friction between the portions 377 of the suture or wire that engage each other, thus locking the upper and lower arm members. This configuration may also allow adjustments to be made to the structures to allow for the release of the device from a particular configuration and the re-locking of the device, if so desired. For example, by releasing tension in the crossover portion 377 of the suture or wire 372, it will be allowed to slide in direction 382 to release the distal annular structure.

Figure 37:
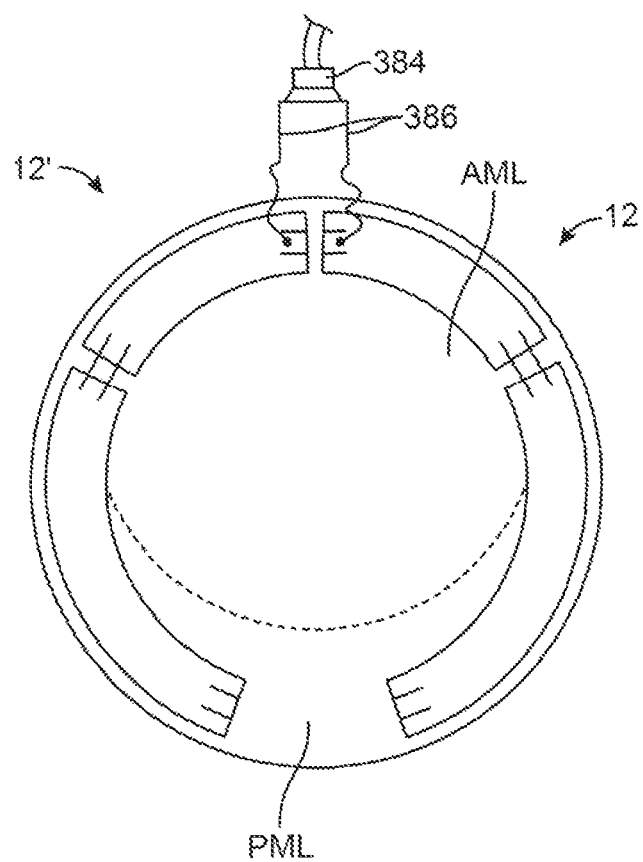
FIG. 37 illustrates a top view of another variation of a locking mechanism where a loop slides over adjacent links to lock the structures in place.

Yet another variation is shown in the top view of FIG. 37 which illustrates a variation where a coupling mechanism such as a sliding suture lock 384 may be advanced over wires or sutures 386 extending from the arms of multiple assemblies to create a rigid or secure connection between each of the implanted assemblies 12, 12' in their laterally-elongated configurations upon the valve leaflets. This is particularly useful when the distal and proximal stabilizing structures are deployed so that their combined periphery is biased towards one end of the valve, as shown, for example, in FIG. 18F.

IV. Valve

Figure 38A:
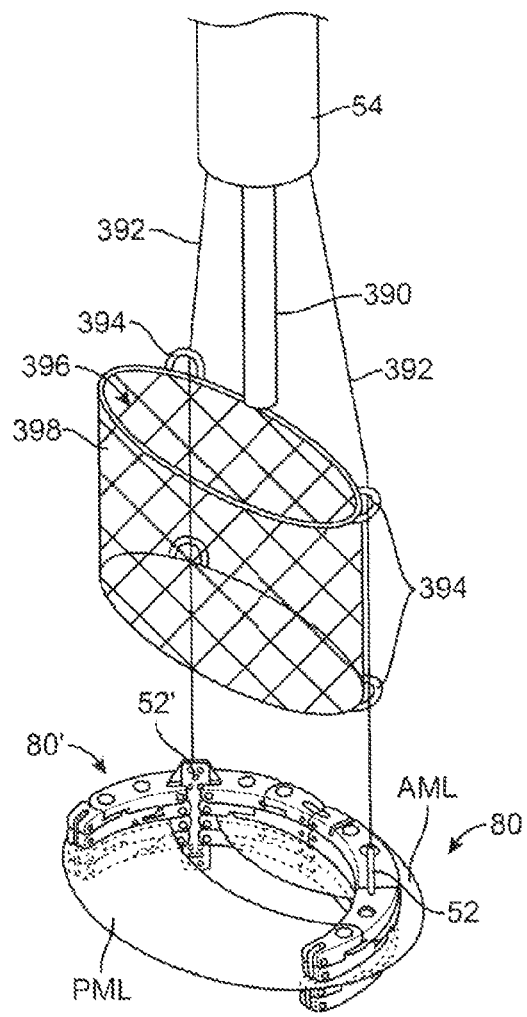
FIG. 38A to 38B illustrates a perspective view of another variation where a scaffold or implant valve assembly may be integrated with the one or more interventional devices.
Figure 38B:
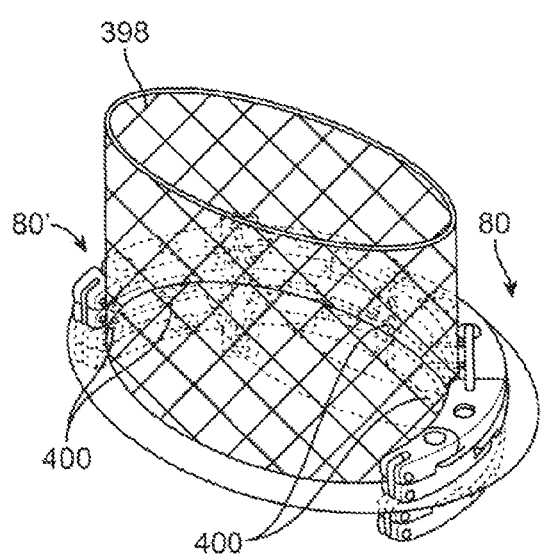
Figure 39:
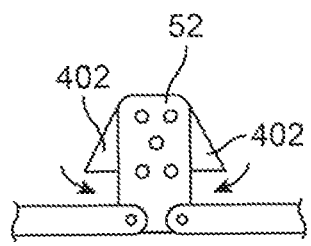
FIG. 39 illustrates a side view of a locking mechanism for attaching the valve assembly.

In any of the interventional device variations described, one or more assemblies may be utilized alone or in combination with an implanted stent, scaffold, or valve implant. In the variation shown in the perspective view of FIGS. 38A and 38B, an example is illustrated showing how a self-expanding valve implant or scaffold 398 may be deployed relative to the interventional devices. Once the one or more interventional devices 80, 80' have been deployed and expanded along the mitral valve, catheter 54 may be repositioned above the mitral valve with one or more wires or sutures 392 extending from the catheter 54 and to the one or more links 52, 52'. A pusher catheter or shaft 390 having valve implant or scaffold 392 attached may be urged from the catheter 54 to push the implant or scaffold 398 in its fully expanded shape via openings or loops 394 located along the implant or scaffold 392 through which may be looped around the wires or sutures 392 extend to help guide the implant 398 into position in engagement with the assemblies 80, 80'. The implant 398 may have its lumen 396 positioned to coincide with the valve opening such that the implant 398 is secured above, below, or through the valve. Each of the links may comprise one or more retractable locks 394 which may allow the openings or loops 394 to slide over and force the retraction of the locks 402, as shown in FIG. 39, until the openings or loops 394 have cleared the locks 402 after which they may extend outwardly to lock a position of the valve 398 relative to the interventional devices 80, 80'.

Figure 40A:
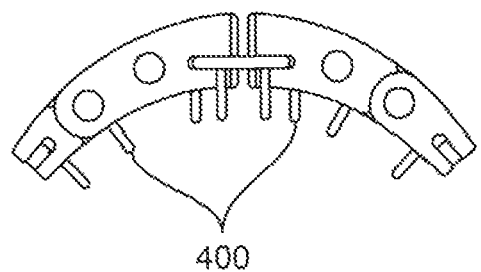
FIGS. 40A to 40B illustrate top and perspective views of variations of rings which may be secured upon the one or more interventional devices.
Figure 40B:
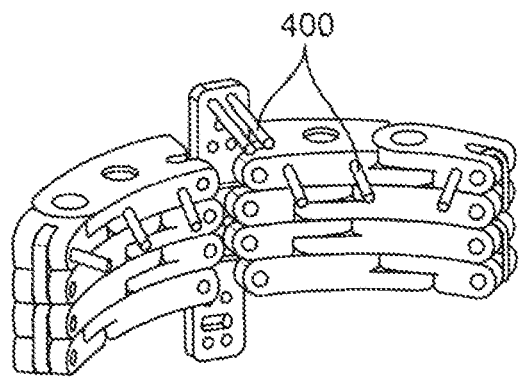

To help secure the implant 398 relative to the valve, the one or more assemblies 80, 80' may incorporate one or more protrusions 400, as previously described, along the arm members facing the valve central region, as shown in the perspective view of FIGS. 40A and 40B. The protrusions 400 may extend inwardly from the arm members and engage the sides of the implant 400 or interstices therein to resist or inhibit any movement between the implant 398 relative to the valve, as shown in FIG. 40A. In this example, implant 398 will be held within catheter 54 until positioned within the interventional devices 80 then released so as to expand into engagement with the inner walls thereof.

Figure 41B:
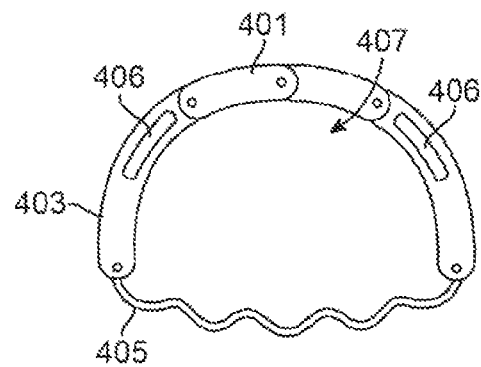
FIGS. 41A to 41D illustrate perspective and tops views of other variations where the one or more interventional devices may incorporate a reinforcement ring.
Figure 41A:
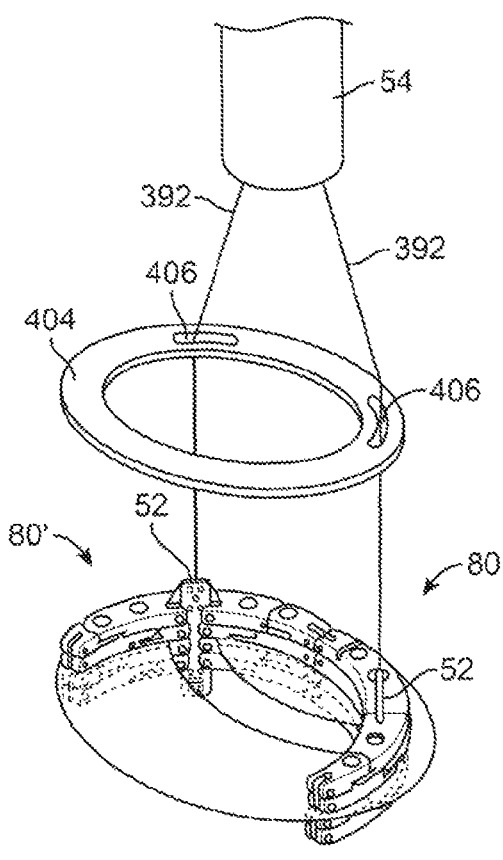

Yet another variation for securing the interventional devices 80, 80' relative to one another as well as to provide an engagement surface for any potential implant is shown in the perspective view of FIG. 41A. With the one or more interventional devices 80, 80' deployed along the valve, a supporting ring 404 having a circumferential structure with one or more openings 406 defined along the circumference may be deployed from the catheter 54 and guided via wires or sutures 392 extending through the openings 406. The terminal ends of the wires or sutures 378 may be attached to the respective links 52, 52' such that the openings 406 may slide directly upon and over the links 52, 52'. Each of the links may comprise one or more retractable locks 402 which may allow the openings 406 to slide over and force the retraction of the locks 402, as shown in FIG. 39, until the openings 406 have cleared the locks 402 after which they may extend outwardly to lock a position of the ring 404 relative to the stabilizing structures 80, 80'.

Figure 41C:
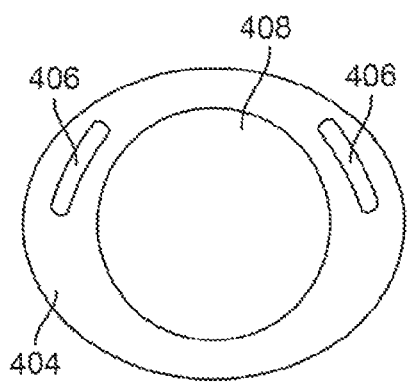
Figure 41D:
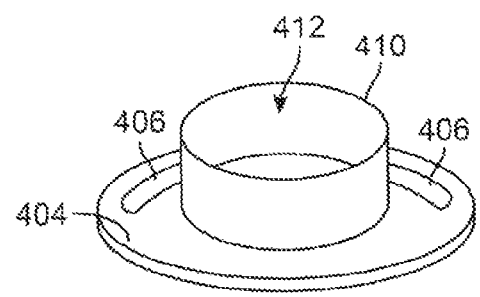

While the support ring 404 may be comprised as a simple ring defining an opening 408 therethrough, as shown in the top view of FIG. 41C, the ring may be configured into alternative variations. One example is shown in the top view of FIG. 41B where supporting ring 403 may comprise a partial ring, such as a C-clip, in which the terminal ends of the clip are coupled to one another via a connecting wire or elastic band 405 such that an opening 407 is defined by the structure. The partial ring may also be comprised of individual segments 401 which are hinged or linked to one another such that the supporting ring 403 may conform to variations in the alignment of the interventional devices 80, 80' or to variations in the anatomy as well while still providing structural support. Another variation is shown in the perspective view of FIG. 41D which illustrates a support ring 404 having a collar 410 which extends axially away from the ring 404 and defines while defining an opening 412 therethrough. Collar 410 may have a more circular shape, greater height and smaller diameter than ring 404 so as to provide a cylindrized platform in which a stented valve may be deployed.

Figure 42B:
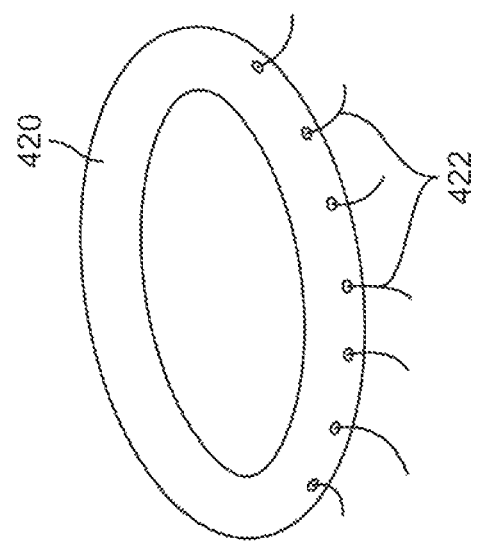
FIGS. 42A and 42B illustrate perspective views of variations of rings further incorporating projections or engagement mechanisms for securement to the leaflets or surrounding annulus.
Figure 42A:
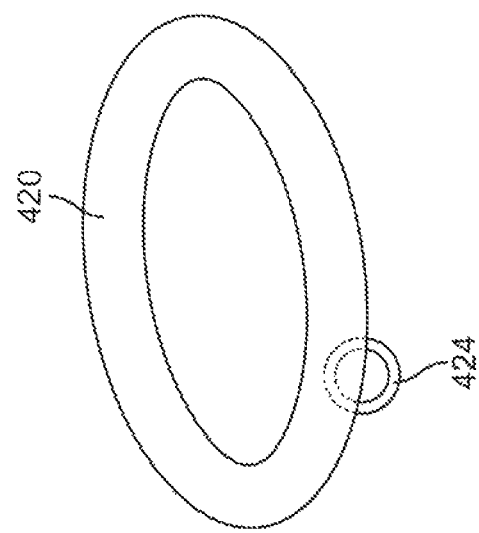

FIGS. 42A to 42B illustrate perspective views of additional ringed structures which may be attached to the one or more interventional devices 80, 80'. In one variation, supra-annular ring 420, shown in FIG. 42A, may comprise a number of projections or protrusions 422 or loop or clip element 424, as shown in FIG. 42B, which extend outwardly from the ring circumference.

In yet another variation of the interventional device, a supporting ring may be utilized in combination with one or more retaining members rather than with an interventional device. FIG. 43A shows a cross-sectional side view of an example of how a ring 452 may be axially-elongated and positioned within a catheter 54 along with proximally and distally positioned retainer members 450, 450B for intravascular delivery. FIG. 43B shows a perspective view of the deployed ring assembly where subannular retainer members 450A, 450B may be configurable from a low profile shape during delivery to a deployed shape in which the distal arms of the retainer members extend into curved, arcuate, or semi-circular configurations for contact the sub-valvular surface of the leaflets. Accordingly, the retainer members 450A, 450B may be made from resilient materials such as shape memory materials (e.g., nickel-titanium alloys, shape memory polymers, etc.) Locking couplings 458A, 458B may be positioned to extend proximally of each respective retainer member 450A, 450B.

The prosthetic supra-annular ring 452 may be shaped or sized similarly to a periphery of the mitral valve and/or be configured to support an implanted prosthetic valve. One or more openings 454A, 454B may also be defined at either end of the ring along the circumference to provide guidance for wire or sutures 456A, 456B which may pass through each respective opening. The couplings 458A, 458B may be attached to respective wire or suture 456A, 456B such that the couplings may be received within the respective openings 454A, 454B defined through the ring 452 in a locking manner when each wire or suture is tensioned to secure a position of each respective retainer member 450A, 450B relative to the ring 452. The couplings 458A, 458B may define one or more tapered members which allow for their insertion into and/or through the openings 454A, 454B and engagement with a flange 457 therein to inhibit their retraction or withdrawal to allow for adjustable securement of the ring 452 to retainer members 450A, 450B upon the mitral valve annulus, as shown in FIG. 43C. Alternatively, various other mechanisms such as ratcheting teeth, pawls, spherical locking elements, hitch/ring assembly, etc. may be used to couple retainer members 450A, 450B to ring 452.

An example of how the ring assembly may be deployed is shown in the partial cross-sectional side views of FIGS.

Figure 44A:
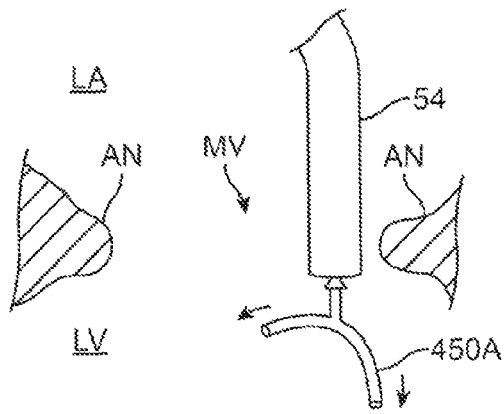
FIGS. 44A to 44F illustrate an example for deploying the subannular stabilizing members and supra-annular ring upon a mitral valve.
Figure 44B:
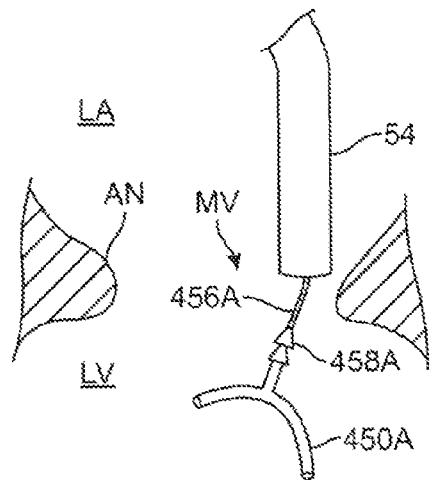
Figure 44C:
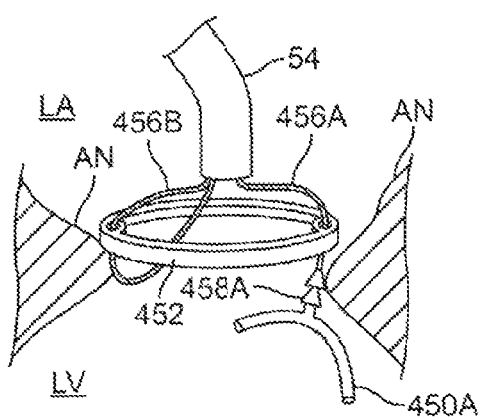
Figure 44D:
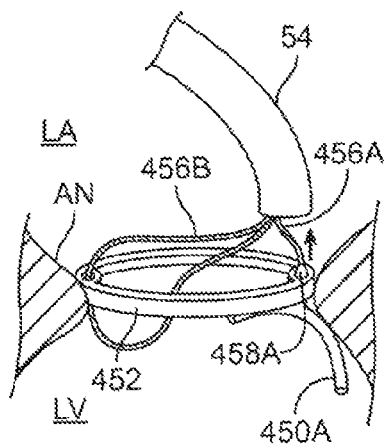
Figure 44E:
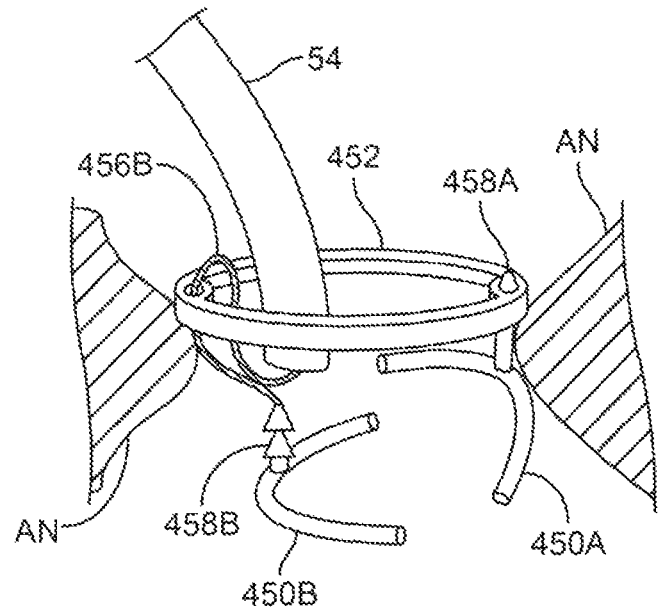
Figure 44F:
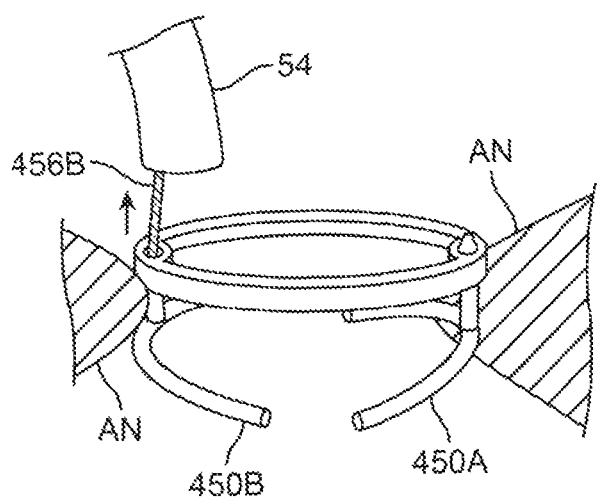

44A to 44F. The mitral valve leaflets are not shown only for clarity. As illustrated in FIGS. 44A and 44B, the distal end of catheter 54 may be placed through a first commissure of the mitral valve MV from the left atrium LA into the left ventricle LV and a first retainer member 450A and coupling 458A may be deployed from the catheter in the subannular space below the leaflets to reconfigure into a deployed configuration. The catheter 54 may be withdrawn proximally into the left atrium LA and the ring 452 may then be ejected from the catheter 54 from within the left atrium LA superior to the mitral valve MV as well as with the tether 456A remaining attached to the first retainer member 450A through the opening in the ring 452. With the catheter 54 used as a backstop against the ring 452, the tether 456A may be tensioned and pulled to draw the coupling 458A into the ring opening to lock the retainer member 450A against the valve annulus AN and/or leaflets as shown in FIGS. 44C and 44D. The catheter 54 distal end may then be placed through the ring 452 in the opposite commissure to deploy the second retainer member 450B inferior to the mitral valve annulus AN and within the left ventricle LV, as shown in FIG. 44E. The tether 456B may then be tensioned to draw the second retainer member 450B against the valve annulus AN and to lock the coupling 458B to the ring to secure the ring 452 position relative to the valve, as shown FIG. 44F.

Figure 45D:
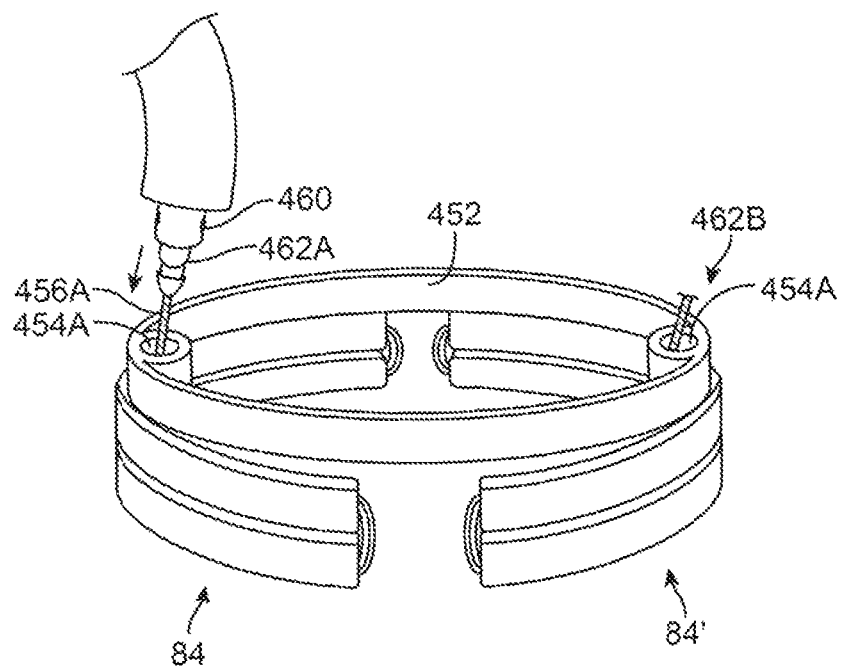
Figure 45E:
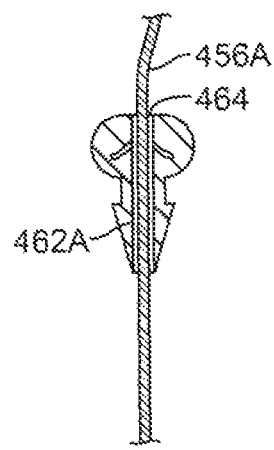

In yet another variation, FIGS. 45A to 45C show another variation illustrating how a ring 452 may be deployed in combination with a distal stabilizing structure 84. As shown in the cross-sectional side view of FIG. 45A, the ring 452 may be axially-elongated into a low-profile configuration for delivery positioned between a distal stabilizing structure 84 and an optional proximal stabilizing structure 84'. The distal stabilizing structure 84 may be deployed from the catheter 54 and secured, as shown in FIG. 45B, in a subannular position. The ring 452 may then be deployed in a supra-annular position and allowed to reconfigure into its deployment shape. With tethers 456A, 456B passing from catheter 54 and through respective openings along the ring 452, a pusher catheter 460 may be deployed to push or urge a respective locking retainer 462A, 462B along a respective tether 456A, 456B to secure the position of the first and second stabilizing assemblies 84, 84' relative to the ring 452, as shown in FIGS. 45C and 45D, such that the valve leaflets are secured therebetween. FIG. 45E shows a cross-sectional side view of an example of a locking retainer 462A having a lumen 464 for sliding along tether 456A (uni-directionally in one example) a pair of angled pawls which engage tether 456A and a tapered portion for locking into the opening defined along the ring 452.

Figure 46A:
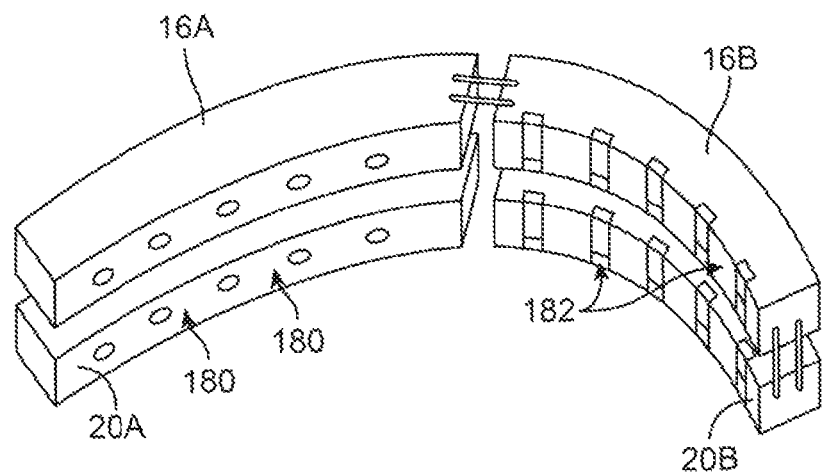
FIGS. 46A and 46B illustrate perspective views of various examples of features, such as pins, castellations, projections, tabs, etc. which may be formed upon the arm members of the interventional device for contact against the leaflet or tissue surfaces or for securing an implanted interventional device.
Figure 46B:
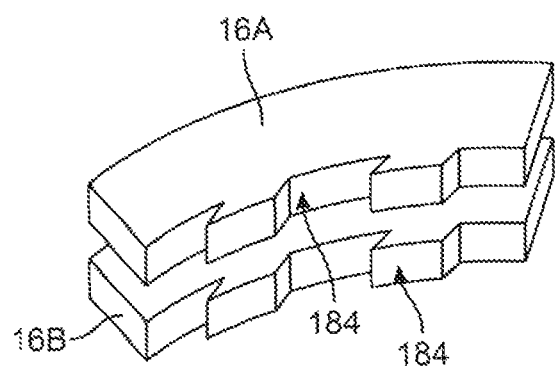

In any of the variations of the interventional devices described herein, various features or projections such as pins 180, castellations 182, raised tabs 184, or any other projections, protrusions, bumps, or features which may facilitate engagement with a replacement mitral valve implant may be formed along one or more arm members, as shown in the perspective views of FIGS. 46A and 46B. These features may be located along the surface of the arm members which face the central region of the mitral valve when deployed or on any other surface of the arm members as may be useful for enhancing engagement with the prosthetic valve.

It should be noted that any of the ring members described above in connection with, e.g. FIGS. 38-46, may be configured to receive a separate catheter-delivered valve for deployment therein, or may have either a temporary or permanent valve pre-mounted therein. Since a relatively long period of time may elapse between placement of the anchor and implantation of the prosthetic valve, a temporary valve sewn into or otherwise secured within the anchoring structures of the invention assures proper regulation of blood flow in the interim. As the name denotes, temporary valves are not intended for long term use, typically being required for a period from about 15 minutes to several hours or at most a few days. Prosthetic valves may be implanted within a temporary valve or may be implanted after the temporary valve has been removed.

V. Intravascular Approaches to the Mitral Valve

Figure 47A:
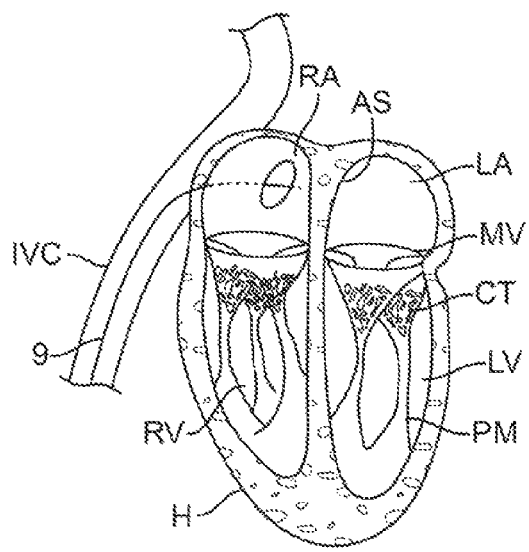
FIGS. 47A to 47F illustrate partial cross-sectional side views of a heart where a catheter assembly may be advanced intravascularly through an inferior vena cava and transseptally into a left atrium of a patient and into proximity to the mitral valve.
Figure 47B:
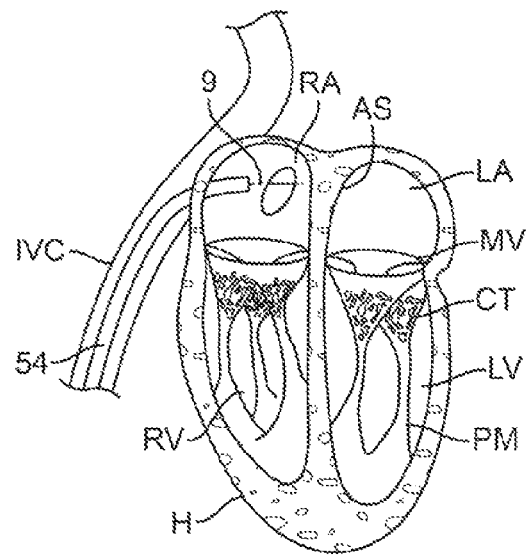
Figure 47C:
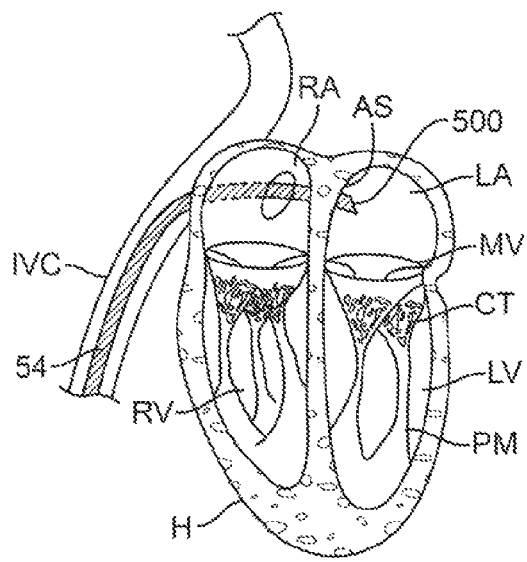
Figure 47D:
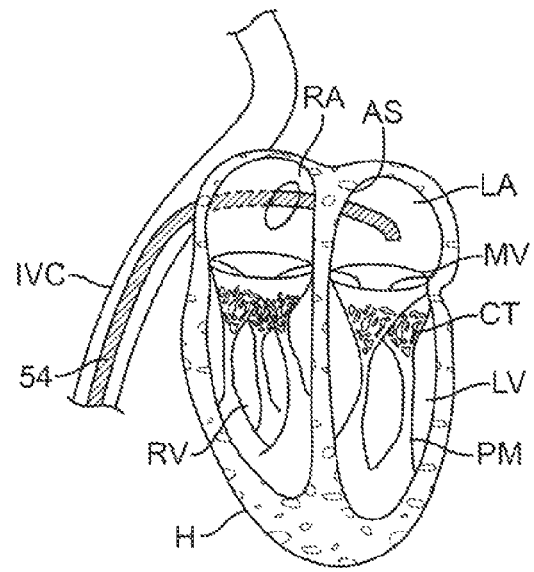

In one example for delivering and deploying one or more interventional devices 10, FIGS. 47A to 47K illustrate partial cross-sectional side views a heart H interior to show a typical antegrade approach. As shown in FIG. 47A, a guidewire 9 may be advanced intravascularly using any number of techniques, e.g., through the inferior vena cava IVC or superior vena cava SVC (not shown), through the atrial septum AS and into the right atrium RA. Catheter 54 may be advanced along the guidewire 9 and into the right atrium RA until reaching the anterior side of the atrial septum AS, as shown in FIG. 47B. Once the catheter 54 reaches the anterior side of the atrial septum IAS, a piercing needle and/or dilator 500 may be advanced through the catheter to cross the atrial septum AS from the right atrium RA into the left atrium LA, as shown in FIG. 47C. At this point, the guidewire 9 may be exchanged for the needle 70 and the catheter sheath withdrawn. A catheter 54 may then be advanced over the guidewire 9 and into the left atrium LA and into a position above the dysfunctional mitral valve MV, as shown in FIG. 3D.

Figure 47E:
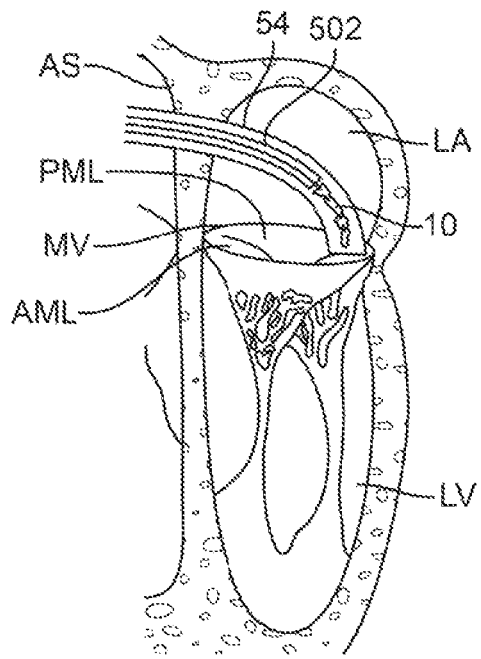
Figure 47F:
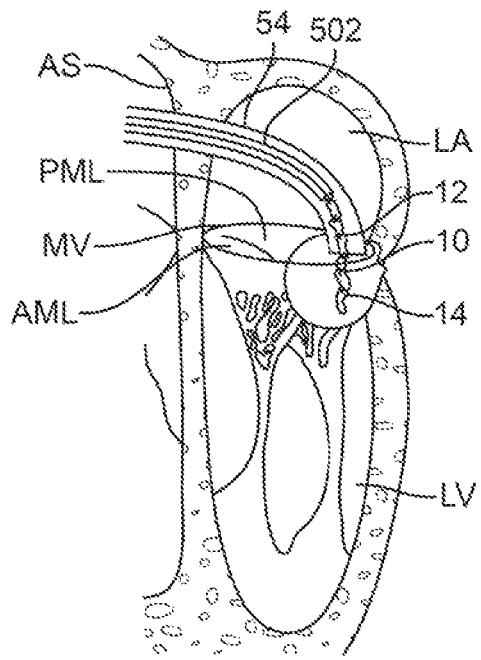
Figure 47G:
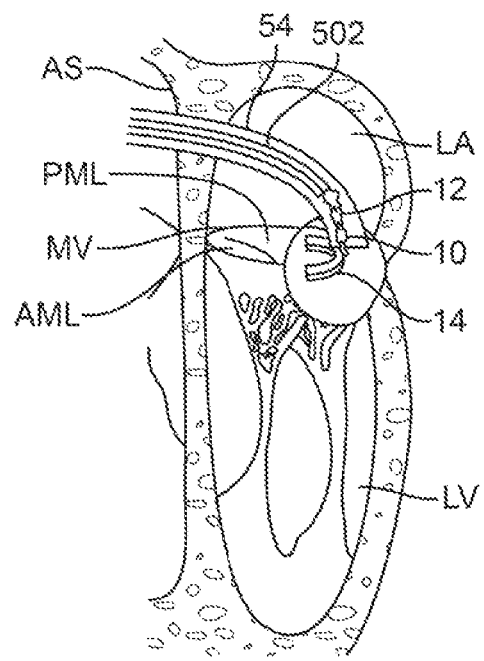
FIGS. 47G to 47J illustrate partial cross-sectional side views where one or more interventional devices may be deployed from a supra-annular approach and reconfigured upon the mitral valve leaflets.

In a typical antegrade approach, the distal opening 262 of the catheter 54 may be advanced into proximity to the mitral valve MV and optionally passed between the posterior mitral leaflet PML and anterior mitral leaflet AML and at least partially past the plane of the mitral valve annulus, as shown in FIG. 47E. A first interventional device 10 is advanced through the catheter 54 to the distal end of the catheter 54. The distal stabilizing structure 14, in its axially-elongated configuration, may then be advanced distally from the catheter 54 and below the valve leaflets and then deployed such that the assembly is reconfigured to its laterally-elongated configuration without interference from the chordae tendineae CT or papillary muscles PM within the left ventricle LV, as shown in FIGS. 47F and 47G.

Figure 47H:
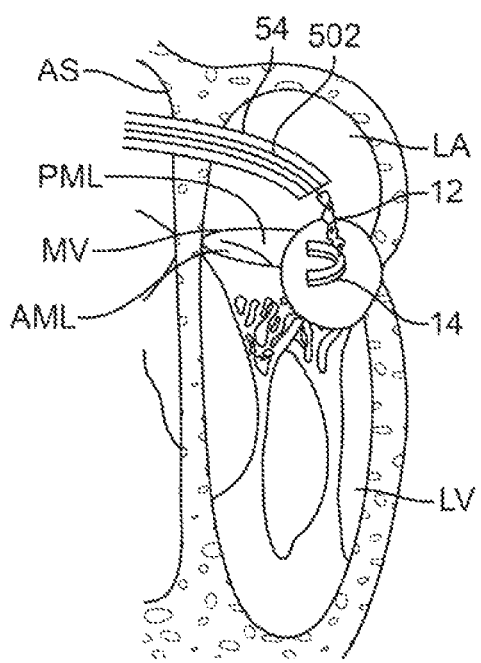
Figure 47I:
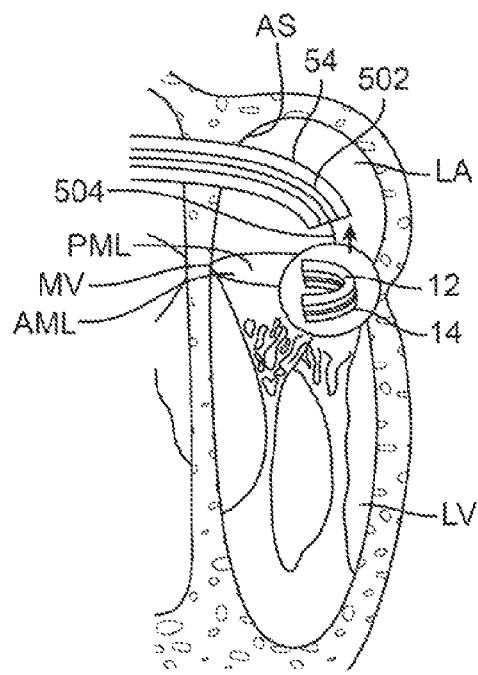

With the distal stabilizing structure 14 deployed in a subannular position, the distal end of catheter 54 may be partially withdrawn further into the left atrium LA and the proximal stabilizing structure 12 may then be deployed from the catheter 54 and reconfigured into its laterally-elongated shape in a supra-annular position, as shown in FIGS. 47H and 47I, such that portions of the posterior and anterior mitral leaflets PML, AML are secured between the arms of the stabilizing structures 12, 14. An actuation member 504 (e.g., wire, suture, catheter, etc.) may be coupled to the interventional device 10 and used to reconfigure and/or lock the proximal and distal stabilizing structures 12, 14 into their laterally-elongated configurations, as previously described herein.

The process may be repeated to position and deploy a second interventional device 10' at a second end of the mitral valve MV such that the leaflets are secured between the arm members of each of the stabilizing assemblies 12, 14 and 12', 14'. With the deployed arm members compressing the leaflets therebetween, the curved or arcuate shape of the deployed assemblies may follow along a periphery or annulus of the mitral valve MV such that a central region of the valve remains uninhibited and the posterior and anterior mitral leaflets PML, AML may coapt sufficiently. The interventional device may further eliminate or reduce prolapse of the leaflets into the left atrium by effectively shortening their length and moving their hinge points inwardly from the heart wall.

Figure 47J:
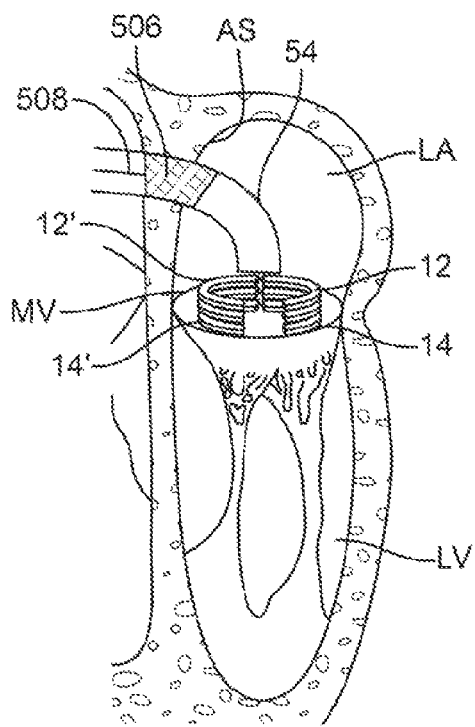
Figure 47K:
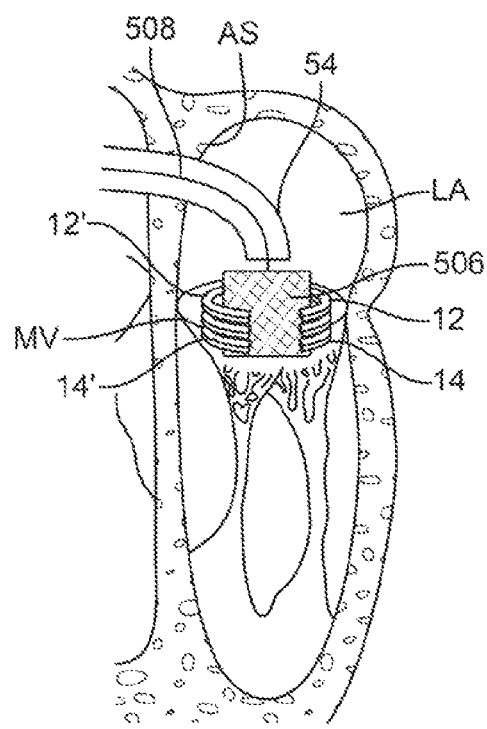
FIG. 47K illustrates how a replacement valve assembly may be optionally delivered and secured to the interventional devices.

While the one or more interventional devices 10, 10' may be utilized alone, a stent, scaffold, or replacement valve assembly 506 may optionally used as well in combination with the one or more assemblies. FIGS. 47J and 47K show one example where replacement valve assembly 506 may be further delivered through the catheter 54 via delivery wire or catheter 508 and positioned within the central region defined between the stabilizing structures 12, 14 and 12', 14'. The valve assembly 506 may then be expanded into engagement with the stabilizing structures such that the valve assembly 506 extends above, below, or entirely through the mitral valve MV. Examples of preassembled, percutaneous prosthetic valves include, e.g., the CoreValve Revalving™ System from Medtronic/CoreValve Inc. (Irvine, Calif., USA), Edwards-Sapien from Edwards Lifesciences (Irvine, Calif., USA).

Figure 48A:
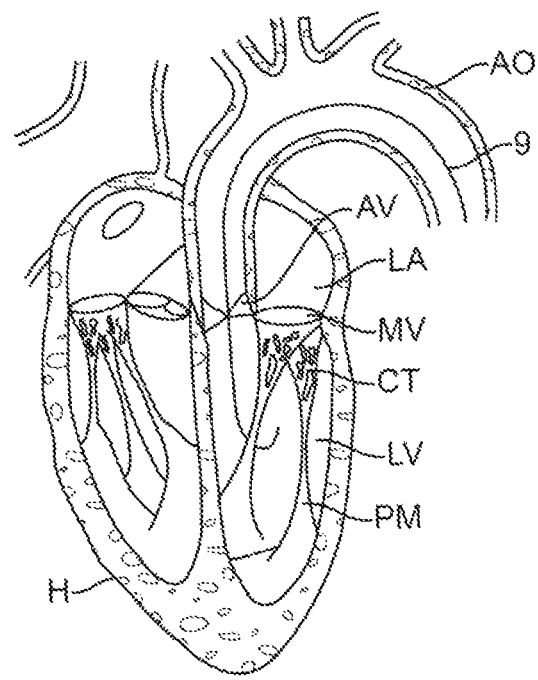
FIGS. 48A to 48D illustrate partial cross-sectional side views of another example where a catheter assembly may be advanced intravascularly through an aortic valve and into a left ventricle of a patient.
Figure 48B:
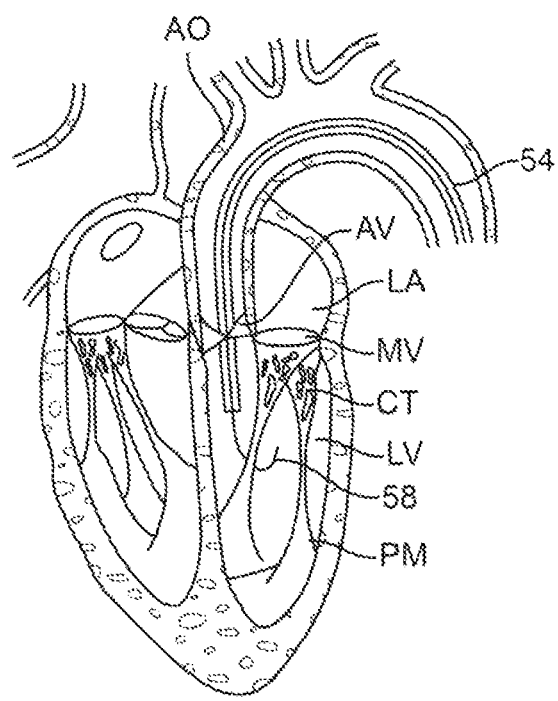
Figure 48C:
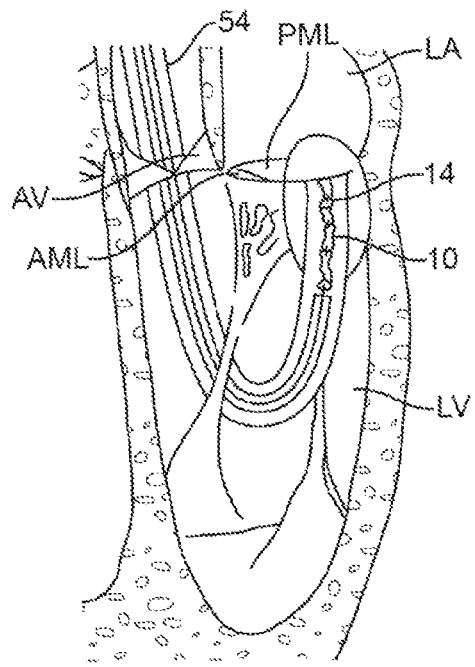
Figure 48D:
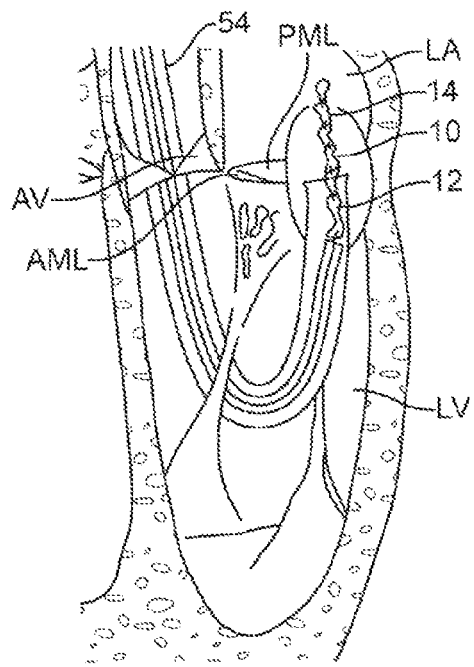
Figure 48E:
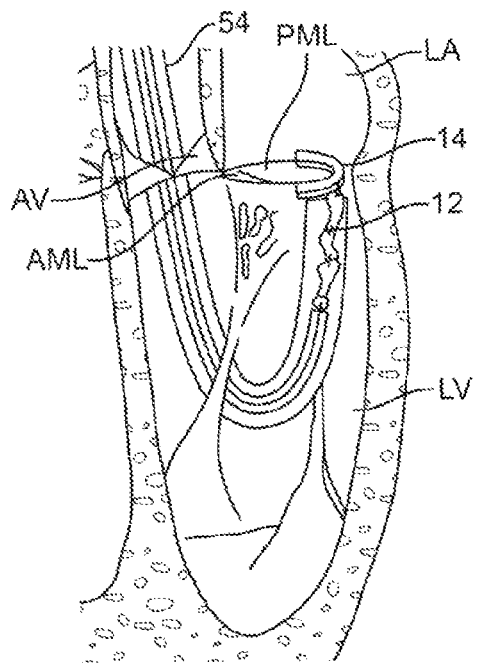
FIGS. 48E to 48I illustrate how one or more interventional devices may be deployed from an subannular approach and reconfigured upon the mitral valve leaflets with an optional replacement valve assembly.
Figure 48F:
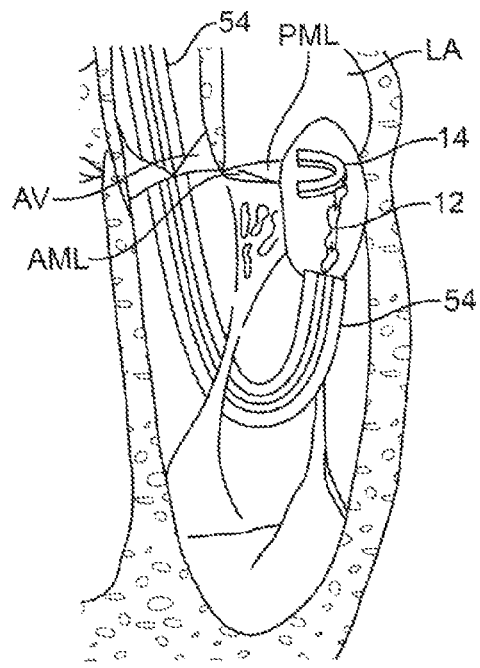
Figure 48G:
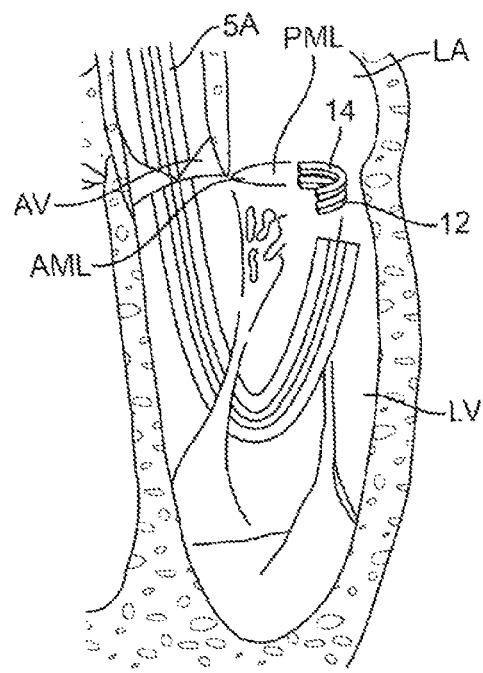
Figure 48H:
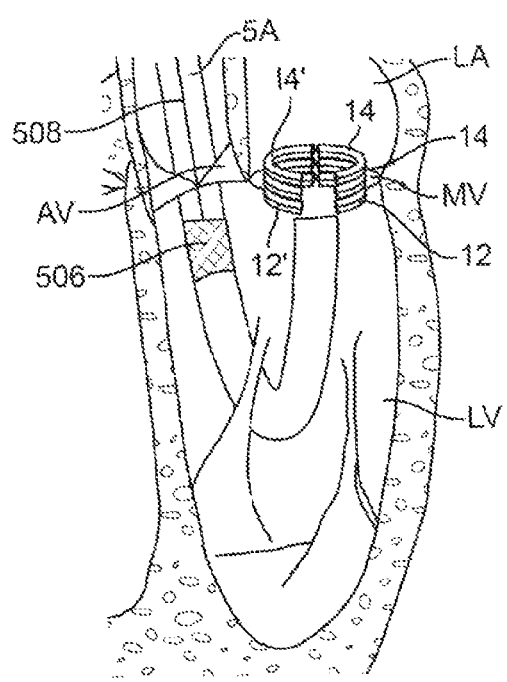

FIGS. 48A to 48I illustrate another variation for delivering and deploying one or more interventional devices using a typical retrograde approach. In this example, a guidewire 9 may be advanced intravascularly via a femoral approach through the aorta AO and aortic valve AV and into the left ventricle LV of the heart H, as shown in FIG. 48A. The catheter 54 may be advanced along the guidewire 9 until the catheter distal end is positioned within the left ventricle LV in proximity to the mitral valve MV, as shown in FIGS. 48B and 48C. The distal end of the catheter 54 may be optionally advanced at least partially through the mitral valve MV and into the left atrium LA where the distal stabilizing structure 14 may be deployed from the catheter 54, as shown in FIG. 48D, and reconfigured into its expanded configuration for contact against the supra-annular surfaces of the posterior and anterior mitral leaflets PML, AML, as shown in FIG. 48E. With the distal stabilizing structure 14 deployed, the catheter 54 may be retracted at least partially back into the left ventricle LV where the proximal stabilizing structure 12 may be deployed from the catheter and then reconfigured into its deployed configuration, as shown in FIGS. 48F and 48G.

Figure 48I:
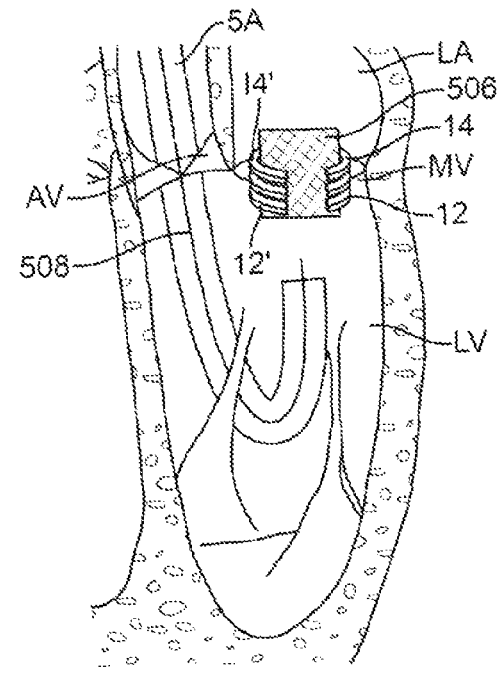

A second interventional device 10' may be deployed. A second pair of proximal and distal structures 12', 14' may be deployed from the catheter 54 and positioned along the mitral valve MV in an apposed position relative to the first assemblies 12, 14 using the same subannular approach, as shown in FIG. 4H. As previously described, a stent, scaffold, or replacement valve assembly 506 may be optionally delivered through the catheter 54 and positioned through the central region defined between the stabilizing assemblies 12, 14 and 12', 14' and deployed therein such that the valve assembly 506 extends above, below, or through the mitral valve MV, as shown in FIG. 48I. Examples of preassembled, percutaneous prosthetic valves include, e.g., the CoreValve Revalving™ System from Medtronic/CoreValve Inc. (Irvine, Calif., USA), Edwards-Sapien.

In any of the variations and examples described herein, different features may be combined between the embodiments described in various combinations depending upon the desired device and results.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

We claim:

1. A method for the treatment of conditions affecting a heart valve, comprising:
    positioning a first assembly having a first pair of first arm members pivotally coupled to a second pair of second arm members adjacent to the heart valve, wherein the individual first arm members are coupled together at first joint and the individual second arm members are coupled together at a second joint;
    reconfiguring the first assembly from a low-profile delivery configuration to an expanded curved configuration against a first surface of the heart valve such that the first and second joints are spaced laterally apart from each other by lengths of the individual first and second arm members;
    positioning a second assembly having a third pair of third arm members pivotally coupled to a fourth pair of fourth arm members adjacent to the heart valve, wherein the individual third arm members are coupled together at a third joint and the individual fourth arm members are coupled together at a fourth joint; and
    reconfiguring the second assembly from a low-profile delivery configuration to an expanded curved configuration against a second surface of the heart valve such that the third and fourth joints are spaced laterally apart from each other by lengths of the individual third and fourth arm members and native valve leaflets and/or a native annulus are compressed between the first and second assemblies.

2. The method of claim 1 wherein positioning a first assembly comprises advancing the first assembly intravascularly into an atrial chamber.

3. The method of claim 1 wherein positioning a first assembly comprises deploying the first assembly from the low-profile delivery configuration from within a catheter lumen.

4. The method of claim 1 wherein reconfiguring the first assembly comprises urging a distal end of the first assembly proximally towards a proximal end of the first assembly.

5. The method of claim 1 wherein positioning a second assembly comprises deploying the second assembly from the low-profile delivery configuration from within a catheter lumen.

6. The method or claim 1 wherein reconfiguring the second assembly comprises urging a distal end of the second assembly towards a proximal end of the second assembly.

7. The method of claim 1 further comprising locking the first and second assemblies in the compressed configuration.

8. The method of claim 1 further comprising positioning a third assembly and a fourth assembly coupled to the third assembly into apposition relative to the first and second assemblies along the heart valve.

9. The method of claim 1 further comprising anchoring a valve prosthesis against or along the first and second assemblies and through the heart valve.

10. A method for the treatment of conditions affecting the mitral valve, comprising:
    positioning a first assembly having a first pair of first arm members pivotally coupled to a second pair of second arm members along a subannular position;

positioning a second assembly having a third pair of third arm members pivotably coupled to a fourth pair of fourth arm members along a supra-annular position; and pivoting the individual first arm members and second arm members about corresponding first and second joints to move the first assembly from a low-profile delivery configuration to an expanded curved configuration to extend along and engage a ventricular surface of a mitral valve annulas, wherein the first and second joints are spaced laterally apart from each other by lengths of the first and second arms in the expanded curved configuration; and pivoting the individual third arm members and fourth arm members about corresponding third and fourth joints to move the second assembly from a low-profile delivery configuration to an expanded curved configuration such that the second assembly extends along and engages an atrial surface of the mitral valve annulus, wherein the third and fourth joints are spaced laterally apart from each other by lengths of the third and fourth arms in the expanded curved configuration, and wherein the mitral valve annulus is compressed between the first and second assemblies when the first and second assemblies are in the expanded curved configuration.

* * * * *